(12) United States Patent
Ozcan et al.

(10) Patent No.: US 7,365,851 B2
(45) Date of Patent: Apr. 29, 2008

(54) METHOD OF MEASURING A PHYSICAL FUNCTION USING A COMPOSITE FUNCTION WHICH INCLUDES THE PHYSICAL FUNCTION AND AN ARBITRARY REFERENCE FUNCTION

(75) Inventors: Aydogan Ozcan, Menlo Park, CA (US); Michel J. F. Digonnet, Palo Alto, CA (US); Gordon S. Kino, Stanford, CA (US)

(73) Assignee: The Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/747,177

(22) Filed: May 10, 2007

(65) Prior Publication Data

US 2007/0211253 A1 Sep. 13, 2007

Related U.S. Application Data

(60) Continuation of application No. 11/356,275, filed on Feb. 16, 2006, now Pat. No. 7,236,247, which is a division of application No. 10/645,331, filed on Aug. 21, 2003, now Pat. No. 7,050,169, which is a continuation-in-part of application No. 10/378,591, filed on Mar. 3, 2003, now Pat. No. 6,856,393, which is a continuation-in-part of application No. 10/357,275, filed on Jan. 31, 2003, now Pat. No. 7,133,134.

(60) Provisional application No. 60/405,405, filed on Aug. 21, 2002.

(51) Int. Cl.
*G01N 21/59* (2006.01)

(52) U.S. Cl. ........................ 356/432; 359/359

(58) Field of Classification Search ........ 356/432–436, 356/444, 600, 605–606, 614, 622, 318; 359/371, 359/386, 495, 359, 236; 385/8
See application file for complete search history.

(56) References Cited

U.S. PATENT DOCUMENTS 3,880,630 A 4/1975 Izawa (Continued)

FOREIGN PATENT DOCUMENTS

JP 2000 329618 A 11/2000

(Continued)

OTHER PUBLICATIONS

Alley, Thomas G., et al., Space charge dynamics in thermally poled fused silica, *Journal of Non-Crystalline Solids*, vol. 242, 1998, pp. 165-176.

(Continued)

*Primary Examiner*—Tarifur R Chowdhury
(74) *Attorney, Agent, or Firm*—Knobbe Martens Olson & Bear, LLP

(57) ABSTRACT

A method for measuring a physical function forms a symmetric composite function by combining the physical function with a reference function. The method obtains a Fourier transform of the symmetric composite function. The method calculates an inverse Fourier transform of the obtained Fourier transform, wherein the calculated inverse Fourier transform provides information regarding the physical function. The physical function can be a nonlinearity profile of a sample with at least one sample surface. The physical function can alternatively by a sample temporal waveform of a sample optical pulse.

19 Claims, 39 Drawing Sheets

U.S. PATENT DOCUMENTS

| | | | |
|---|---|---|---|
| 4,674,824 A | 6/1987 | Goodman et al. | |
| 4,778,236 A | 10/1988 | Miyawaki | |
| 4,792,230 A | 12/1988 | Naganuma et al. | |
| 4,985,178 A | 1/1991 | Tam | |
| 5,053,696 A | 10/1991 | Williamson et al. | |
| 5,071,249 A | 12/1991 | Takahashi et al. | |
| 5,086,239 A | 2/1992 | Wang | |
| 5,194,918 A | 3/1993 | Kino et al. | |
| 5,220,451 A | 6/1993 | Gotoh et al. | |
| 5,239,407 A | 8/1993 | Brueck et al. | |
| 5,247,601 A | 9/1993 | Myers et al. | |
| 5,262,890 A | 11/1993 | Berkovic et al. | |
| 5,309,532 A | 5/1994 | Chang et al. | |
| 5,317,147 A | 5/1994 | Dandliker et al. | |
| 5,368,782 A | 11/1994 | Gotoh et al. | |
| 5,420,717 A | 5/1995 | Tabata | |
| 5,434,699 A | 7/1995 | Berkovic et al. | |
| 5,481,636 A | 1/1996 | Fukude et al. | |
| 5,523,840 A | 6/1996 | Nishizawa et al. | |
| 5,530,544 A | 6/1996 | Trebino et al. | |
| 5,615,041 A | 3/1997 | Field et al. | |
| 5,737,116 A | 4/1998 | Kadowaki et al. | |
| 5,986,798 A | 11/1999 | Karlsson et al. | |
| 6,043,884 A * | 3/2000 | Curbelo | 356/502 |
| 6,456,380 B1 * | 9/2002 | Naganuma | 356/450 |
| 6,479,822 B1 * | 11/2002 | Nelson et al. | 250/341.1 |
| 6,650,466 B1 * | 11/2003 | Wise et al. | 359/328 |
| 6,728,273 B2 * | 4/2004 | Perry | 372/18 |
| 6,856,393 B2 * | 2/2005 | Ozcan et al. | 356/432 |
| 7,050,169 B2 * | 5/2006 | Ozcan et al. | 356/432 |
| 7,133,134 B2 * | 11/2006 | Ozcan et al. | 356/432 |
| 7,236,247 B2 * | 6/2007 | Ozcan et al. | 356/432 |
| 2004/0036880 A1 | 2/2004 | Ozcan et al. | |
| 2004/0044714 A1 | 3/2004 | Ozcan et al. | |
| 2004/0133614 A1 | 7/2004 | Ozcan et al. | |

FOREIGN PATENT DOCUMENTS

JP            2001 083015 A      3/2001

OTHER PUBLICATIONS

Bonfrate, G., et al., Parametric fluorescence in periodically poled silica fibers, *Applied Physics Letters*, vol. 75, No. 16, Oct. 18, 1999, pp. 2356-2358.

Faccio, D., et al., Dynamics of the second-order nonlinearity in thermally poled silica glass, *Applied Physics Letters*, vol. 79, No. 17, Oct. 22, 2001, pp. 2687-2689.

Ferreira, Paulo Jorge S.G., Interpolation and the Discrete Papoulis-Gerchberg Algorithm, *IEEE Transactions On Signal Processing*, vol. 42, No. 10, Oct. 1994, pp. 2596-2606.

PCT/US 03/26311 Invitation to Pay, Aug. 21, 2003, The Board of Trustees of the Leland Stanford Junior University.

PCT/US03/26311 ISR dated Jun. 3, 2004, Aug. 21, 2003, The Board of Trustees of the Leland Stanford Junior University.

PCT/US2004/039320 ISR & Written Opinion dated Jun. 16, 2005, Jun. 29, 2005, The Board of Trustees of the Leland Stanford Junior University.

Fienup, J.R., "Reconstruction of an object from the modulus of its Fourier transform," *Optics Letters*, vol. 3, No. 1, Jul. 1978, pp. 27-29.

Fienup, J.R., "Phase retrieval algorithms: a comparison," *Applied Optics*, vol. 21, No. 15, Aug. 1, 1982, pp. 2758-2769.

Fisher, Robert A., et al., Transient analysis of Kerr-like phase conjugators using frequency-domain techniques, *Physical Review A*, vol. 23, No. 6, Jun. 1981, pp. 3071-3083.

Kashyap, Raman, et al., Phase-matched second harmonic generation by periodic poling of fused silica, *Applied Physics Letters*, vol. 64, No. 11, Mar. 14, 1994, pp. 1332-1334.

Kazansky, P.G., et al., Thermally poled silica glass: Laser induced pressure pulse probe of charge distribution, *Applied Physics Letters*, vol. 68, No. 2, Jan. 8, 1996, pp. 269-271.

Liu, Alice C., et al., Advances in the measurement of the poled silica nonlinear profile, *SPIE*, vol. 3542, Nov. 1998, pp. 115-119.

Maker, P.D., et al., Effects of Dispersion and Focusing on the Production of Optical Harmonics, *Physical Review Letters*, vol. 8, No. 1, Jan. 1, 1962, pp. 21-22.

Millane, R.P., Analytic Properties of the Hartley Transform and their Implications, *Proceedings of the IEEE*, vol. 82, No. 3, Mar. 1994, pp. 413-428.

Miller, D.A.B., Time reversal of optical pulses by four-wave mixing, *Optics Letters*, vol. 5, No. 7, Jul. 1980, pp. 300-302.

Myers, R.A., et al., Large second-order nonlinearity in poled fused silica, *Optics Letters*, vol. 16, No. 22, Nov. 15, 1991, pp. 1732-1734.

Nakajima, N., Reconstruction of a real function from its Hartley-transform intensity, *J. Opt. Soc. Am. A.*, vol. 5, No. 6, Jun. 1988, pp. 858-863.

Ozcan, A., et al., *A simple post-processing technique to improve the retrieval accuracy of second-order nonlinearity profiles*, Edward L. Ginzton Laboratory: Stanford University, Stanford, California 94305; © 2004 Optical Society of America, 2 pages.

Ozcan, A., et al., Cylinder-assisted Maker-fringe Technique, *Electronics Letters*, vol. 39, No. 25, Dec. 11, 2003, 2 pages.

Ozcan, A., et al., *Improved Fourier transform technique to determine second-order optical nonlinearity profiles*, Edward L. Ginzton Laboratory: Stanford University, Stanford, California 94305; © 2003 Optical Society of America, 3 pages.

Ozcan, A., et al., Improved technique to determine second-order optical nonlinearity profiles using two different samples, *Applied Physics Letters*, vol. 84, No. 5, Feb. 2, 2004, pp. 681-683.

Ozcan, A., et al., Inverse Fourier transform technique to determine second-order optical nonlinearity spatial profiles, *Applied Physics Letters*, vol. 82, No. 9, Mar. 3, 2003, pp. 1362-1364.

Ozcan, A., et al., Erratum: Inverse Fourier transform technique to determine second-order optical nonlinearity spatial profiles, *Applied Physics Letters*, vol. 83, No. 8, Aug. 25, 2003, p. 1679.

Ozcan, A., et al., *Post-processing of the second-order optical nonlinearity profile of thin films*, Edward L. Ginzton Laboratory: Stanford University, Stanford, California 94305; © 2004 Optical Society of America, 2 pages.

Ozcan, A., et al., Simplified inverse Fourier transform technique to determine second-order optical nonlinearity profiles using a reference sample, *Electronics Letters*, vol. 40, No. 9, Apr. 29, 2004, 2 pages.

Peri, David, "Optical implementation of a phase retrieval algorithm," *Applied Optics*, vol. 26, No. 9, May 1, 1987, pp. 1782-1785.

Pureur, D., et al., Absolute measurement of the second-order nonlinearity profile in poled silica, *Optics Letters*, vol. 23, No. 8, Apr. 15, 1998, pp. 588-590.

Quatieri, Thomas F., Jr., et al., Iterative techniques for minimum phase signal reconstruction from phase or magnitude, *IEEE Trans. Acoust. Speech, Signal Processing*, vol. 29, 1981, pp. 1187-1193.

Qui, Mingxin, et al., Double fitting of Maker fringes to characterize near-surface and bulk second-order nonlinearities in poled silica, *Applied Physics Letters*, vol. 76, No. 23, Jun. 5, 2000, pp. 3346-3348.

Qui, Mingxin, et al., Erratum: "Double fitting of Marker fringes to characterize near-surface and bulk second-order nonlinearities in poled silica," *Applied Physics Letters*, vol. 77, No. 23, Dec. 4, 2000, p. 3863.

Quiquempois, Y., et al., Localisation of the induced second-order non-linearity within Infrasil and Suprasil thermally poled glasses, *Optics Communications*, vol. 176, Apr. 1, 2000, pp. 479-487.

Rosenthal, Amir, et al., Inverse Scattering Algorithm for Reconstructing Strongly Reflecting Fiber Bragg Gratings, *IEEE Journal of Quantum Electronics*, vol. 39, No. 8, Aug. 2003, pp. 1018-1026.

Sun, P.C., et al., Femtosecond pulse imaging: ultrafast optical oscilloscope, *J. Opt. Soc. Am. A*, vol. 14, No. 5, May 1997, pp. 1159-1170.

Watanabe, Shigeki, et al., Compensation of Chromatic Dispersion in a Single-Mode Fiber by Optical Phase Conjugation, *IEEE Photonics Technology Letters*, vol. 5, No. 1, Jan. 1993, pp. 92-95.

Weiner, Andrew, M., et al., Femtosecond Pulse Shaping for Synthesis, Processing, and Time-to-Space Conversion of Ultrafast Optical Waveforms, *IEEE Journal Of Selected Topics In Quantum Electronics*, vol. 4, No. 2, Mar./Apr. 1998, pp. 317-331.

Weiner, Andrew M., et al., Femtosecond Spectral Holography, *IEEE Journal Of Quantum Electronics*, vol. 28, No. 10, Oct. 1992, pp. 2251-2256.

Xu, Zhiling, et al., "Nonuniform bulk second-order optical nonlinearity in $PbO/B_2O_3$ glass," *Applied Physics Letters*, vol. 77, No. 1, Jul. 3, 2000, pp. 70-72.

Yariv, Amnon, et al., Compensation for channel dispersion by nonlinear optical phase conjugation, *Optics Letters*, vol. 4, No. 2, Feb. 1979, pp. 52-54.

* cited by examiner

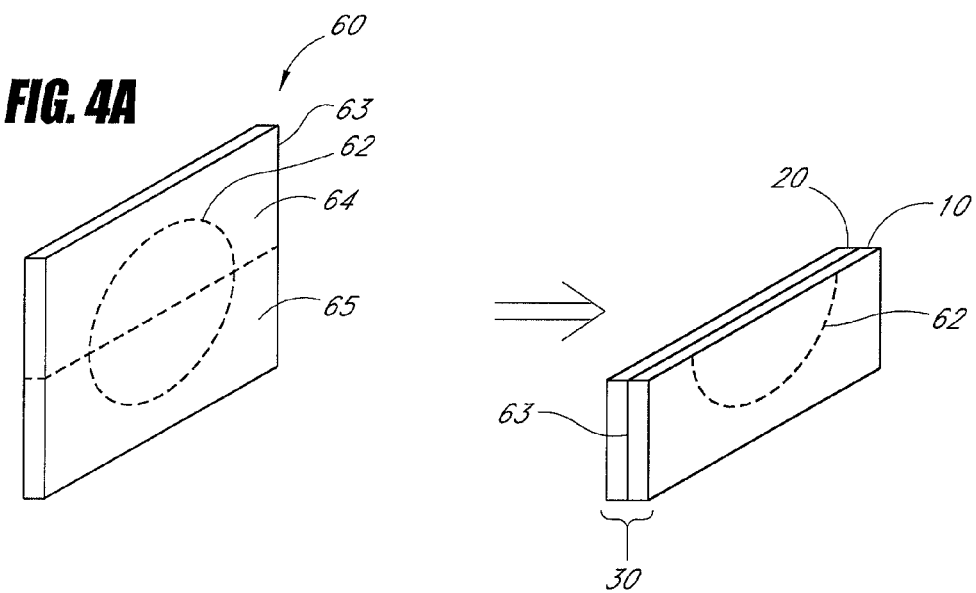
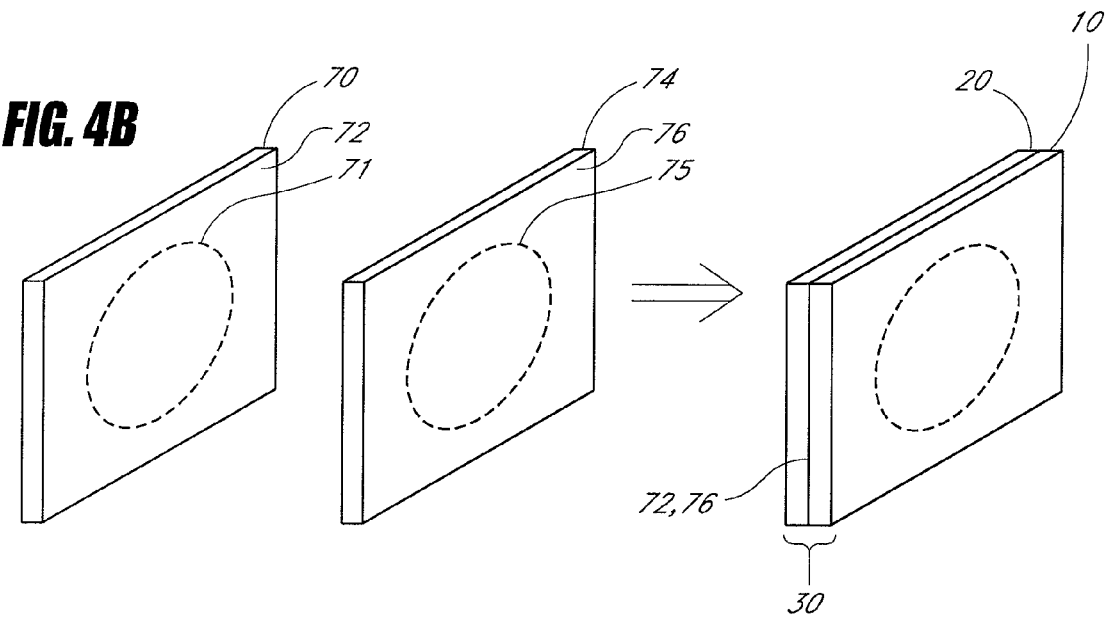

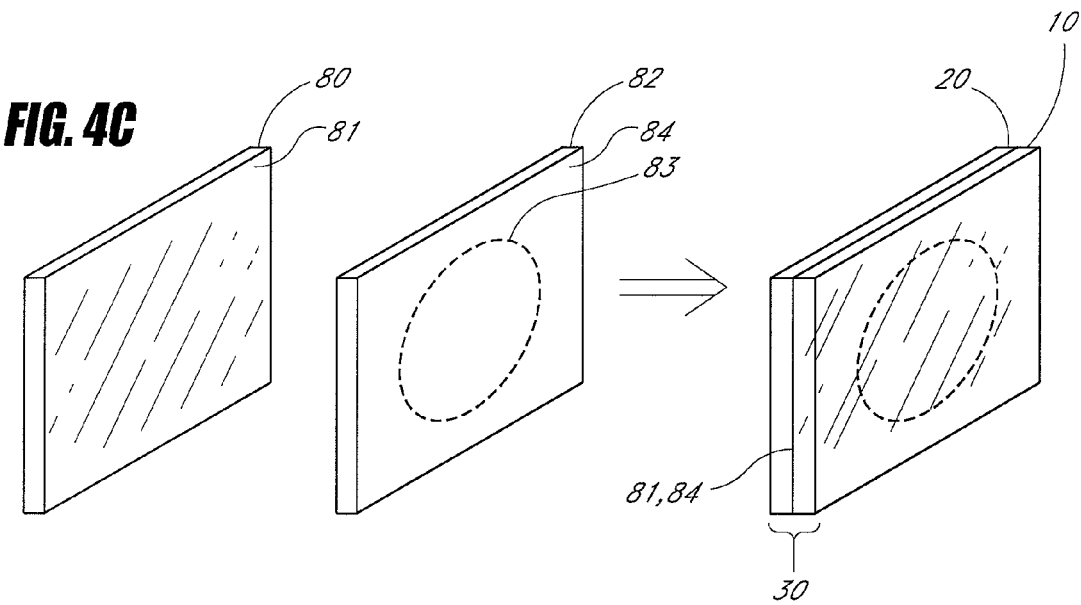
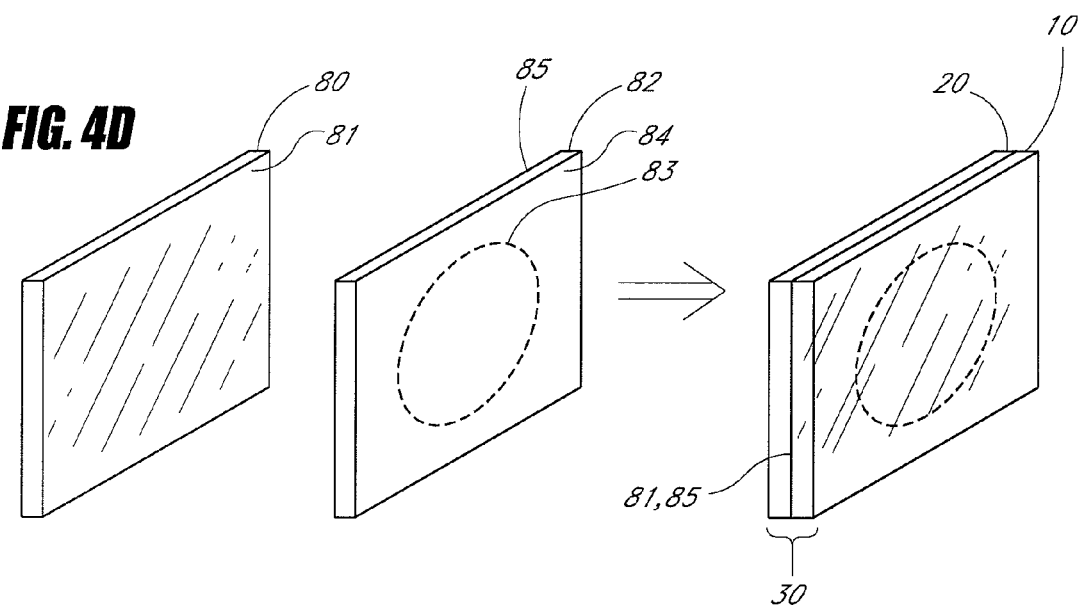

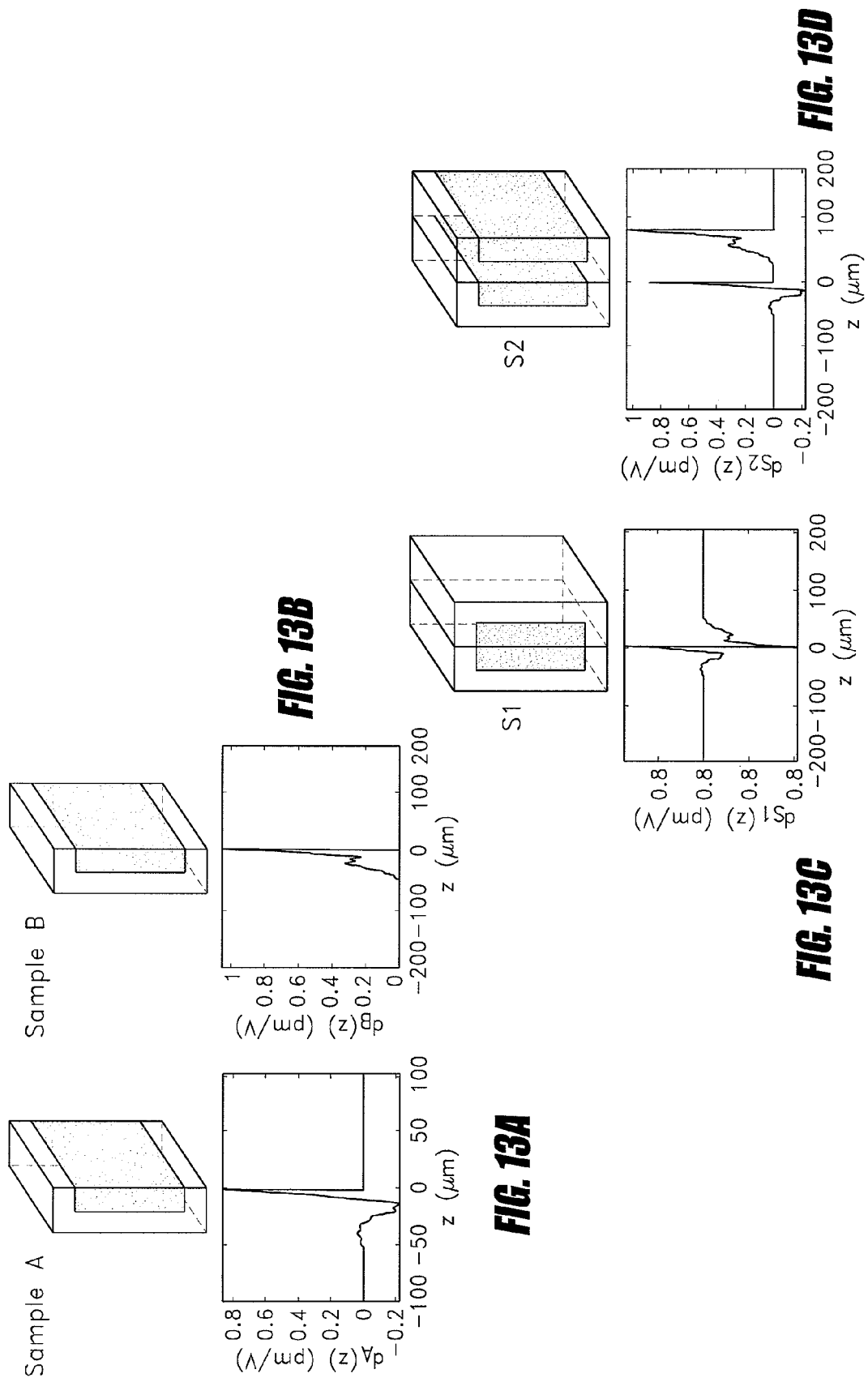

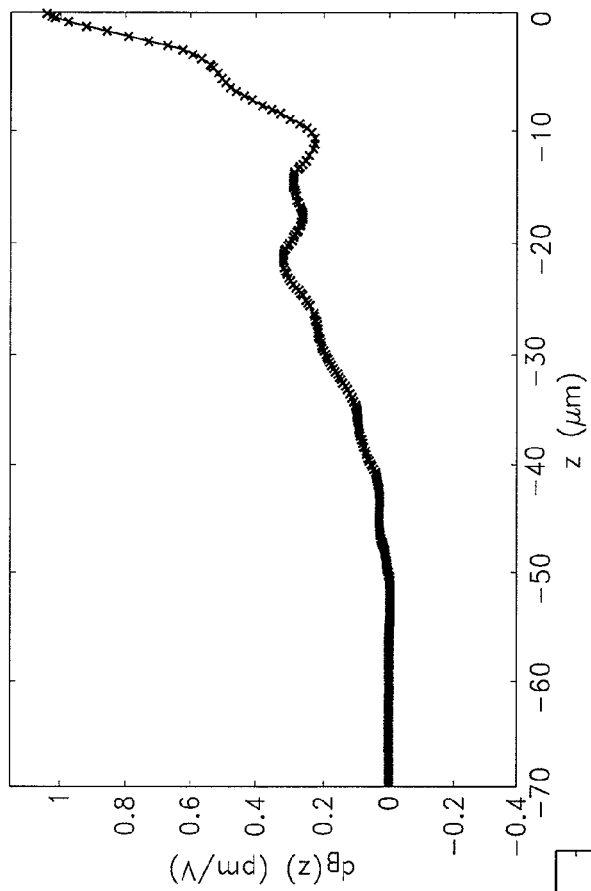
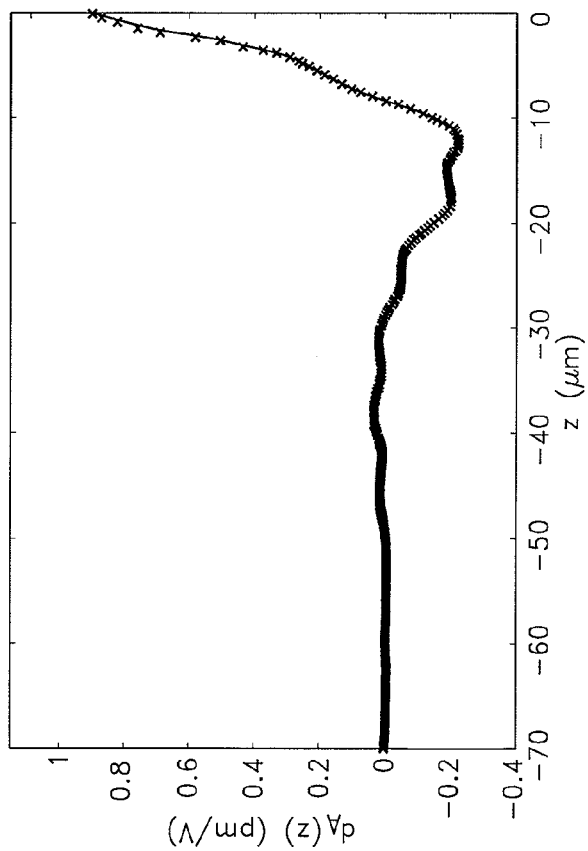
FIG. 15B
FIG. 15A

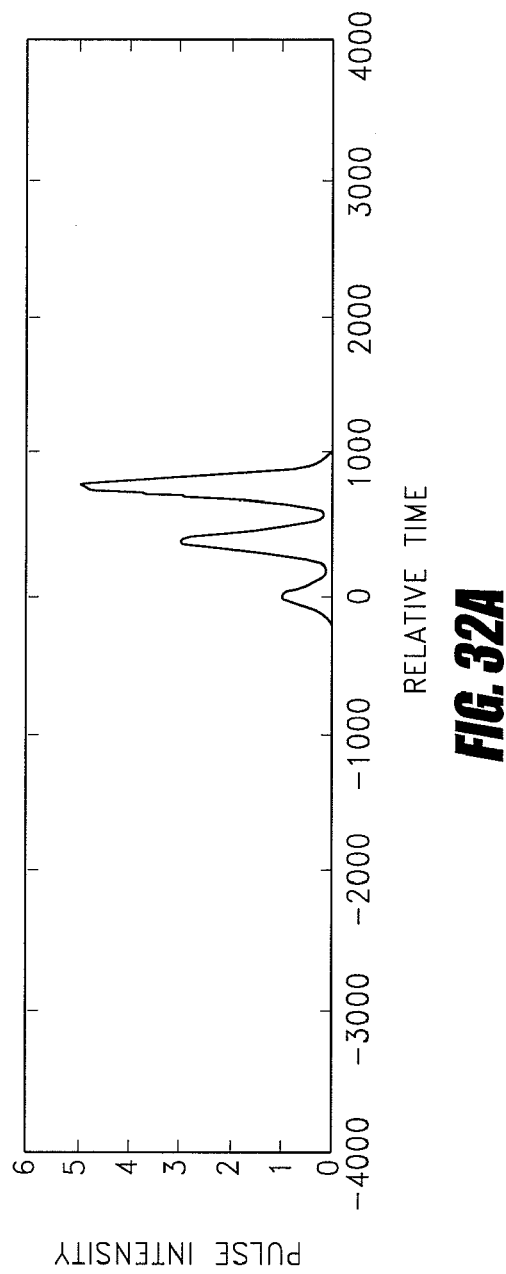
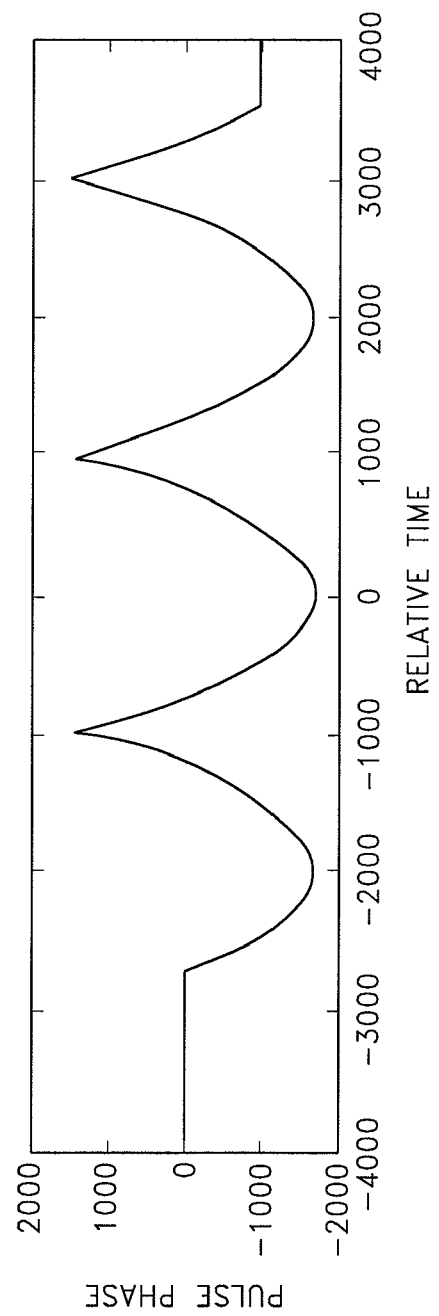
FIG. 32A
FIG. 32B

METHOD OF MEASURING A PHYSICAL FUNCTION USING A COMPOSITE FUNCTION WHICH INCLUDES THE PHYSICAL FUNCTION AND AN ARBITRARY REFERENCE FUNCTION

CLAIM OF PRIORITY

This application is a continuation of and claims priority to, U.S. patent application Ser. No. 11/356,275, filed Feb. 16, 2006, now U.S. Pat. No. 7,236,247 which is a divisional application of, U.S. patent application Ser. No. 10/645,331, filed Aug. 21, 2003, now U.S. Pat. No. 7,050,169 which is a continuation-in-part of U.S. patent application Ser. No. 10/378,591, filed Mar. 3, 2003 now U.S. Pat. No. 6,856,393 (now U.S. Pat. No. 6,856,393, issued Feb. 15, 2005), which is a continuation-in-part of U.S. patent application Ser. No. 10/357,275, filed Jan. 31, 2003, now U.S. Pat. No. 7,133,134 which claims the benefit of U.S. Provisional Application No. 60/405,405, filed Aug. 21, 2002. U.S. patent application Ser. No. 11/356,275, U.S. patent application Ser. No. 10/645,331, U.S. patent application Ser. No. 10/378,591, U.S. patent application Ser. No. 10/357,275, and U.S. Provisional Application No. 60/405,405 are incorporated by reference in their entireties herein.

BACKGROUND OF THE INVENTION

1. Field of the Invention

The present invention relates generally to the field of measuring attributes of a physical system and, more particularly, relates to methods of measuring a non-symmetric physical function.

2. Description of the Related Art

Various optical devices are based on induced second-order susceptibilities in silica-based glass waveguides (e.g., electro-optic modulators, switches, parametric amplifiers). For example, G. Bonfrate et al. describe optical parametric oscillators useful for the study of quantum interference and quantum cryptography, and for metrology applications in *Parametric Fluorescence in Periodically Poled Silica Fibers*, Applied Physics Letters, Vol. 75, No. 16, 1999, pages 2356-2358, which is incorporated in its entirety by reference herein. Second-order susceptibility can be induced in a several-microns-thick region of fused silica (a material that is not normally centro-symmetric, and therefore normally does not exhibit a second-order susceptibility) by poling at elevated temperatures. This phenomenon has been described by R. A. Myers et al. in *Large Second-Order Nonlinearity in Poled Fused Silica*, Optics Letters, Vol. 16, No. 22, 1991, pages 1732-1734, which is incorporated in its entirety by reference herein.

FIGS. 1A and 1B schematically illustrate the poling of a silica wafer 1. As schematically illustrated in FIG. 1A, poling typically comprises using an anode electrode 2 placed proximate to one surface 3 of the wafer 1 and a cathode electrode 4 placed proximate to the opposite surface 5 of the wafer 1. A voltage is applied across the wafer 1 for a period of time, resulting in a second-order optical nonlinearity profile. The profile has a thickness and is localized beneath the surface 3 where the anode electrode was placed, as schematically illustrated in FIG. 1B. As used herein, the term "anodic surface" refers to the surface which is placed proximate to the anode electrode, and the term "cathodic surface" refers to the surface which is placed proximate to the cathode electrode. Such a poling procedure is described in more detail by Thomas G. Alley et al. in *Space Charge Dynamics in Thermally Poled Fused Silica*, Journal of Non-Crystalline Solids, Vol. 242, 1998, pages 165-176, which is incorporated herein in its entirety.

The field of poled silica has suffered from the lack of a common method to reliably measure the second-order optical nonlinearity profile of poled samples. This absence of a reliable procedure for measuring nonlinearity profiles may be the reason, at least in part, for wide discrepancies in the measured magnitudes and the positions of the nonlinearity profiles of various poled systems as reported in the literature. The Maker fringe (MF) technique is the most common method currently used to investigate the nonlinearity profile of poled silica. The MF technique comprises focusing a pulsed laser beam of intensity $I_1$ (known as the fundamental signal) onto a sample at an incident angle $\theta$ and measuring the intensity $I_2$ of the second harmonic (SH) signal generated within the nonlinear region as a function of the incident angle $\theta$. For a transverse magnetic (TM) polarized fundamental laser beam, the conversion efficiency $\eta_{TM}(\theta)$ is given by:

$$\eta_{TM}(\theta) = \frac{I_2}{I_1} = f(\theta, n_1, n_2) \left| \int d_{33}(z) e^{j\Delta k(\theta) z} dz \right|^2 \tag{1}$$

where $d_{33}(z)$ is the nonlinear coefficient (which is proportional to the second-order susceptibility $\chi^{(2)}$);

$z$ is the direction normal to the sample surface (i.e., parallel to the poling field);

$n_1$ and $n_2$ are the refractive indices at the fundamental and SH frequencies, respectively;

$\Delta k = k_2 - 2k_1$, where $k_1$ and $k_2$ are the fundamental and SH wave numbers, respectively, and $f(\theta, n_1, n_2)$ is a well-defined function of the incident angle $\theta$ (relative to the surface normal direction) and refractive indices $n_1$ and $n_2$.

The function $f(\theta, n_1, n_2)$ accounts for both the power loss due to reflection suffered by the fundamental and the SH beams, and the projection of the input electric field along the appropriate direction. In general, $f(\theta, n_1, n_2)$ depends on both the polarization of the input fundamental wave and the geometry of the second harmonic generation configuration. The exact formula of $f(\theta, n_1, n_2)$ is given by D. Pureur, et al. in *Absolute Measurement of the Second-Order Nonlinearity Profile in Poled Silica*, Optics Letters, Vol. 23, 1998, pages 588-590, which is incorporated in its entirety by reference herein. This phenomenon is also described by P. D. Maker et al. in *Effects of Dispersion and Focusing on the Production of Optical Harmonics*, Physics Review Letters, Vol. 8, No. 1, 1962, pages 21-22, which is incorporated in its entirety by reference herein.

The conversion efficiency $\eta_{TM}(\theta)$ is obtained experimentally by rotating the sample with respect to the incident laser beam and measuring the power of the SH signal as a function of the incident angle $\theta$. Due to dispersion of the laser beam, $\Delta k$ is finite and $\eta_{TM}(\theta)$ exhibits oscillations (called the Maker fringes) which pass through several maxima and minima. The objective of this measurement is to retrieve the second-order nonlinearity profile $d_{33}(z)$. The absolute value of the integral in Equation 1 is the amplitude of the Fourier transform of $d_{33}(z)$. In principle, if both the amplitude and the phase of a Fourier transform are known, the argument of the Fourier transform (in this case $d_{33}(z)$) can be readily inferred by taking the inverse Fourier transform of the Fourier transform. However, the measured Maker fringes provide only the magnitude of the Fourier transform, not its phase. Consequently, for an arbitrary and unknown nonlinearity profile, the MF measurement alone is not sufficient to determine a unique solution for $d_{33}(z)$. Even if the phase information were available, the shape of $d_{33}(z)$ could be determined, but the location of this shape beneath the surface of the sample (i.e., where the nonlinearity profile starts beneath the surface) could not be determined.

Previous efforts to determine $d_{33}(z)$ have involved fitting various trial profiles to the measured MF data. Examples of such efforts are described by M. Qiu et al. in *Double Fitting of Maker Fringes to Characterize Near-Surface and Bulk Second-Order Nonlinearities in Poled Silica*, Applied Physics Letters, Vol. 76, No. 23, 2000, pages 3346-3348; Y. Quiquempois et al. in *Localisation of the Induced Second-Order Non-Linearity Within Infrasil and Suprasil Thermally Poled Glasses*, Optics Communications, Vol. 176, 2000, pages 479-487; and D. Faccio et al. in *Dynamics of the Second-Order Nonlinearity in Thermally Poled Silica Glass*, Applied Physics Letters, Vol. 79, No. 17, 2001, pages 2687-2689. These references are incorporated in their entirety by reference herein.

However, the previous methods do not produce a unique solution for $d_{33}(z)$. Two rather different trial profiles can provide almost equally good fits to the measured MF data. This aspect of using fitting routines to determine $d_{33}(z)$ is described in more detail by Alice C. Liu et al. in *Advances in the Measurement of the Poled Silica Nonlinear Profile*, SPIE Conference on Doped Fiber Devices II, Boston, Mass., November 1998, pages 115-119, which is incorporated in its entirety by reference herein.

SUMMARY OF THE INVENTION

According to one aspect of the present invention, a method measures a physical function. The method comprises forming a symmetric composite function by combining the physical function with a reference function. The method further comprises obtaining a Fourier transform of the symmetric composite function. The method further comprises calculating an inverse Fourier transform of the obtained Fourier transform. The calculated inverse Fourier transform provides information regarding the physical function.

In another aspect of the present invention, a method measures a nonlinearity profile of a sample. In accordance with the method, a sample having a sample nonlinearity profile is provided. The surface of the sample is placed in proximity to a surface of a supplemental sample to form a composite sample having a composite nonlinearity profile. The method measures a Fourier transform magnitude of composite nonlinearity profile, and calculates the sample nonlinearity profile using the Fourier transform magnitude of the composite nonlinearity profile.

In still another aspect of the present invention, a method measures a nonlinearity profile of a sample. In accordance with the method, a sample is provided that has at least one sample surface and that has a sample nonlinearity profile along a sample line through a predetermined point on the sample surface. The sample line is oriented perpendicularly to the sample surface. The method measures a Fourier transform magnitude of the sample nonlinearity profile. The method provides a reference material having at least one reference surface and having a reference nonlinearity profile along a reference line through a predetermined point on the reference surface. The reference line is oriented perpendicularly to the reference surface. The method obtains a Fourier transform magnitude of the reference nonlinearity profile. The method forms a first composite sample having a first composite nonlinearity profile by placing the sample and the reference material proximate to one another in a first configuration with the sample line substantially collinear with the reference line. The method measures a Fourier transform magnitude of the first composite nonlinearity profile. The method forms a second composite sample having a second composite nonlinearity profile which is inequivalent to the first composite nonlinearity profile by placing the sample and the reference material proximate to one another in a second configuration with the sample line substantially collinear with the reference line. The method measures a Fourier transform magnitude of the second composite nonlinearity profile. The method calculates the sample nonlinearity profile using the Fourier transform magnitudes of the sample nonlinearity profile, the reference nonlinearity profile, the first composite nonlinearity profile, and the second composite nonlinearity profile.

In still another aspect of the present invention, a method measures a nonlinearity profile of a sample. In accordance with the method, a sample is provided that has at least one sample surface and having a sample nonlinearity profile along a sample line through a predetermined point on the sample surface. The sample line is oriented perpendicularly to the sample surface. The method provides a reference material having at least one reference surface and having a reference nonlinearity profile along a reference line through a predetermined point on the reference surface. The reference line is oriented perpendicularly to the reference surface. The method forms a first composite sample having a first composite nonlinearity profile by placing the sample and the reference material proximate to one another in a first configuration with the sample line substantially collinear with the reference line. The method measures a Fourier transform magnitude of the first composite nonlinearity profile. The method forms a second composite sample having a second composite nonlinearity profile which is inequivalent to the first composite nonlinearity profile by placing the sample and the reference material proximate to one another in a second configuration with the sample line substantially collinear with the reference line. The method measures a Fourier transform magnitude of the second composite nonlinearity profile. The method calculates the sample nonlinearity profile using the Fourier transform magnitudes of the first composite nonlinearity profile and the second composite nonlinearity profile.

In still another aspect of the present invention, a method measures a sample temporal waveform of a sample optical pulse. In accordance with the method, a sample optical pulse having a sample temporal waveform is provided. The method measures a Fourier transform magnitude of the sample temporal waveform. The method provides a reference optical pulse having a reference temporal waveform. The method obtains a Fourier transform magnitude of the reference temporal waveform. The method forms a first composite optical pulse comprising the sample optical pulse followed by the reference optical pulse. The first composite optical pulse has a first composite temporal waveform. The method measures a Fourier transform magnitude of the first composite temporal waveform. The method provides a time-reversed pulse having a time-reversed temporal waveform corresponding to the reference temporal waveform after being time-reversed. The method forms a second composite optical pulse comprising the sample optical pulse followed by the time-reversed optical pulse. The method measures a Fourier transform of the second composite temporal waveform. The method calculates the sample temporal waveform using the Fourier transform magnitude of the sample temporal waveform, the Fourier transform magnitude of the reference temporal waveform, the Fourier transform magnitude of the first composite temporal waveform, and the Fourier transform magnitude of the second composite temporal waveform.

In still another aspect of the present invention, a method measures a sample temporal waveform of a sample optical pulse. In accordance with the method, a sample optical pulse having a sample temporal waveform is provided. The method provides a reference optical pulse having a reference temporal waveform. The method forms a composite optical pulse comprising the sample optical pulse followed by the reference optical pulse with a relative delay between the sample temporal waveform and the reference pulse waveform. The method measures a Fourier transform magnitude squared of the composite optical pulse. The method calculates an inverse Fourier transform of the measured Fourier transform magnitude squared. The method calculates the sample temporal waveform using the calculated inverse Fourier transform.

For purposes of summarizing the invention, certain aspects, advantages and novel features of the invention have been described herein above. It is to be understood, however, that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

FIGS. 4A-4D schematically illustrate various embodiments of the supplemental sample in accordance with embodiments of the present invention.

FIGS. 13A and 13B show arbitrarily selected nonlinearity profiles of the sample and the reference sample, respectively.

FIGS. 13C and 13D show the nonlinearity profiles of the two sandwich configurations, respectively, of the sample and reference sample of FIGS. 13A and 13B.

FIGS. 15A and 15B respectively show the original nonlinearity profiles $d_A(z)$ and $d_B(z)$ as solid curves, and show the corresponding retrieved profiles shown as crosses.

FIGS. 32A and 32B illustrate the magnitude (in units of W/m²) and phase of an arbitrary asymmetric complex envelope function to be characterized.

DETAILED DESCRIPTION OF THE PREFERRED EMBODIMENT

Figure 1A:
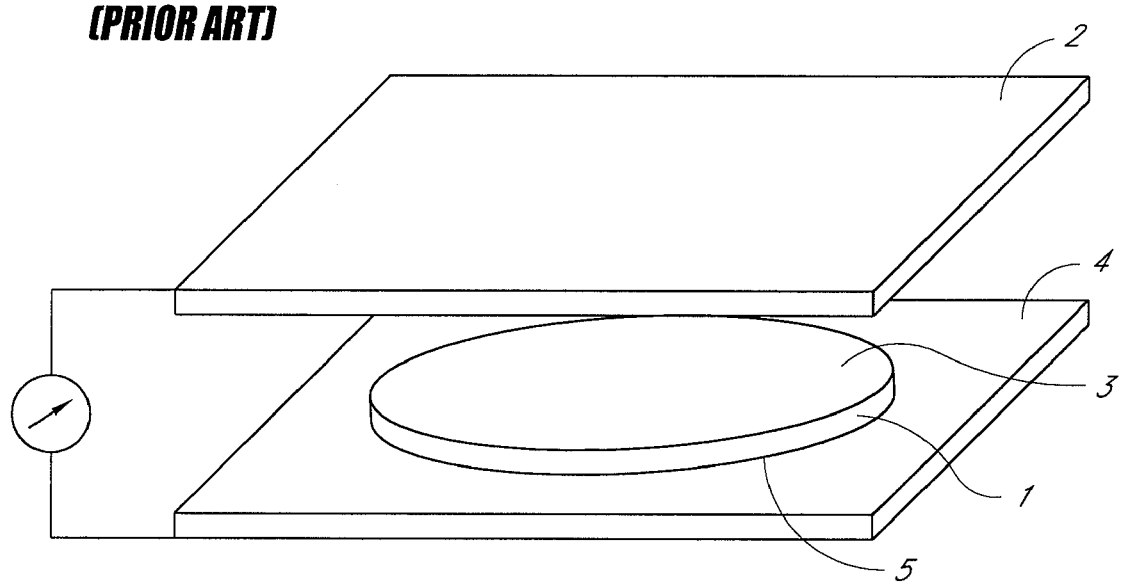
FIGS. 1A and 1B schematically illustrate the poling of a silica wafer.
Figure 1B:
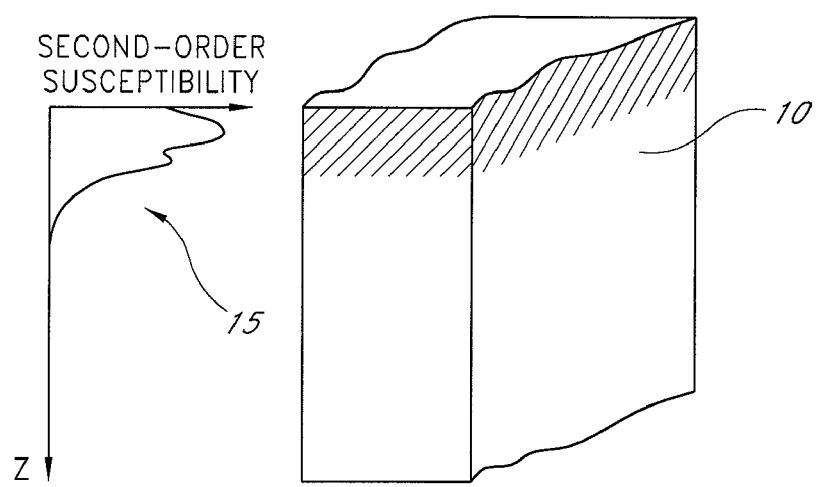
Figure 2:
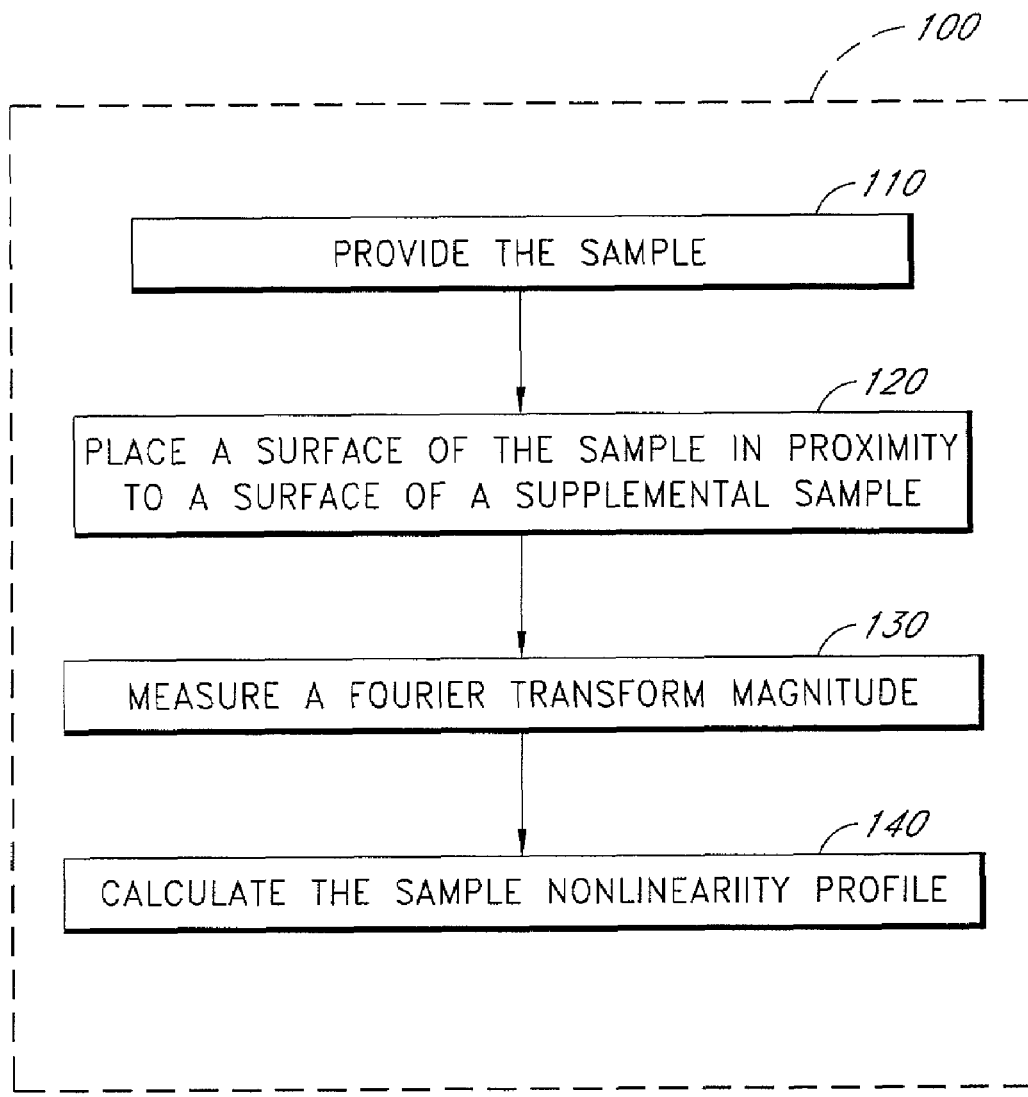
FIG. 2 is a flow diagram of a method of measuring a second-order optical nonlinearity profile of a sample in accordance with embodiments of the present invention.

FIG. 2 is a flow diagram of a method 100 of measuring a second-order optical nonlinearity profile of a sample 10 of FIG. 1B in accordance with embodiments of the present invention. While the flow diagrams herein illustrate particular embodiments with steps in a particular order, other embodiments with different orders of steps are also compatible with the present invention.

Figure 3A:
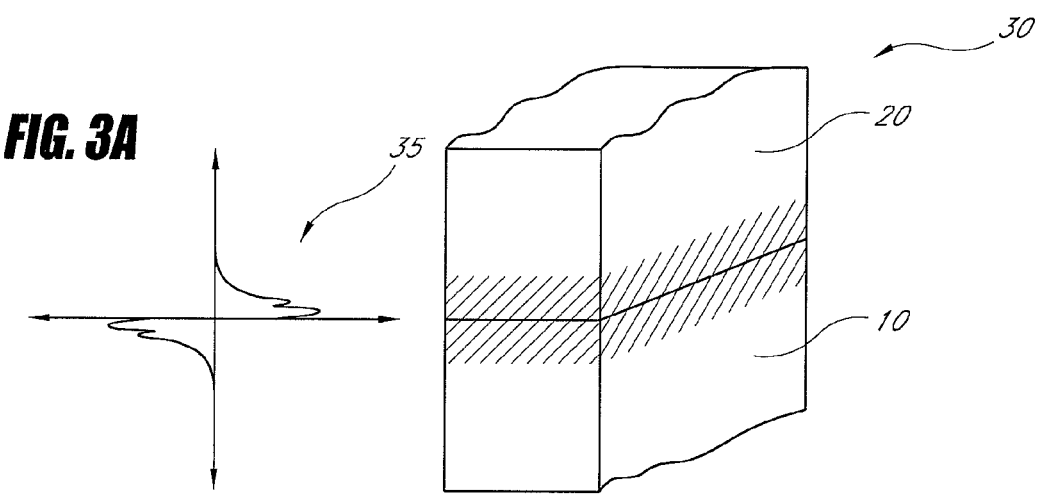
FIG. 3A schematically illustrates a composite sample having an odd second-order optical nonlinearity profile.

In the method 100, the sample 10 is provided in an operational block 110. The sample 10 has the second-order optical nonlinearity profile 15 to be measured. In an operational block 120, a surface of the sample 10 is placed proximate to a surface of a supplemental sample 20, as schematically illustrated in FIGS. 3A-3C and 4A-4D. As schematically illustrated in FIG. 3A, the sample 10 and supplemental sample 20 form a first composite sample 30 having an odd second-order optical nonlinearity profile 35. In an operational block 130, a Fourier transform magnitude of the odd second-order optical nonlinearity profile 35 of the composite sample 30 is measured. In an operational block 140, the sample nonlinearity profile is calculated using the Fourier transform magnitude of the first composite nonlinearity profile.

In certain embodiments, calculating the sample nonlinearity profile comprises using the measured Fourier transform magnitude to determine a Fourier transform of the odd second-order optical nonlinearity profile 35 of the composite sample 30, and calculating an inverse Fourier transform of the determined Fourier transform. The calculated inverse Fourier transform provides information regarding the second-order optical nonlinearity profile 15 of the sample 10. In certain embodiments, the information comprises the magnitude and sign of the second-order optical nonlinearity profile 15 as a function of depth below the surface of the sample 10. In other embodiments, the information comprises the position of the second-order optical nonlinearity profile 15 below the surface of the sample 10.

In certain embodiments, the second-order optical nonlinearity profile 15 of the sample 10 is non-symmetric, while in other embodiments, the second-order optical nonlinearity profile 15 of the sample 10 is symmetric about the origin (e.g., odd function of z). Other existing methods are useful for measuring second-order optical nonlinearity profiles which are symmetric about the origin, but such existing methods are not compatible with non-symmetric profiles. Embodiments described herein are compatible with both symmetric and non-symmetric second-order optical nonlinearity profiles. Since it is not generally known whether the second-order optical nonlinearity profile is non-symmetric or symmetric about the origin prior to measurement, embodiments described herein provide a general method of measurement independent of the symmetry about the origin of the profile to be determined. In certain embodiments, the information comprises whether the second-order optical nonlinearity profile is symmetric or non-symmetric about the origin.

Embodiments of the present invention can be used to determine the nonlinearity profile of any optically nonlinear material (e.g., crystalline, amorphous, organic, or inorganic) in a bulk form or in a film form. In certain embodiments, the nonlinear material comprises an organic material, such as polymers and solids doped with dye molecules. In other embodiments, the nonlinear material comprises inorganic materials such as crystalline lithium niobate or amorphous materials (e.g., oxide-based, fluoride-based, or sulfide-based glasses).

In certain embodiments, the sample 10 comprises silica glass that has been poled so as to induce a second-order optical nonlinearity profile in the sample 10. For example, a fused silica wafer comprised of INFRASIL quartz glass and measuring 1"×1"×0.1" (i.e., 2.54 cm×2.54 cm×2.54 mm) can be poled at approximately 270° C. in air by using an anode electrode placed proximate to one surface of the wafer (i.e., the anodic surface) and a cathode electrode placed proximate to the opposite surface of the wafer (i.e., the cathodic surface) to apply approximately 5 kV across the wafer for approximately 15 minutes. This procedure results in a second-order optical nonlinearity profile approximately 20-30 µm thick and localized beneath the anodic surface as described in more detail by Thomas G. Alley et al. in *Space Charge Dynamics in Thermally Poled Fused Silica*, Journal of Non-Crystalline Solids, Vol. 242, 1998, pages 165-176, which is incorporated herein in its entirety. Other materials and objects (e.g., optical fibers) with inherent or induced second-order optical nonlinearity profiles, and a wide range of poling conditions, are compatible with embodiments of the present invention.

Figure 3B:
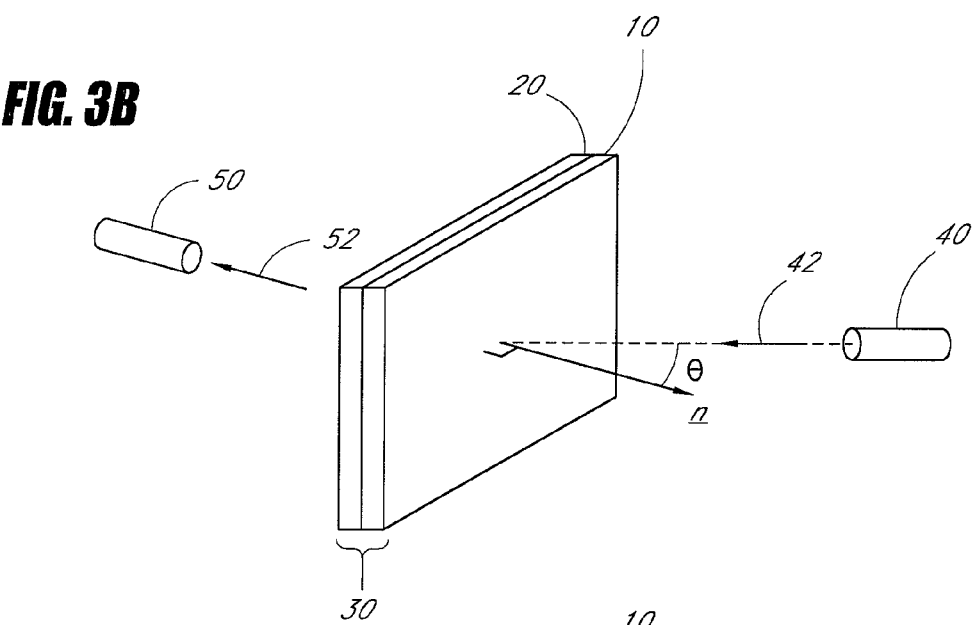
FIGS. 3B and 3C schematically illustrate two measurement configurations in accordance with embodiments of the present invention.
Figure 3C:
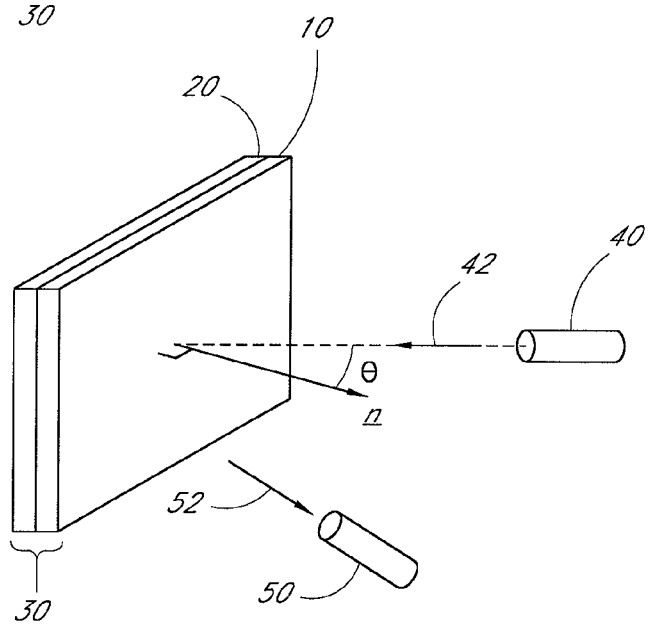

FIGS. 3B and 3C schematically illustrate two measurement configurations in accordance with embodiments of the present invention. In such embodiments, the composite sample 30 has a surface normal direction n. A laser 40 produces a laser beam 42 of light with a fundamental frequency ν. The laser beam 42 is incident on the composite sample 30 at an angle θ relative to the surface normal direction n. In the embodiment of FIG. 3B, a detector 50 is positioned on the opposite side of the composite sample 30 so as to detect the second harmonic (SH) signal 52 (having a frequency 2ν) from the composite sample 30. In certain embodiments, appropriate optical filters (not shown) are placed between the composite sample 30 and the detector 50 to reduce the laser power transmitted by the composite sample 30 to be well below the weaker power level of the SH signal. The embodiment of FIG. 3B can be considered to be a transmission configuration. In the embodiment of FIG. 3C, the detector 50 is positioned on the same side of the composite sample 30 as the laser 40 so as to detect the SH signal 52. The embodiment of FIG. 3C can be considered to be a reflection configuration. As used herein, the term "double pass" refers to configurations in which Maker fringe data are obtained from two wafers proximate to one another (e.g., as shown in FIGS. 3B and 3C). As used herein the term "single pass" refers to configurations in which Maker fringe data are obtained from a single wafer.

In certain embodiments, the composite sample 30 is positioned so that the laser beam 42 is first incident on the sample 10, while in other embodiments, the laser beam 42 is first incident on the supplemental sample 20. In certain embodiments, the SH signal 52 is measured as a function of the incident angle θ of the laser beam 42 by rotating the composite sample 30 relative to the laser beam 42.

FIGS. 4A-4D schematically illustrate various embodiments of the supplemental sample 20 in accordance with embodiments of the present invention. In certain embodiments, the supplemental sample 20 has a second-order optical nonlinearity profile substantially identical to that of the sample 10. In the embodiment schematically illustrated in FIG. 4A, the sample 10 and the supplemental sample 20 comprise two portions of a common sample 60. For example, a fused silica wafer which serves as the common sample 60 can be poled as described above, resulting in a poled region 62 beneath the anodic surface 63 of the wafer 60. The wafer can then be cut in half, producing two portions 64, 65, which can serve as the sample 10 and the supplemental sample 20. The sample 10 and the supplemental sample 20 can then be placed proximate to one another, thereby forming the composite sample 30.

By flipping the supplemental sample 20 180° to form the composite sample 30, the second-order optical nonlinearity profile of the supplemental sample 20 is effectively multiplied by −1. The physical reason for this sign change is that during poling, the symmetry of the intrinsic material is broken along the z direction. Thus, the second-order optical nonlinearity profile of the composite sample 30 is an odd function. In certain embodiments, the sample 10 and the supplemental sample 20 are placed proximate to one another with the poled regions of the portions 64, 65 proximate to one another (referred to herein as an anode-to-anode configuration). In certain such embodiments, the two halves of the surface 63 are in contact with one another, while in other embodiments, there is empty space or a spacer material between the two portions 64, 65. This spacer material can comprise an index-matching gel which reduces total internal reflection. In other embodiments, the sample 10 and the supplemental sample 20 are placed proximate to one another with the poled regions of the portions 64, 65 on the outer sides of the composite sample 30 (referred to herein as a cathode-to-cathode configuration). In certain such embodiments, the two portions 64, 65 are in contact with one another, while in other embodiments, there is empty space or a spacer material (e.g., index-matching gel) between the two portions 64, 65.

In the embodiment schematically illustrated in FIG. 4B, the supplemental sample 20 is prepared using substantially identical conditions as those used to prepare the sample 10. For example, two substantially identical fused silica wafers 70, 74 can be poled sequentially or simultaneously as described above using substantially identical conditions, resulting in corresponding poled regions 71, 75 beneath corresponding surfaces 72, 76. In this way, one wafer 70 serves as the sample 10, and the other wafer 74 serves as the supplemental sample 20. The sample 10 and the supplemental sample 20 can then be placed proximate to one another, thereby forming the composite sample 30. In certain embodiments, the sample 10 and the supplemental sample 20 are placed proximate to one another with the poled regions 71, 75 proximate to one another in the anode-to-anode configuration. In certain such embodiments, the two surfaces 72, 76 are in contact with one another, while in other embodiments, there is empty space or a spacer material (e.g., index-matching gel), between the two wafers 70, 74. In other embodiments, the sample 10 and the supplemental sample 20 are placed proximate to one another with the poled regions 71, 75 on opposite sides of the composite sample 30 in the cathode-to-cathode configuration. In certain such embodiments, the two wafers 70, 74 are in contact with one another, while in other embodiments, there is empty space or a spacer material (e.g., index-matching gel) between the two wafers 70, 74.

In the embodiment schematically illustrated in FIG. 4C, the supplemental sample 20 comprises a reflector 80 with a reflecting surface 81. The sample 10 of such embodiments can comprise a wafer 82 with a poled region 83 beneath a surface 84 of the wafer 82. The sample 10 and the supplemental sample 20 can then be placed proximate to one another, thereby forming the composite sample 30. In certain embodiments, the sample 10 and the supplemental sample 20 are placed proximate to one another with the poled region 83 proximate to the reflecting surface 81. In certain such embodiments, the reflecting surface 81 and the surface 84 are in contact with one another, while other embodiments have an empty space or a spacer material between the two surfaces 81, 84. When detecting the SH signal 52 in the reflection configuration, the reflector 80 of such embodiments provides an image of the second-order nonlinearity profile of the sample 10 substantially identical to the second-order nonlinearity profile of the sample 10.

In alternative embodiments, as schematically illustrated in FIG. 4D, the supplemental sample 20 and the poled sample 82 are placed proximate to one another with the reflecting surface 81 placed against the sample surface 85 on the opposite side of the sample 10 from the surface 84. In certain such embodiments, the two surfaces 81, 85 are in contact with one another, while in other embodiments, there is empty space or a spacer material between the two surfaces 81, 85.

In certain embodiments, placing the sample 10 and the supplemental sample 20 proximate to one another comprises sandwiching the sample 10 and the supplemental sample 20 together. In certain such embodiments, the sample 10 and the supplemental sample 20 are clamped together, while in other embodiments, the sample 10 and the supplemental sample 20 are glued together. Other methods of placing the sample 10 proximate to the supplemental sample 20 are compatible with embodiments of the present invention.

Figure 5:
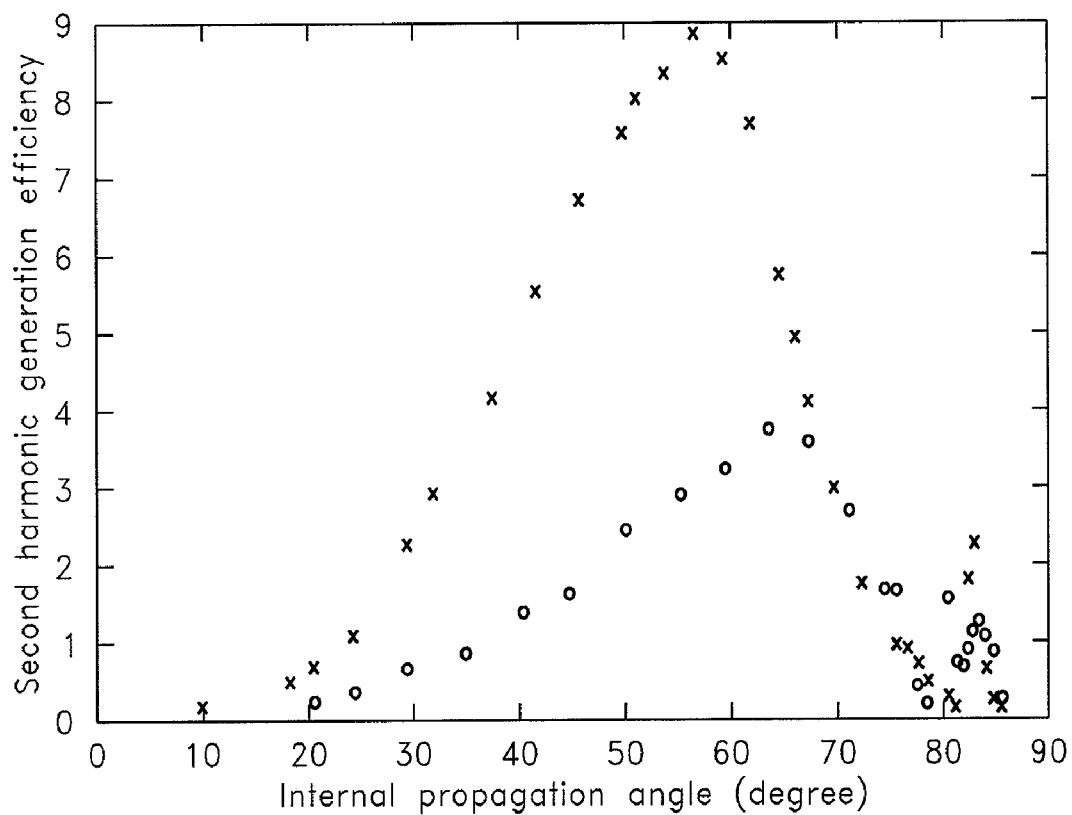
FIG. 5 illustrates exemplary Maker fringe (MF) profiles (in units of $10^{-19}$ $m^2/W$) measured from a common sample (shown as open circles) and a composite sample (shown as crosses).

FIG. 5 illustrates exemplary Maker fringe profiles measured from a common sample 60 (shown as open circles) and from a composite sample 30 (shown as crosses). As described above, the measured fringe profile corresponds to the Fourier transform magnitude of the second-order optical nonlinearity profile of the composite sample 30. In certain embodiments, measuring the Fourier transform magnitude comprises measuring the Maker fringe profile of the composite sample 30. The composite sample 30 was formed by cutting the common sample 60 in half and placing the two halves proximate to one another with the surfaces near the poled regions in contact with one another. The fringe profile of the composite sample 30 is more intense and is shifted towards lower angles than that of the common sample 60 because the nonlinear region of the composite sample 30 is twice as thick as the nonlinear region of the common sample 60.

Figure 6:
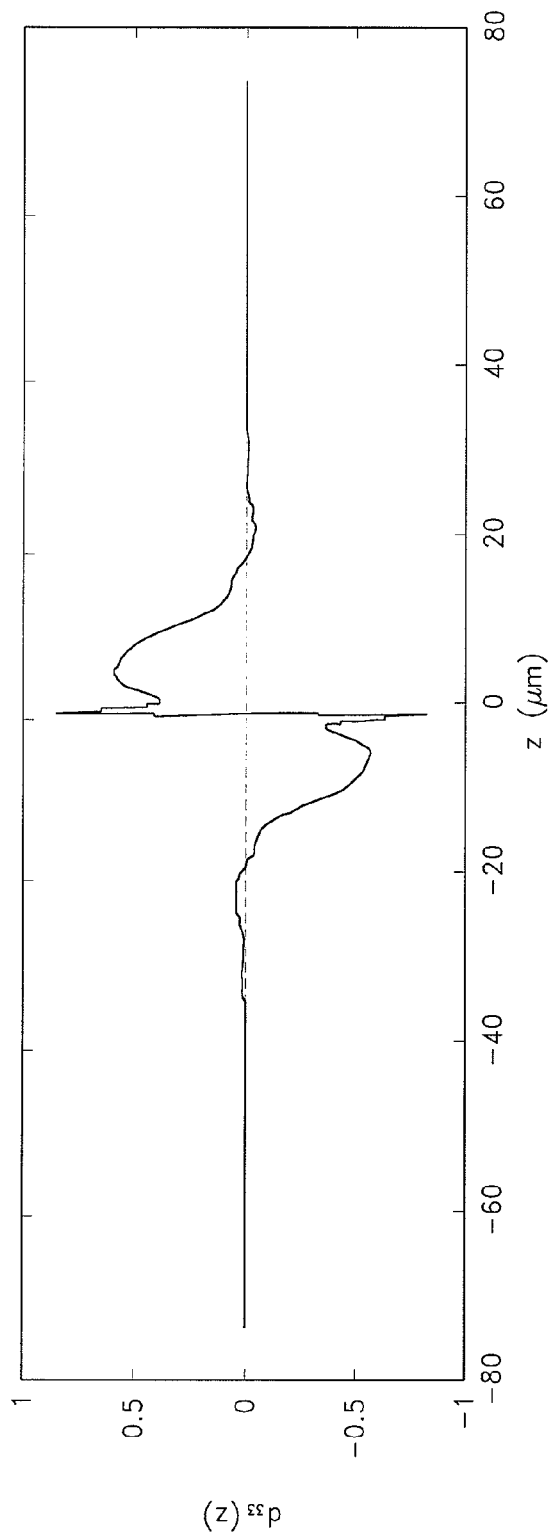
FIG. 6 illustrates the second-order nonlinearity profile $d_{33}(z)$ (in units of $10^{-12}$ m/V) of the composite sample obtained by calculating the inverse Fourier transform of the Fourier transform of the composite nonlinearity profile.
Figure 7:
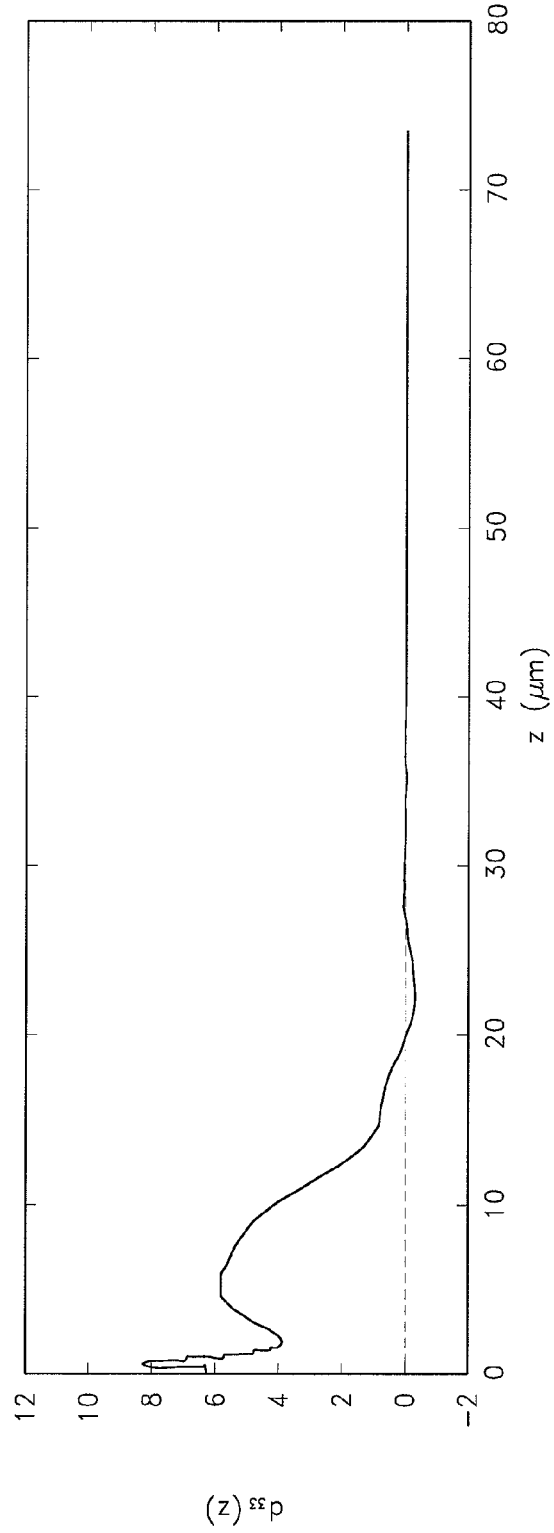
FIG. 7 illustrates the original nonlinearity profile $d_{33}(z)$ (in units of $10^{-13}$ m/V) of the sample corresponding to the z>0 portion of the nonlinearity profile of FIG. 6.

FIG. 6 illustrates the second-order nonlinearity profile $d_{33}(z)$ of the composite sample 30 obtained by calculating the inverse Fourier transform of the Fourier transform calculated using the measured fringe profile from the composite sample 30 as illustrated in FIG. 5. The abscissa $z=0$ corresponds to the boundary between the mated surfaces of the sandwiched sample 10 and the supplemental sample 20. By construction, the nonlinearity profile of the composite sample 30 is the juxtaposition of the $d_{33}(z)$ profile of the sample 10 and its mirror image with respect to the origin, i.e., $-d_{33}(-z)$, from the supplemental sample 20. By retaining only the $z>0$ portion of the nonlinearity profile of FIG. 6, the original nonlinearity profile $d_{33}(z)$ of the sample 10 is directly obtained, as illustrated in FIG. 7. The nonlinearity profile of FIG. 7 represents an unambiguously derived nonlinearity profile of the thermally poled silica sample 10. The need for the phase information has been eliminated by artificially creating an odd nonlinearity profile based on the nonlinearity profile of the sample 10.

FIG. 7 also includes information regarding the depth location of the nonlinearity, which would not be available using prior methods, even if the phase information was retrieved. FIG. 7 shows that $d_{33}(z)$ changes sign and that its peak value is approximately 0.8 picometer per volt (pm/V=$10^{-12}$ m/V). This result is the highest reliable value of $d_{33}(z)$ reported for thermally poled silica. The peak of the nonlinearity profile is located approximately one micron under the anode surface, and the poled region extends approximately 35 microns under the surface.

The main mechanism believed to be responsible for the second-order optical susceptibility $\chi^{(2)}$ in thermally poled silica is DC rectification of the third-order optical susceptibility $\chi^{(3)}$ of silica. As described more fully by D. Faccio et al. and T. G. Alley et al. (cited above), the second-order susceptibility $\chi^{(2)}$ is proportional to $\chi^{(3)}E(z)$, where $E(z)$ is the permanent electric field that develops inside the glass during poling.

The charge distribution within the glass which generates the permanent electric field $E(z)$ can be determined from the nonlinearity profile $d_{33}(z)$. Decomposing the poled region into essentially thin infinite planes, the electric field $E(z)$ is related to the charge density $\rho(z)$ by the one-dimensional form of Maxwell's equation, $\delta E/\delta z = \rho(z)/\epsilon$, where $\epsilon$ is the dielectric susceptibility of the medium. Since $d_{33}(z)$ is proportional to $E(z)$, the charge distribution $\rho(z)$ can be derived by differentiating the profile $d_{33}(z)$.

Figure 8:
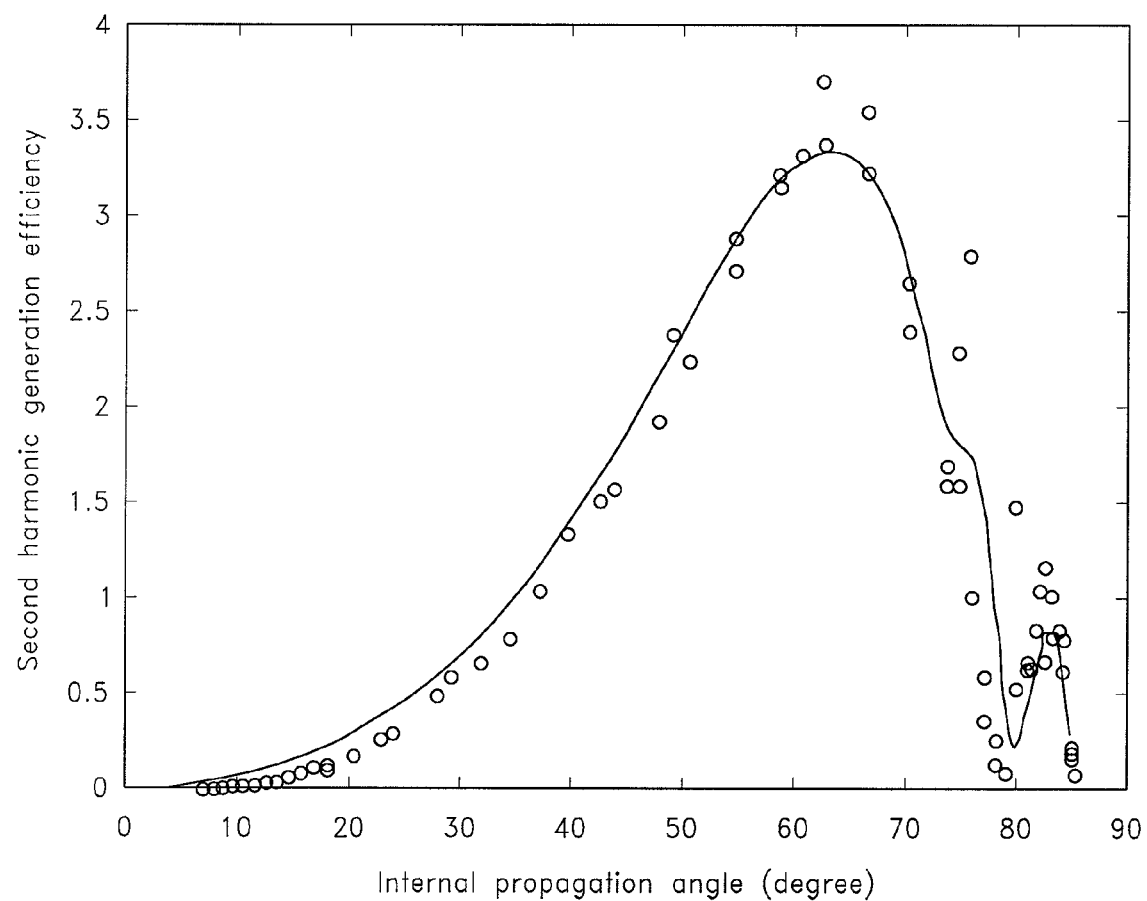
FIG. 8 illustrates the comparison of the measured fringe profile (in units of $10^{-19}$ $m^2/W$) from the original sample (open circles) with a theoretical fringe profile calculated from $d_{33}(z)$ (as shown in FIG. 7) obtained from the measured second harmonic (SH) signal from the composite sample (solid line).

The nonlinearity profile derived in accordance with embodiments of the present invention can be independently verified by comparing the measured Maker fringe profile from the original sample 10 (shown as open circles in FIG. 5 and FIG. 8) with the theoretical fringe profile (solid curve in FIG. 8) calculated from $d_{33}(z)$ obtained from the measured SH signal from the composite sample 30 (FIG. 7). This comparison, illustrated in FIG. 8, shows that the two fringe profiles agree reasonably well, and that in particular, the spatial uniformity of the second-order susceptibility of the sample 10 was sufficient to infer the nonlinearity profile reliably.

Embodiments of the present invention enable the second-order nonlinearity profile of an optically nonlinear film to be inferred unambiguously from a Maker fringe profile measurement. As described above, the nonlinearity profile of an exemplary thermally poled silica sample has been determined to: (i) have a peak value of approximately 0.8 pm/V, (ii) extend approximately 35 microns below the sample surface, and (iii) take both positive and negative values. Such magnitude and spatial information of the nonlinearity profile and of the charge distribution has significant implications in the design of future devices based on thermally poled silica.

Embodiments described above can be considered to be special cases of a more general method of determining the second-order nonlinearity profile. In the embodiments described above in which the sample 10 has been cut into two pieces which form the composite sample 30, two assumptions have been made: (1) the nonlinearity profiles of both the sample 10 and the supplemental sample 20 have the same functional dependence normal to the anode surface (i.e., $f(z)$); and (2) both the sample 10 and the supplemental sample 20 have the same nonlinear strength normal to the anode surface (i.e., $d_{33}(z)=K \cdot f(z)$, where K is the same constant for both the sample 10 and the supplemental sample 20). These assumptions in principle limit the application of above-described embodiments to nonuniform poled samples.

In another embodiment, the nonlinearity profile of a sample is uniquely determined without either of the two assumptions described above. In addition, the sample 10 need not be cut into two pieces to determine the nonlinearity profile.

Figure 9:
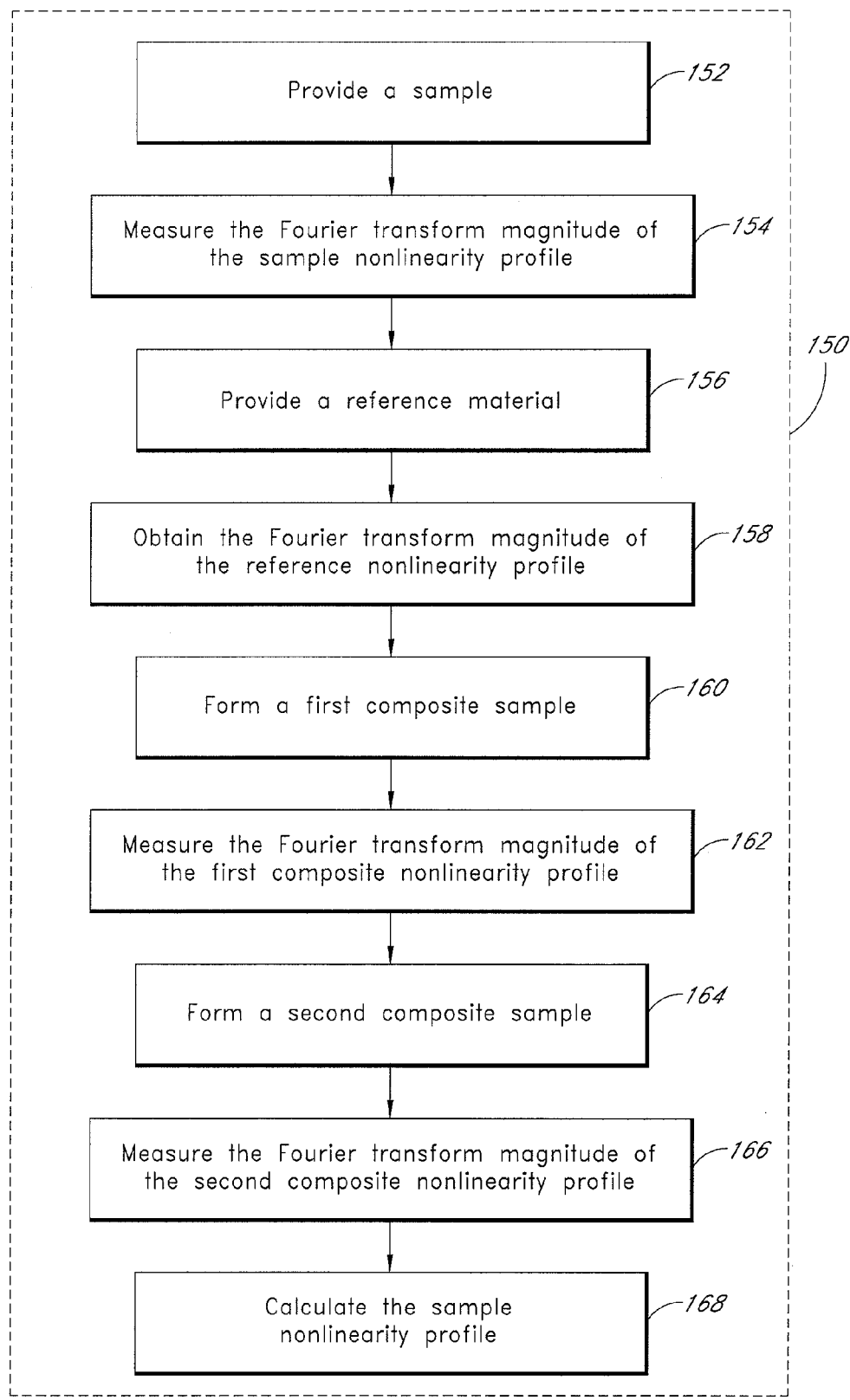
FIG. 9 is a flow diagram of a method of measuring a sample nonlinearity profile in accordance with embodiments of the present invention.

FIG. 9 is a flow diagram of a method 150 of measuring a sample nonlinearity profile 15 of a sample 10. In an operational block 152, a sample 10 having at least one sample surface and having a sample nonlinearity profile 15 along a sample line through a predetermined point on the sample surface is provided. The sample line is oriented perpendicularly to the sample surface. In an operational block 154, a Fourier transform magnitude of the sample nonlinearity profile 15 is measured. In an operational block 156, a reference material having at least one reference surface and having a reference nonlinearity profile along a reference line through a predetermined point on the reference surface is provided. The reference line is oriented perpendicularly to the reference surface. In an operational block 158, a Fourier transform magnitude of the reference nonlinearity profile is obtained. In an operational block 160, a first composite sample having a first composite nonlinearity profile is formed. The first composite sample is formed by placing the sample 10 and the reference material proximate to one another in a first configuration with the sample line substantially collinear with the reference line. In an operational block 162, a Fourier transform magnitude of the first composite nonlinearity profile is measured. In an operational block 164, a second composite sample having a second composite nonlinearity profile inequivalent to the first composite nonlinearity profile is formed. The second composite sample is formed by placing the sample 10 and the reference material proximate to one another in a second configuration with the sample line substantially collinear with the reference line. In an operational block 166, a Fourier transform magnitude of the second composite nonlinearity profile is measured. In an operational block 168, the sample nonlinearity profile 15 is calculated using the Fourier transform magnitudes of the sample nonlinearity profile, the reference nonlinearity profile, the first composite nonlinearity profile, and the second composite nonlinearity profile.

Figure 10A:
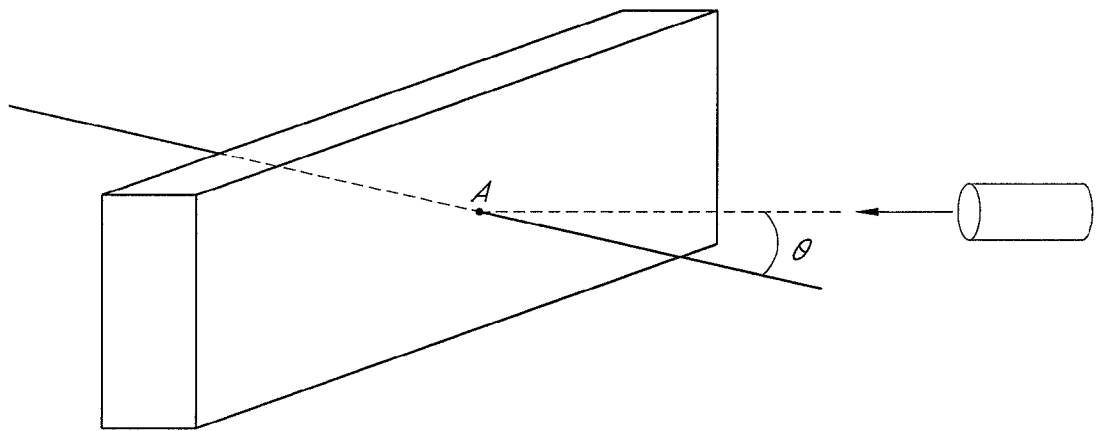
FIGS. 10A and 10B schematically illustrate single-pass configurations for measuring the Fourier transform magnitudes of the sample nonlinearity profile and the reference nonlinearity profile, respectively.
Figure 10B:
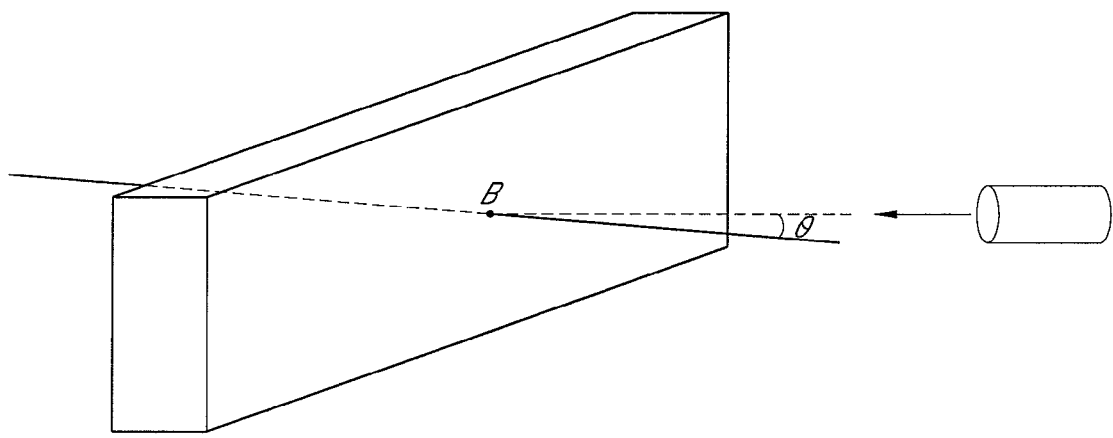

In certain embodiments, the Fourier transform magnitude of the sample nonlinearity profile is measured in the operational block 154 by measuring the Maker fringe (MF) data of the sample in a single-pass configuration as schematically illustrated by FIG. 10A. The MF data of the sample ($MF_1$) is thus representative of the Fourier transform magnitude of the sample nonlinearity profile along a sample line through a predetermined point (labelled "A" in FIG. 10A) on the sample surface. The sample line is oriented perpendicularly to the sample surface. Similarly, as schematically illustrated in FIG. 10B, the Fourier transform magnitude of the reference nonlinearity profile can be measured by measuring the MF data of the reference material in a single-pass configuration. The MF data of the reference material ($MF_2$) is thus representative of the Fourier transform magnitude of the reference nonlinearity profile along a reference line through a predetermined point (labelled "B" in FIG. 10B) on the reference surface. As used below, the MF data of the sample is expressed as:

$$MF_1(f) = |D_A(f)|^2 \quad (2)$$

and the MF data of the reference sample is expressed as:

$$MF_2(f) = |D_B(f)|^2 \quad (3)$$

where the Fourier transform of the sample nonlinearity profile $d_A(z)$ is denoted by $$d_A(z) \xrightarrow{FT} D_A(f) = |D_A(f)|e^{j\phi_A(f)},$$

the Fourier transform of the reference nonlinearity profile $d_B(z)$ is denoted by $$d_B(z) \xrightarrow{FT} D_B(f) = |D_B(f)|e^{j\phi_B(f)},$$

and $f$ is the spatial frequency. The spatial frequency $f$ is given by $$f = \pm \left| 2 \frac{n_1 \cos\theta_\omega - n_2 \cos\theta_{2\omega}}{\lambda} \right|,$$

where $\lambda$ is the fundamental wavelength, and $n_1$, $n_2$, $\theta_\omega$, and $\theta_{2\omega}$ are the refractive indices and internal propagation angles at the fundamental and second harmonic wavelengths, respectively.

In general, $d_A(z)$ does not equal $d_B(z)$. For both $d_A(z)$ and $d_B(z)$, the poled region is assumed to be in the $z \leq 0$ half of the z-coordinate system where z=0 defines the anodic surfaces. This choice of coordinate system ensures that for z>0, $d_A(z) = d_B(z) = 0$. In addition, the depth of the poled region at the sample surface is $W_A$ such that $d_A(z) = 0$ for $z < -W_A$, and the depth of the poled region at the reference surface is $W_B$ such that $d_B(z) = 0$ for $z < -W_B$.

Figure 11A:
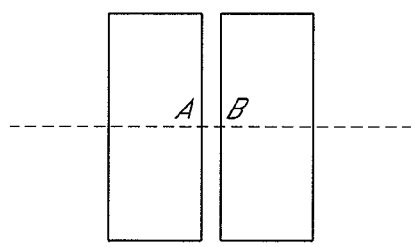
FIGS. 11A-11D schematically illustrate various configurations for forming composite samples in accordance with embodiments of the present invention.
Figure 11B:
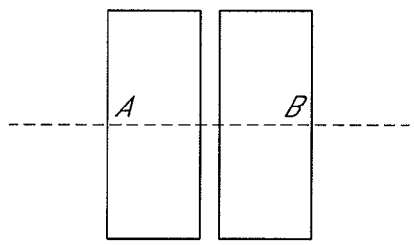
Figure 11C:
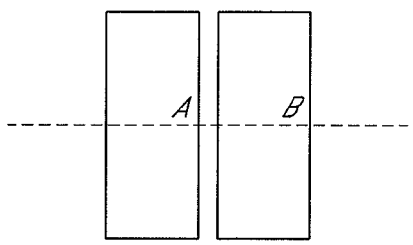
Figure 11D:
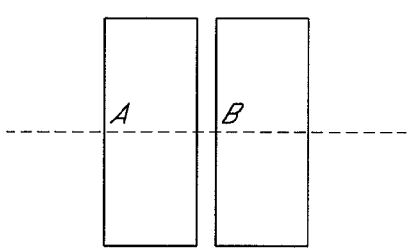

FIGS. 11A-11D schematically illustrate various configurations for forming composite samples in accordance with embodiments of the present invention. Each of the composite samples of FIGS. 11A-11D has a corresponding composite nonlinearity profile. In FIG. 11A, the composite sample is formed by placing the anodic surface of the sample and the anodic surface of the reference material proximate to one another, and is referred to herein as an anode-to-anode configuration. In FIG. 11B, the composite sample is formed by placing the cathodic surface of the sample and the cathodic surface of the reference material proximate to one another, and is referred to herein as a cathode-to-cathode configuration. In FIG. 11C, the composite sample is formed by placing the anodic surface of the sample and the cathodic surface of the reference material proximate to one another, and is referred to herein as an anode-to-cathode configuration. In FIG. 11D, the composite sample is formed by placing the cathodic surface of the sample and the anodic surface of the reference material proximate to one another, and is referred to herein as a cathode-to-anode configuration.

In certain embodiments, the Fourier transform magnitude of the first composite nonlinearity profile is measured in the operational block 162 (FIG. 9) by measuring the MF data of the first composite sample in a double-pass configuration. In embodiments in which the first composite sample has a first configuration as schematically illustrated by one of FIGS. 11A-11D, the MF data of the first composite sample is thus representative of the Fourier transform magnitude of the first composite nonlinearity profile along the dashed line of the corresponding one of FIGS. 11A-11D.

In certain embodiments, the Fourier transform magnitude of the second composite nonlinearity profile is measured in the operational block 166 (FIG. 9) by measuring the MF data of the second composite sample in a double-pass configuration. The configuration of the second composite sample is chosen to provide a second composite nonlinearity profile inequivalent to the first composite nonlinearity profile. For example, if the first configuration of the first composite sample is that of FIG. 11A or FIG. 11B, then the second configuration of the second composite sample can be that of FIG. 11C or FIG. 11D. Similarly, if the first configuration of the first composite sample is that of FIG. 11C or FIG. 11D, then the second configuration of the second composite sample can be that of FIG. 11A or FIG. 11B. The MF data of the second composite sample is thus representative of the Fourier transform magnitude of the second composite nonlinearity profile along the dashed line of the corresponding one of FIGS. 11A-11D.

The MF data of the anode-to-anode configuration of FIG. 11A ($MF_{S1}$) contains the same information as the MF data of the cathode-to-cathode configuration of FIG. 11B ($MF_{S2}$). Similarly, the MF data of the anode-to-cathode configuration of FIG. 11C ($MF_{S3}$) contains the same information as the MF data of the cathode-to-anode configuration of FIG. 11D ($MF_{S4}$). The MF data corresponding to the four possible configurations shown in FIGS. 11A-11D can be written as:

$$MF_{S1} = |D_A|^2 + |D_B|^2 - 2|D_A||D_B|\cos(\phi_A + \phi_B) \quad (4)$$

$$MF_{S2} = |D_A|^2 + |D_B|^2 - 2|D_A||D_B|\cos(\phi_A + \phi_B + 2\phi_0) \quad (5)$$

$$MF_{S3} = |D_A|^2 + |D_B|^2 + 2|D_A||D_B|\cos(\phi_A - \phi_B + \phi_0) \quad (6)$$

$$MF_{S4} = |D_A|^2 + |D_B|^2 + 2|D_A||D_B|\cos(\phi_A - \phi_B - \phi_0) \quad (7)$$

The dependence of all these quantities on the spatial frequency has been omitted in Equations 4-7 for clarity.

From Equations 4 and 5, it can be seen that $MF_{S1}$ and $MF_{S2}$ are equivalent to one another (i.e., they have the same information in terms of $\phi_A$ and $\phi_B$). The extra modulation term $\phi_0=2\pi fL$ (where L is the sample thickness) does not contribute information regarding the nonlinearity profiles since it corresponds to a modulation term due to the summed thicknesses of the sample and reference material. In Equation 5, the factor of 2 in front of $\phi_0$ comes from the assumption that the thickness of the sample and of the reference material are the both equal to L. Similarly, $MF_{S3}$ and $MF_{S4}$ are equivalent to one another, but are inequivalent to $MF_{S1}$ and $MF_{S2}$. Thus, in certain embodiments, either $MF_{S1}$ or $MF_{S2}$ is used as a first independent source of information, and either $MF_{S3}$ or $MF_{S4}$ is used as a second independent source of information. While the description below focuses on the configurations of FIGS. 11A and 11C, in certain embodiments, one or both of these configurations can be substituted by its equivalent configuration in FIGS. 11B and 11D, respectively. For embodiments in which the sample and the reference material are spaced from one another (e.g., by an index-matching gel), Equations 4-7 can be modified to reflect the additional phase $\phi_1(f)=2\pi fL_G$ where $L_G$ is the thickness of the space between the sample and the reference material.

For configurations of FIGS. 11A and 11C, the effective nonlinearity profiles can respectively be written as $d^{S1}(z)=d_A(z)-d_B(-z)$ and $d^{S2}(z)=d_A(z)+d_B(z-L)$, where S1 and S2 respectively denote the anode-to-anode and anode-to-cathode configurations of FIGS. 11A and 11C. As used herein, the z=0 point is assumed to be at the anodic surface of the sample (i.e., at the boundary between the sample and the reference material), and L is the total thickness of the reference sample where $L \geq W_B$. Also, as used herein, the Fourier transforms of these functions are denoted as $$d^{S1}(z) \xrightarrow{FT} D^{S1}(f) \text{ and } d^{S2}(z) \xrightarrow{FT} D^{S2}(f).$$

For embodiments in which there is a space with a thickness $L_G$ between the sample and the reference material, the effective nonlinearity profiles can be respectively written as $d^{S1}(z)=d_A(z)-d_B(-z+L_G)$ and $d^{S2}(z)=d_A(z)+d_B(z-L)$, where $L=L_B+L_G$ and $L_B$ is the thickness of sample B.

The Fourier transform magnitudes of the sample nonlinearity profile, the reference nonlinearity profile, the first composite nonlinearity profile, and the second composite nonlinearity profile are used to calculate the sample nonlinearity profile in the operational block 168. The MF measurements corresponding to the two composite samples of FIGS. 11A and 11C can be expressed as:

$$MF_{S1}=|D^{S1}(f)|^2=|D_A(f)-D_B(-f)|^2= \\ |D_A(f)|e^{j\phi_A(f)}-|D_B(f)|e^{-j\phi_B(f)}|^2 \quad (8)$$

$$MF_{S2}=|D^{S2}(f)|^2=|D_A(f)+D_B(f)\cdot e^{-j2\pi fL}|^2= \\ |D_A(f)|\cdot e^{j\phi_A(f)}+|D_B(f)|\cdot e^{j[\phi_B(f)-\phi_0(f)]}|^2 \quad (9)$$

where $\phi_0(f)=2\pi fL$. Expanding the absolute value sign in Equations 8 and 9, $MF_{S1}$ and $MF_{S2}$ can be expressed as:

$$MF_{S1}=|D_A|^2+|D_B|^2-2|D_A||D_B|\cos(\phi_A+\phi_B) \quad (10)$$

$$MF_{S2}=|D_A|^2+|D_B|^2+2|D_A||D_B|\cos(\phi_A-\phi_B+\phi_0) \quad (11)$$

where the frequency dependencies of all the functions have been dropped for convenience.

In certain embodiments, once the four sets of MF data ($MF_1$, $MF_2$, $M_{S1}$ and $MF_{S2}$, given by Equations 2, 3, 10, and 11, respectively) are either measured or otherwise obtained, they can be used to express the following quantities:

$$\cos(\phi_A+\phi_B)=\frac{-MF_{S1}+MF_1+MF_2}{2\sqrt{MF_1 \cdot MF_2}}=\frac{\alpha}{\Delta} \quad (12)$$

$$\cos(\phi_A-\phi_B+\phi_0)=\frac{MF_{S2}-MF_1-MF_2}{2\sqrt{MF_1 \cdot MF_2}}=\frac{\beta}{\Delta} \quad (13)$$

Note that $\alpha$, $\beta$, and $\Delta$ are functions of frequency, $f$ and are fully determined by the MF data from the sample, reference material, and the first and second composite samples. Equations 12 and 13 can be rewritten in the following form:

$$\phi_A+\phi_B=2\pi \cdot m \pm \left|\cos^{-1}\left(\frac{\alpha}{\Delta}\right)\right| \quad (14)$$

$$\phi_A-\phi_B=2\pi \cdot n \pm \left|\cos^{-1}\left(\frac{\beta}{\Delta}\right)\right|-\phi_0 \quad (15)$$

where m and n can take any integer value $(0,\pm 1,\pm 2, \ldots)$. Note also that the output of the inverse cosine function is between 0 and $\pi$. Equations 14 and 15 can be combined to express the following quantities:

$$\phi_A+\frac{\phi_0}{2}=\pi \cdot k \pm \frac{1}{2}\left|\cos^{-1}\left(\frac{\alpha}{\Delta}\right)\right| \pm \frac{1}{2}\left|\cos^{-1}\left(\frac{\beta}{\Delta}\right)\right| \quad (16)$$

$$\phi_B-\frac{\phi_0}{2}=\pi \cdot l \pm \frac{1}{2}\left|\cos^{-1}\left(\frac{\alpha}{\Delta}\right)\right| \mp \frac{1}{2}\left|\cos^{-1}\left(\frac{\beta}{\Delta}\right)\right| \quad (17)$$

where k and l are any integers. By taking the cosine of both sides and taking their absolute values, Equations 16 and 17 can be rewritten in the following form:

$$\left|\cos\left(\phi_A+\frac{\phi_0}{2}\right)\right|=\left|\cos\left(\frac{1}{2}\left|\cos^{-1}\left(\frac{\alpha}{\Delta}\right)\right| \pm \frac{1}{2}\left|\cos^{-1}\left(\frac{\beta}{\Delta}\right)\right|\right)\right| \quad (18)$$

$$\left|\cos\left(\phi_B-\frac{\phi_0}{2}\right)\right|=\left|\cos\left(\frac{1}{2}\left|\cos^{-1}\left(\frac{\alpha}{\Delta}\right)\right| \mp \frac{1}{2}\left|\cos^{-1}\left(\frac{\beta}{\Delta}\right)\right|\right)\right| \quad (19)$$

Equations 18 and 19 provide useful information towards the calculation of the sample nonlinearity profile. Note that the right-hand sides of both Equations 18 and 19 have the same two possible values, which are given by:

$$P_1=\left|\cos\left(\frac{1}{2}\left|\cos^{-1}\left(\frac{\alpha}{\Delta}\right)\right|+\frac{1}{2}\left|\cos^{-1}\left(\frac{\beta}{\Delta}\right)\right|\right)\right| \quad (20)$$

$$P_2=\left|\cos\left(\frac{1}{2}\left|\cos^{-1}\left(\frac{\alpha}{\Delta}\right)\right|-\frac{1}{2}\left|\cos^{-1}\left(\frac{\beta}{\Delta}\right)\right|\right)\right| \quad (21)$$

where $P_1$ and $P_2$ denote these two possible values. Notice also that if $$\left|\cos\left(\phi_A+\frac{\phi_0}{2}\right)\right|=P_1, \text{ then } \left|\cos\left(\phi_B-\frac{\phi_0}{2}\right)\right|=P_2.$$

The reverse is also true, i.e., if $$\left|\cos\left(\phi_A + \frac{\phi_0}{2}\right)\right| = P_2, \text{ then } \left|\cos\left(\phi_B - \frac{\phi_0}{2}\right)\right| = P_1.$$

Using the Fourier transforms of the sample and reference material nonlinearity profiles, the following quantities can be expressed:

$$d_A\left(z + \frac{L}{2}\right) + d_A\left(-z + \frac{L}{2}\right) \xrightarrow{FT} 2|D_A|\cos\left(\phi_A + \frac{\phi_0}{2}\right) \quad (22)$$

$$d_B\left(z - \frac{L}{2}\right) + d_B\left(-z - \frac{L}{2}\right) \xrightarrow{FT} 2|D_B|\cos\left(\phi_B - \frac{\phi_0}{2}\right) \quad (23)$$

Figure 12B:
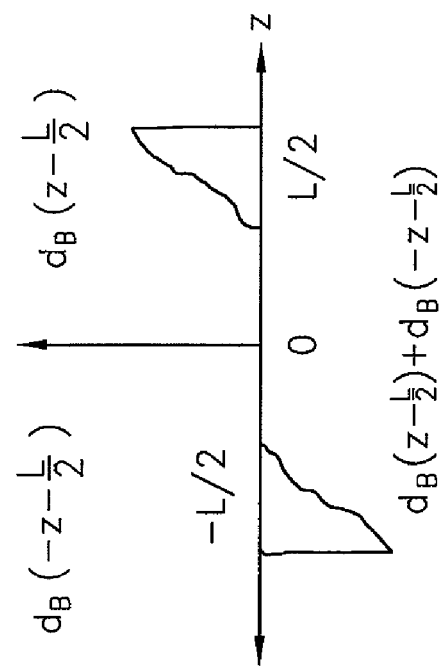
FIGS. 12A and 12B schematically illustrate two odd nonlinearity profiles for two arbitrary functions.
Figure 12A:
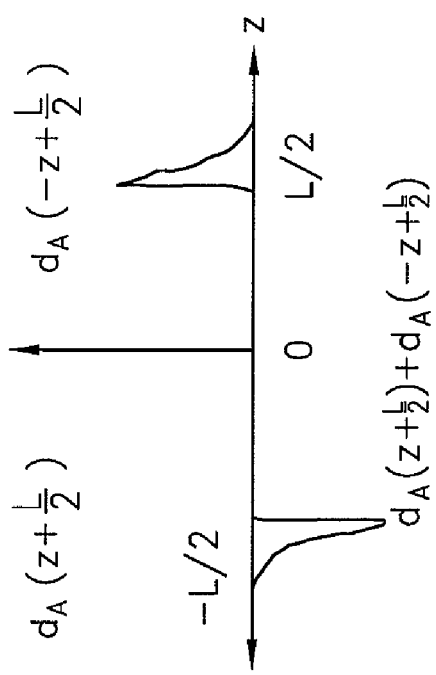

FIGS. 12A and 12B schematically illustrate two symmetric nonlinearity profiles for two arbitrary functions $d_A(z)$ and $d_B(z)$. In FIGS. 12A and 12B, the sharp boundaries at $z=\pm L/2$ correspond to the anodic surfaces of the sample and reference material. The major difference between FIGS. 12A and 12B is that the nonzero nonlinearity profile is in the $$|z| < \frac{L}{2}$$

region for $$d_B\left(z - \frac{L}{2}\right) + d_B\left(-z - \frac{L}{2}\right),$$

whereas for $$d_A\left(z + \frac{L}{2}\right) + d_A\left(-z + \frac{L}{2}\right),$$

the nonzero nonlinearity profile is in the $|k|>L/2$ region.

Equations 22 and 23 are connected to Equations 18 and 19 because of the $$\left|\cos\left(\phi_A - \frac{\phi_0}{2}\right)\right|$$

and the $$\left|\cos\left(\phi_B + \frac{\phi_0}{2}\right)\right|$$

terms. This connection can be used to remove the final ambiguity of whether $$\left|\cos\left(\phi_A - \frac{\phi_0}{2}\right)\right| = P_1 \text{ or } \left|\cos\left(\phi_A - \frac{\phi_0}{2}\right)\right| = P_2.$$

-continued

Since $d_A\left(z + \frac{L}{2}\right) + d_A\left(-z + \frac{L}{2}\right)$ is a symmetric and real function, its Fourier transform magnitude is sufficient to uniquely recover it. The same is also true for $$d_B\left(z - \frac{L}{2}\right) + d_B\left(-z - \frac{L}{2}\right),$$

which is also a symmetric and real function.

Note that for a real and symmetric function, the Hartley transform is the same as the Fourier transform. The final ambiguity can then be removed using the Hartley transform, since for a real and compact support function (i.e., one that equals zero outside a finite region), the intensity of the Hartley transform is enough to uniquely recover the original function. See, e.g., N. Nakajima in *Reconstruction of a real function from its Hartley-transform intensity*, Journal of the Optical Society of America A, Vol. 5, 1988, pages 858-863, and R. P. Millane in *Analytic Properties of the Hartley Transform and their Implications*, Proceedings of the IEEE, Vol. 82, 1994, pages 413-428, both of which are incorporated in their entirety by reference herein.

In certain embodiments, the ambiguity is removed in the following manner. If $$\left|\cos\left(\phi_A + \frac{\phi_0}{2}\right)\right| = P_1,$$

then the function $2|D_A|P_1$ is the Fourier transform magnitude of $$d_A\left(z + \frac{L}{2}\right) + d_A\left(-z + \frac{L}{2}\right)$$

(see Equation 22). For real and symmetric functions, the Hartley transform can be used to uniquely recover the original function, as described by Nakajima and by Millane, as referenced above. If the inverse Fourier transform of the Fourier transform obtained from $2|D_A|P_1$ (i.e., the Fourier transform magnitude of $$d_A\left(z + \frac{L}{2}\right) + d_A\left(-z + \frac{L}{2}\right))$$

gives the poled region in $$|z| > \frac{L}{2}, \text{ then } \left|\cos\left(\phi_A + \frac{\phi_0}{2}\right)\right| = P_1.$$

Otherwise, $$\left|\cos\left(\phi_A + \frac{\phi_0}{2}\right)\right| = P_2.$$

This result can be double-checked by computing the inverse Fourier transform of the Fourier transform obtained from $2|D_A|P_2$ and confirming that the poled region is given by $$|z| > \frac{L}{2}.$$

Note finally that the inverse Fourier transforms of both Fourier transforms obtained from the Fourier transform magnitudes $2|D_A|P_1$ and $2|D_A|P_2$ do not at the same time give a poled region in $$|z| > \frac{L}{2},$$

because either $2|D_B|P_1$ or $2|D_B|P_2$ has to yield a poled region in $$|z| < \frac{L}{2}$$

for the function $$d_B\left(z + \frac{L}{2}\right) + d_B\left(-z + \frac{L}{2}\right)$$

(see Equation 23).

In certain other embodiments, the ambiguity is removed by computing the inverse Fourier transform of the Fourier transforms obtained from both $2|D_A|P_1$ and $2|D_A|P_2$. The results should yield two symmetric functions as shown in FIGS. 12A and 12B. Taking only the z>0 portion of the resulting profiles yields two alternative profiles for $d_A(z)$. The same procedure can be applied for $d_B(z)$. By computing the theoretical MF curve of these two possible $d_A(z)$ profiles and comparing the results with the measured $MF^1(f)=|D_A(f)|^2$ data, it is straightforward to choose the correct possibility.

In an exemplary embodiment, FIGS. 13A and 13B show arbitrarily selected nonlinearity profiles of the sample and the reference sample, respectively, and FIGS. 13C and 13D show the nonlinearity profiles of the two sandwich configurations, respectively.

Figure 14B:
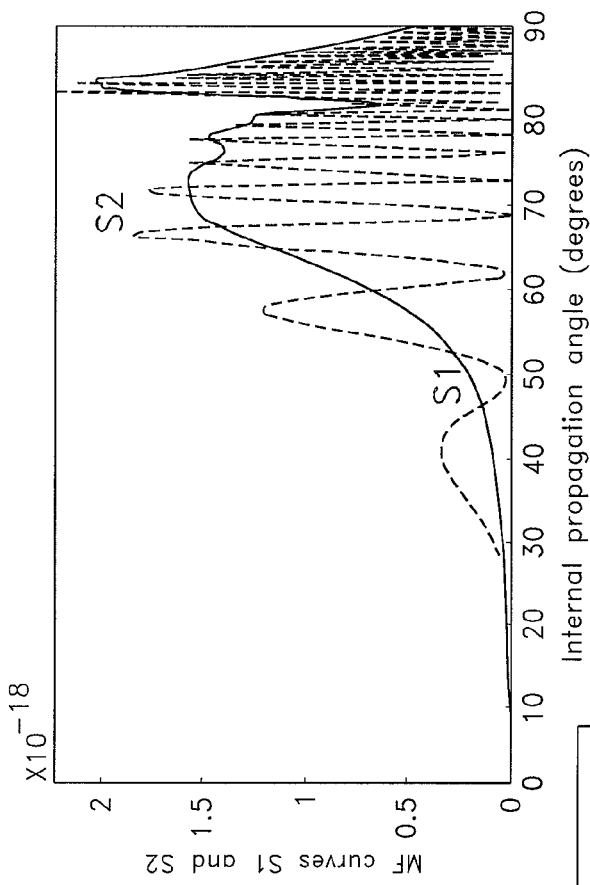
FIG. 14B shows the calculated MF curves corresponding to the double-pass configuration of the first sandwich configuration (shown as a solid line) and the second sandwich configuration (shown as a dashed line).
Figure 14A:
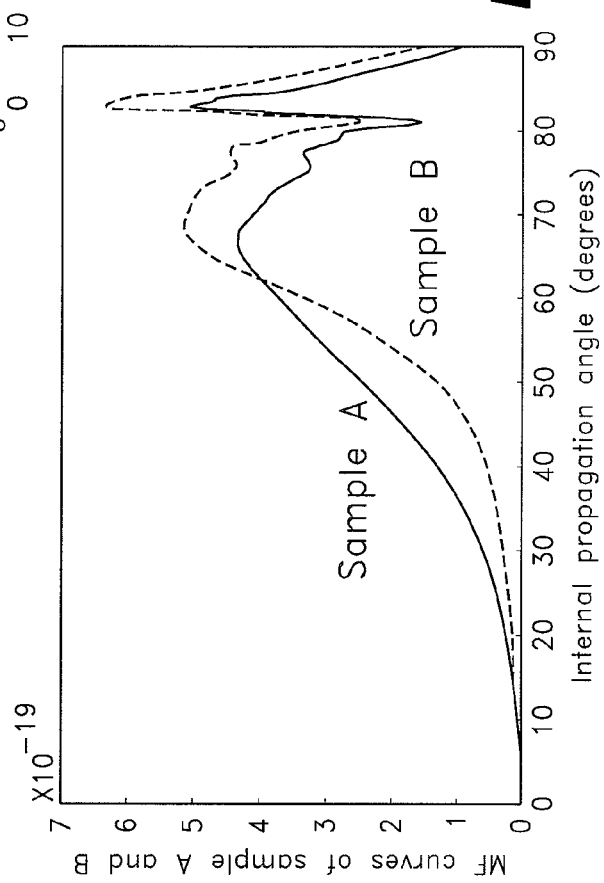
FIG. 14A shows the calculated MF curves corresponding to the single-pass configuration of the sample (shown as a solid line) and the reference sample (shown as a dashed line).

FIG. 14A shows the calculated MF curves corresponding to the single-pass configuration of the sample (shown as a solid line) and the reference sample (shown as a dashed line). FIG. 14B shows the calculated MF curves corresponding to the double-pass configuration of the first sandwich configuration (shown as a solid line) and of the second sandwich configuration (shown as a dashed line).

FIGS. 15A and 15B respectively show the original nonlinearity profiles $d_A(z)$ and $d_B(z)$ as solid curves, and show the corresponding profiles retrieved using the above-described method as crosses.

The foregoing description includes ways to uniquely recover the two arbitrary nonlinearity profiles ($d_A(z)$ and $d_B(z)$) using four sets of MF data. This result is significant since (1) the technique is applicable to even nonuniform poled samples; and (2) the sample does not need to be cut into two halves. The technique utilizes a reference material with known MF data. In certain embodiments, obtaining the MF data of the reference material comprises measuring the MF data. In other embodiments, the MF data of the reference material is previously measured and stored in memory, and obtaining the MF data comprises reading the MF data from memory. Embodiments in which the MF data is previously stored are preferable, since the number of MF measurements will be reduced from 4 to 3. Note that it is not necessary to know the reference nonlinearity profile for this technique to work, since only its corresponding MF data is used. In addition, a common reference sample can be used to characterize a plurality of samples.

In an exemplary embodiment, the sample and reference material are cut from the same poled wafer, and the MF data from the sample and reference material (given by Equations 2 and 3, respectively) are related by a constant factor (i.e., $MF_1=C\cdot MF_2$) Since points A and B are from the same poled surface, it can be assumed that:

$$d_A(z) = \sqrt{C} \cdot d_B(z) \tag{24}$$

It follows from Equation (24) that $|D_A|=\sqrt{C}\cdot|D_B|$ and $\phi_A=\phi_B$. In this exemplary embodiment, the MF data of the second composite sample ($MF_{S2}$, given by Equation 11) is not required to determine the sample nonlinearity profile. This result can be seen by inserting $\phi_A=\phi_B$ into Equation 11 and observing that all the phase information related to the sample nonlinearity profile is removed from Equation 11. Such embodiments are preferable because the mathematics of the solution is significantly more simple and is obtained with an experimental simplicity. In this preferred embodiment, the mathematical derivation stops at Equation 12, thereby avoiding the subsequent equations.

Using the fact that $|D_A|=\sqrt{C}\cdot|D_B|$ and $\phi_A=\phi_B$, Equation 12 can be rewritten as:

$$2\cdot|D_A|\cdot|\cos(\phi_A)| = \sqrt{\frac{MF_1\cdot(1+\sqrt{C})^2 - C\cdot MF_{S1}}{\sqrt{C}}} \tag{25}$$

The left-hand-side of Equation 25 is the Fourier transform magnitude of $d_A(z)+d_A(-z)$ and for such real and symmetric functions, the Fourier transform magnitude is sufficient to uniquely recover the original profile. The unique recovery of the sample nonlinearity profile $d_A(z)=\sqrt{C}\cdot d_B(z)$ is thus achieved using Equation 25. Note that embodiments in which C=1 yield the same solution as do embodiments in accordance with the method of FIG. 2. This result can be verified by putting C=1 in Equation 25. Note that for C=1, and using Equation 2, $MF_{S1}=4|D_A|^2\sin^2(\phi_A)$.

As described above, by flipping a nonlinear poled sample 180° to mate with the anode surface of another sample, the nonlinear profile of the flipped sample $d(-z)$ changes sign to $-d(z)$. Thus, the nonlinearity profile of the composite sample equals $d(z)-d(-z)$. The effect of this sign change of the flipped sample is that the nonlinearity profile of the composite sample is now an odd function, i.e., it is symmetric about the origin. For such an odd and real function, the Fourier transform is purely imaginary and odd, and the phase of the Fourier transform is equal to $\pm\pi/2$. Measurements of the MF curve of the composite sample provide the square of the Fourier transform magnitude of the nonlinearity profile $d(z)-d(-z)$, i.e., $MF_{S1}=4|D_A|^2 \sin^2(\phi_A)$. The Fourier transform of $d(z)-d(-z)$ is $2j|D_A|\sin(\phi_A)$. Therefore, the MF measurement of the composite sample is equivalent to measuring the Fourier transform magnitude of the nonlinear profile $d(z)-d(-z)$. But for real and odd functions, the Fourier transform magnitude is the same as the Hartley transform magnitude. Thus, the MF measurement provides a measurement of the Hartley transform magnitude of the real and odd function, i.e., the nonlinear profile of the composite sample $d(z)-d(-z)$. The retrieval of a real function from only its Hartley transform magnitude can be performed in various ways, as described by Nakajima and by Millane, as referenced above.

Certain embodiments described above yield the sample nonlinearity profile as well as the reference nonlinearitly profile. In such embodiments, the reference material can comprise a second sample with a second sample nonlinearity profile to be measured. Thus, the nonlinearity profiles of two samples can be measured concurrently.

In certain embodiments, the same reference material can be used for measuring the nonlinearity profiles of a plurality of samples. If the same reference material is used with different samples, the measured reference nonlinearity profile should be substantially the same from each of the measurements. Comparison of the measured reference nonlinearity profiles accompanying each of the plurality of measured sample nonlinearity profiles then provides an indication of the consistency of the measurements across the plurality of samples.

Figure 16:
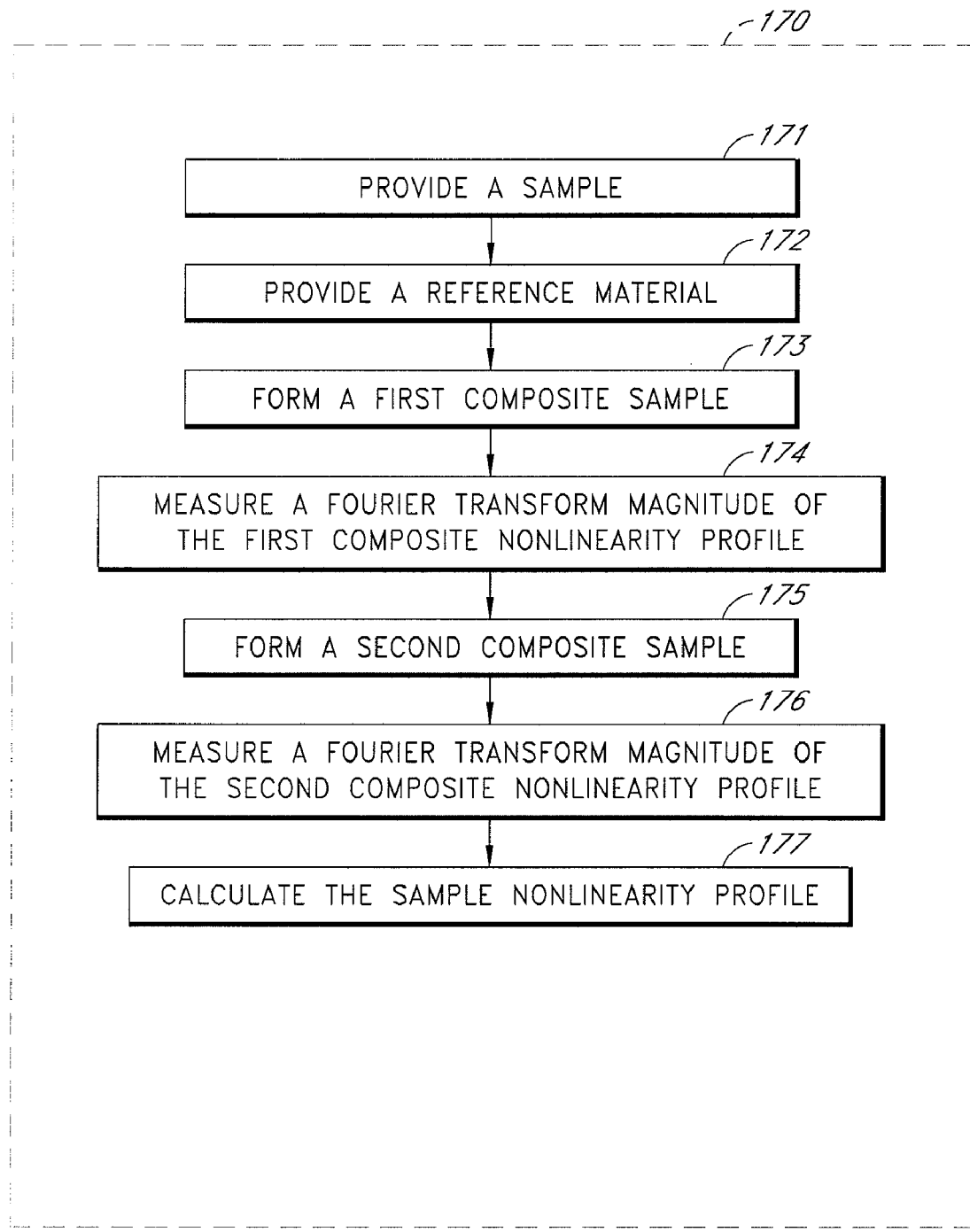
FIG. 16 is a flow diagram of one embodiment of a method of measuring a sample nonlinearity profile of a sample.

In certain embodiments, the sample nonlinearity profile can be calculated using a more generalized and flexible procedure. FIG. 16 is a flow diagram of one embodiment of a method 170 of measuring a sample nonlinearity profile 15 of a sample 10. In an operational block 171, a sample 10 having at least one sample surface and having a sample nonlinearity profile along a sample line through a predetermined point on the sample surface is provided. The sample line is oriented perpendicularly to the sample surface. In an operational block 172, a reference material having at least one reference surface and having a reference nonlinearity profile along a reference line through a predetermined point on the reference surface is provided. The reference line is oriented perpendicularly to the reference surface. In an operational block 173, a first composite sample having a first composite nonlinearity profile is formed. The first composite sample is formed by placing the sample 10 and the reference material proximate to one another in a first configuration with the sample line substantially collinear with the reference line. In an operational block 174, a Fourier transform magnitude of the first composite nonlinearity profile is measured. In an operational block 175, a second composite sample having a second composite nonlinearity profile inequivalent to the first composite nonlinearity profile is formed. The second composite sample is formed by placing the sample 10 and the reference material proximate to one another in a second configuration with the sample line substantially collinear with the reference line. In an operational block 176, a Fourier transform magnitude of the second composite nonlinearity profile is measured. In an operational block 177, the sample nonlinearity profile 15 is calculated using the Fourier transform magnitudes of the first composite nonlinearity profile and the second composite nonlinearity profile.

Figure 17:
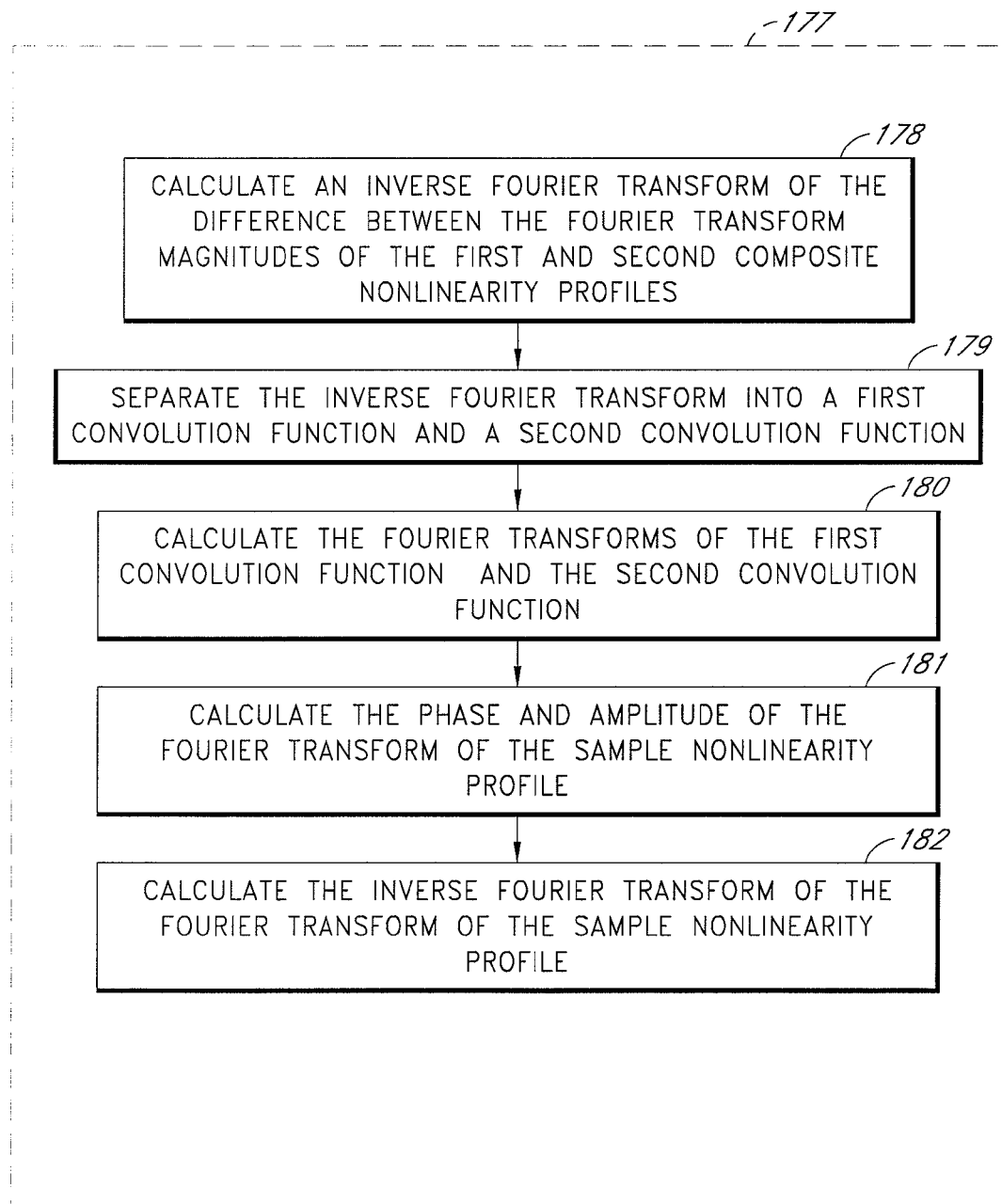
FIG. 17 is a flow diagram of one embodiment of a method for calculating the sample nonlinearity profile using the Fourier transform magnitudes of the first composite nonlinearity profile and the second composite nonlinearity profile.

FIG. 17 is a flow diagram of one embodiment of the operational block 177 for calculating the sample nonlinearity profile 15. In an operational block 178, an inverse Fourier transform of the difference between the Fourier transform magnitudes of the first and second composite nonlinearity profiles is calculated. In an operational block 179, the inverse Fourier transform is separated into a first convolution function and a second convolution function. In an operational block 180, the Fourier transform of the first convolution function and the Fourier transform of the second convolution function are calculated. In an operational block 181, the phase and amplitude of the Fourier transform of the sample nonlinearity profile are calculated using the Fourier transforms of the first and second convolution functions. In an operational block 182, the inverse Fourier transform of the Fourier transform of the sample nonlinearity profile 15 is calculated.

In certain embodiments, once the two sets of MF data ($MF_{S1}$ and $MF_{S2}$, given by Equations 10 and 11, respectively) are measured, the nonlinearity profile of the sample can be computed in the following manner. The nonlinear coefficient profiles of sample A and B are defined as $d_A(z)$ and $d_B(z)$, respectively, where z is in the direction perpendicular to the sample (see FIGS. 13A and 13B). The respective thicknesses of the nonlinear regions in samples A and B are referred to as $W_A$ and $W_B$, respectively. By definition, the nonlinear regions are confined to $z \leq 0$ (i.e., for $z>0$, $d_A(z)=d_B(z)=0$). Classical MF measurements performed on sample A and sample B alone would yield, with some known proportionality constant, the square of the Fourier transform magnitude of $d_A(z)$ and $d_B(z)$:

$$MF_A(f)=|D_A(f)|^2 \quad (26)$$

$$MF_B(f)=|D_B(f)|^2 \quad (27)$$

where $|D_A(f)|$ and $|D_B(f)|$ are the Fourier transform magnitudes of $d_A(z)$ and $d_B(z)$, respectively, $$f = \pm \left| 2\frac{n_1\cos\theta_\omega - n_2\cos\theta_{2\omega}}{\lambda} \right|$$

is the spatial frequency, where $\lambda$ is laser (fundamental) wavelength, and $n_1$, $n_2$, $\theta_\omega$, and $\theta_{2\omega}$ are the refractive indices and internal propagation angles at the fundamental and second harmonic wavelengths, respectively.

The nonlinearity profiles of S1 and S2 are $d_{S1}(z)=d_A(z)-d_B(-z+L_G)$ and $d_{S2}(z)=d_A(z)+d_B(z-L)$, respectively, where $L_G$ is the thickness of the space between sample A and sample B (which can contain an index-matching gel), $L=L_B+L_G$, and $L_B$ is the thickness of sample B. In the expression for $d_{S1}(z)$, since sample B is flipped over, its nonlinearity profile has a negative sign. The physical reason for this sign change is that during poling the symmetry of the intrinsic material is broken along the z direction.

The MF curves of S1 and S2 are proportional to the square of the FT magnitude of $d_{S1}(z)$ and $d_{S2}(z)$, respectively:

$$MF_{S1}=|D_A|^2+|D_B|^2-2|D_A||D_B|\cos(\phi_A+\phi_B+\phi_1) \quad (28)$$

$$MF_{S2}=|D_A|^2+|D_B|^2+2|D_A||D_B|\cos(\phi_A-\phi_B+\phi_2) \quad (29)$$

where $\phi_A$ and $\phi_B$ are the Fourier transform phases of $d_A(z)$ and $d_B(z)$, respectively, $\phi_1(f)=2\pi f L_G$, and $\phi_2(f)=2\pi f L$. All quantities depend on the spatial frequency, but this dependence is omitted for clarity.

The procedure to obtain the profiles $d_A(z)$ and $d_B(z)$ from the measured MF curves of S1 and S2 is as follows. The first step is to compute numerically the inverse Fourier transform of the difference $MF_{S2}-MF_{S1}$. It can be shown mathematically that the $z \leq 0$ portion of this inverse Fourier transform equals $C_1(z+L_G)+C_2(z+L)$, where $C_1(z)$ and $C_2(z)$ are the convolution functions:

$$C_1(z)=d_A(z)*d_B(z) \qquad (30)$$

$$C_2(z)=d_A(z)*d_B(-z) \qquad (31)$$

where the convolution operation is defined as:

$$f(z)*g(z)=\int f(\beta) \cdot g(z-\beta) \cdot d\beta. \qquad (32)$$

In the second step, if $L_B > 2W_B + W_A$, the functions $C_1(z+L_G)$ and $C_2(z+L)$ do not overlap in z, and both $C_1(z)$ and $C_2(z)$ are straightforward to recover individually. In the third step, the Fourier transform phases $\phi_A(f)$ and $\phi_B(f)$ are retrieved by computing the Fourier transforms of $C_1(z)$ and $C_2(z)$, which are equal to $|D_A| \cdot |D_B| \cdot e^{j[\phi_A+\phi_B]}$ and $|D_A| \cdot |D_B| \cdot e^{j[\phi_A-\phi_B]}$, respectively, then adding and subtracting the Fourier transform phases of $C_1(z)$ and $C_2(z)$. The phases $\phi_A(f)$ and $\phi_B(f)$ are then inserted into Equations 28 and 29, which are solved to obtain the Fourier transform amplitudes $|D_A|$ and $|D_B|$. The final step is to take the inverse Fourier transform of the recovered quantities $|D_A(f)|e^{j\phi_A(f)}$ and $|D_B(f)|e^{j\phi_B(f)}$ to obtain $d_A(z)$ and $d_B(z)$. Note that any error in the knowledge of L and $L_G$ translates into an error of half this magnitude in the location of the corresponding profile in the z direction, but it has no impact on the shape and magnitude of the recovered profiles.

When the nonlinear samples are thin enough, the $L_B > 2W_B + W_A$ condition stated above is not satisfied. In this case, $C_1(z)$ and $C_2(z)$ can still be recovered by using a slightly different procedure that utilizes all four MF curves ($MF_A$, $MF_B$ $MF_{S1}$, and $MF_{S2}$) The $z \leq 0$ portion of the inverse Fourier transform of $\{-MF_{S1}+MF_A+MF_B\}$ equals $C_1(z+L_G)$, and the $z \leq 0$ portion of the inverse Fourier transform of $\{MF_{S2}-MF_A-MF_B\}$ equals $C_2(z+L)$. This property is used to retrieve the convolution functions $C_1(z)$ and $C_2(z)$, and the rest of the procedure is the same as described above.

In an exemplary embodiment, two Infrasil wafers (Samples A and B, each 25 mm×25 mm×1 mm) were thermally poled under nominally identical conditions (5 kV at approximately 270° C. for 15 minutes). After poling, Sample B was polished down on its cathode side to a thickness $L_B$ of approximately 100 microns to reduce the spacing between the two nonlinear regions in the second composite sample S2, thereby reducing the frequency of oscillations at high angles in $MF_{S2}$, which would make its measurement unnecessarily difficult. For the MF measurements of Sample A, Sample B, the first composite sample, and the second composite sample, a pair of Infrasil half-cylinders were clamped on each side of the wafer to avoid total internal reflection and achieve high incidence angles.

Figure 18A:
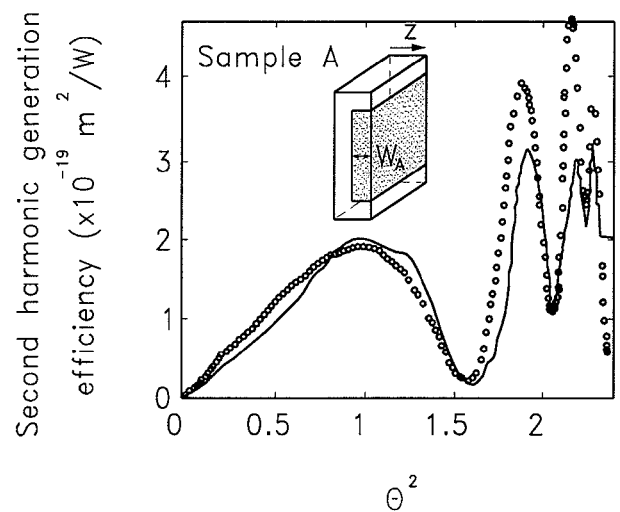
FIGS. 18A-18D illustrate measured Maker fringe data curves (open circles) and theoretical Maker fringe data curves (solid lines) from a sample, a reference sample, a first composite sample, and a second composite sample, respectively.
Figure 18B:
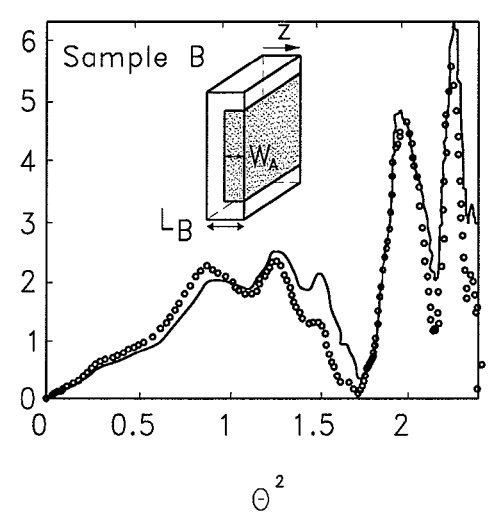
Figure 18C:
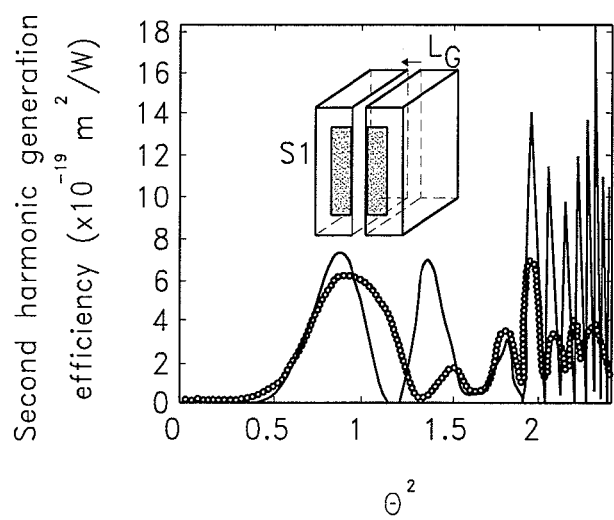
Figure 18D:
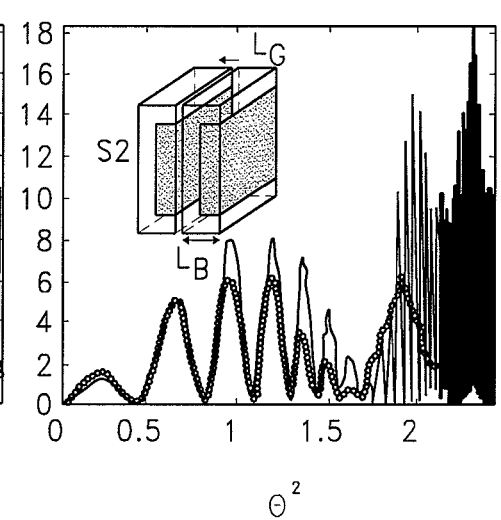

FIGS. 18A-18D illustrate the measured MF curves shown as open circles with the second harmonic generation efficiency plotted against the incidence angle squared ($\theta^2$), to better illustrate details at high angles. The insets of FIGS. 18A-18D schematically illustrate the geometry of the various samples. As illustrated by FIG. 18D, $MF_{S2}$ oscillates prominently, as expected, since the two nonlinear regions in S2 are spaced a sizable distance (L approximately equal to 140 microns). As illustrated by FIGS. 18A and 18B, the nonlinearity strength of polished Sample B is comparable to that of unpolished Sample A. This observation suggests that there is no significant induced nonlinearity in the bulk of the material or close to the cathode surface.

Processing the measured MF data from the first composite sample and the second composite sample was performed as described above for thinner samples ($L_B < W_A + 2W_B$). For each curve, the measured data points (typically approximately 300 data points) were interpolated to generate more data points and to improve the spatial resolution in the recovered profiles. With approximately $2^{15}$ data points (corresponding to a profile resolution of approximately 0.1 microns), the data processing using only the MF data from the first composite sample and the second composite sample took approximately 10 minutes on a 500-MHz computer, as compared to approximately 4 hours with other embodiments described above in relation to FIG. 9.

Figure 19:
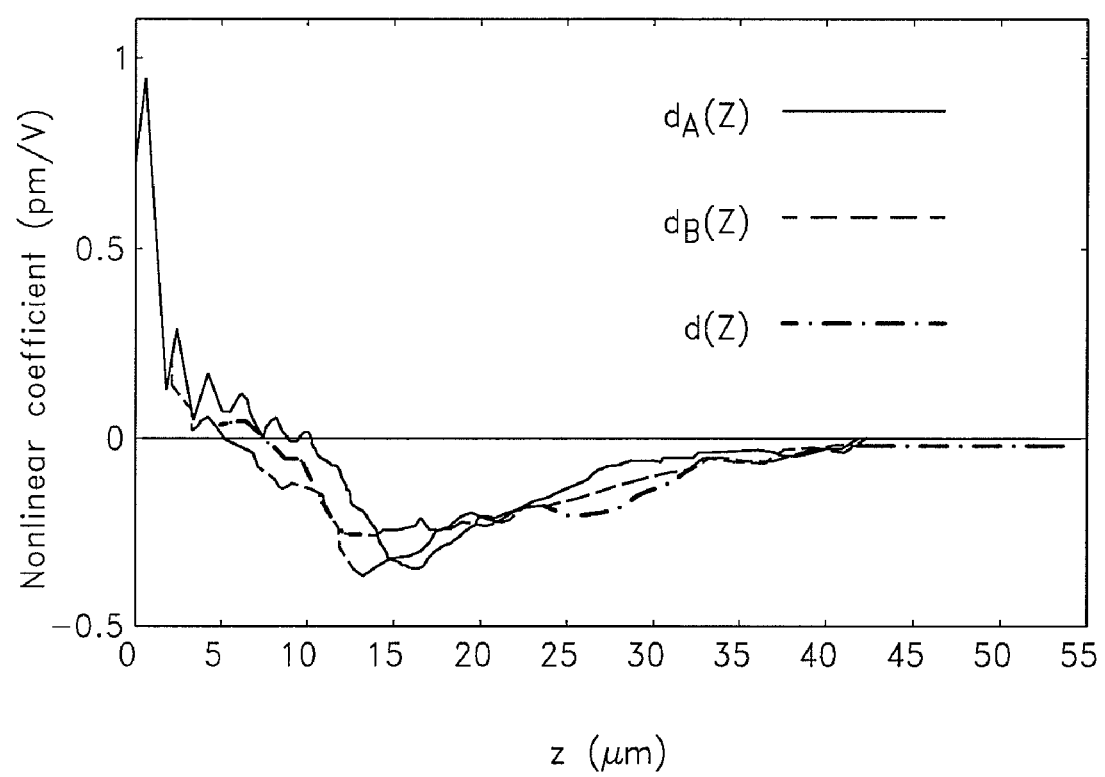
FIG. 19 illustrates the nonlinearity profiles $d_A(z)$ and $d_B(z)$ of two samples measured in accordance with embodiments of the present invention, and a nonlinearity profile d(z) measured using only one composite sample in accordance with embodiments of the present invention.

FIG. 19 illustrates the recovered sample nonlinearity profiles for Sample A and Sample B. The nonlinear coefficients peak at about one micron below the anode surface, with values of approximately 0.9 pm/V for $d_A(z)$ and approximately 1.0 pm/V for $d_B(z)$. The two profiles are similar in shape and magnitude, which is expected since they were poled under identical conditions. The difference between the locations of the negative peaks may be due to small variations in poling conditions. Since $d_A(z)$ and $d_B(z)$ are quite similar, it is also possible to retrieve these profiles by assuming that they are identical and applying the embodiment described above in relation to FIG. 9. The nonlinearity profile recovered in this fashion is also shown in FIG. 19. As expected, this profile is similar to both $d_A(z)$ and $d_B(z)$. The positive peak of this profile is nearly identical to those of $d_A(z)$ and $d_B(z)$, and the negative peak of this profile provides an effective average of those of $d_A(z)$ and $d_B(z)$. This comparison establishes that these two embodiments are consistent, and that the embodiment of FIG. 16 can discriminate between slightly different profiles and thus offer a greater accuracy. The inferred profiles of FIG. 19 are also similar to profiles retrieved from similarly poled samples, confirming that the nonlinearity changes sign and extends approximately 45 microns below the anode surface.

Certain embodiments of this method provide convenient consistency checks. Since $d_A(z)$ and $d_B(z)$ are now known, the theoretical MF data curves can be computed for Sample A, Sample B, the first composite sample, and the second composite sample to confirm that they are identical or similar to the corresponding measured MF data curves. Such theoretical MF data curves are illustrated in FIGS. 18A-18D as solid lines. The agreement between the measured and theoretical MF data curves for Sample A and Sample B are quite good, even at high incidence angles, except above approximately 89 degrees, where the data dip sharply. This can be due to the residual index mismatch between the silica samples and the gel between the silica samples. The agreement between the measured and theoretical MF data curves for the first composite sample and the second composite sample are good up to an incidence angle of approximately 60-70 degrees. At higher angles, the measured $MF_{S1}$ and $MF_{S2}$ curves fail to show the expected rapid oscillations present in the theoretical curves. The reason is that at high angles, the Maker fringes oscillate rapidly and cannot be resolved because of the finite divergence of the laser beam. Instead, several adjacent Maker fringes are excited and averaged out. This mechanism may cause the lower contrast in the measured MF fringes as compared to the theoretical MF fringes at higher angles in FIGS. 18A and 18B.

In practice, a measured MF data curve does not provide the low and high frequency ends of the Fourier transform spectrum. During data processing, the resulting abrupt discontinuities in the Fourier transform data in these regions introduce artificial oscillations in the inferred profiles. Since $d_A(z)$ and $d_B(z)$, $C_1(z)$, and $C_2(z)$ are zero outside a finite region and are square-integrable, their Fourier transforms are entire functions, which implies that in principle the whole Fourier transform can be reconstructed uniquely from the knowledge of the Fourier transform in a finite frequency range, as described by Millane, referenced herein. One implementation of this principle is the Papoulis-Gerchberg algorithm, described by P. J. S. G. Ferreira in *IEEE Transactions on Signal Processing*, 1994, Volume 42, page 2596, incorporated in its entirety by reference herein, which can be used to extrapolate the measured data into the unmeasured low and high frequency end portions of the Fourier spectrum.

Although this embodiment utilizes the measurement of two MF data curves, it is not any more labor-intensive than embodiments which utilize only one measurement, since it provides two profiles instead of a single one. Furthermore, after a pair of nonlinear samples have been characterized in this manner, either one of the two samples can be used as a reference sample with a known profile for measuring the profile of any other nonlinear sample, thereby using only a single new MF measurement (e.g., $MF_{S2}$). Data processing for this single-measurement case is slightly different and even simpler. For example, if the sample that is measured is S2, by selecting a thick enough sample so that $L_B > W_A + W_B$, $C_2(z)$ can be retrieved unambiguously from the $z \leq 0$ portion of the inverse Fourier transform of $MF_{S2}$. Since the nonlinearity profile $d_A(z)$ of the reference sample is known, the Fourier transform of $C_2(z)$ (i.e., $|D_A| \cdot |D_B| \cdot e^{j[\Phi_A - \Phi_B]}$) immediately provides both $|D_A|$ and $\phi_B$, and taking the inverse Fourier transform of $|D_B| \cdot e^{j\Phi_B}$ yields the unknown profile $d_B(z)$.

Figure 20:
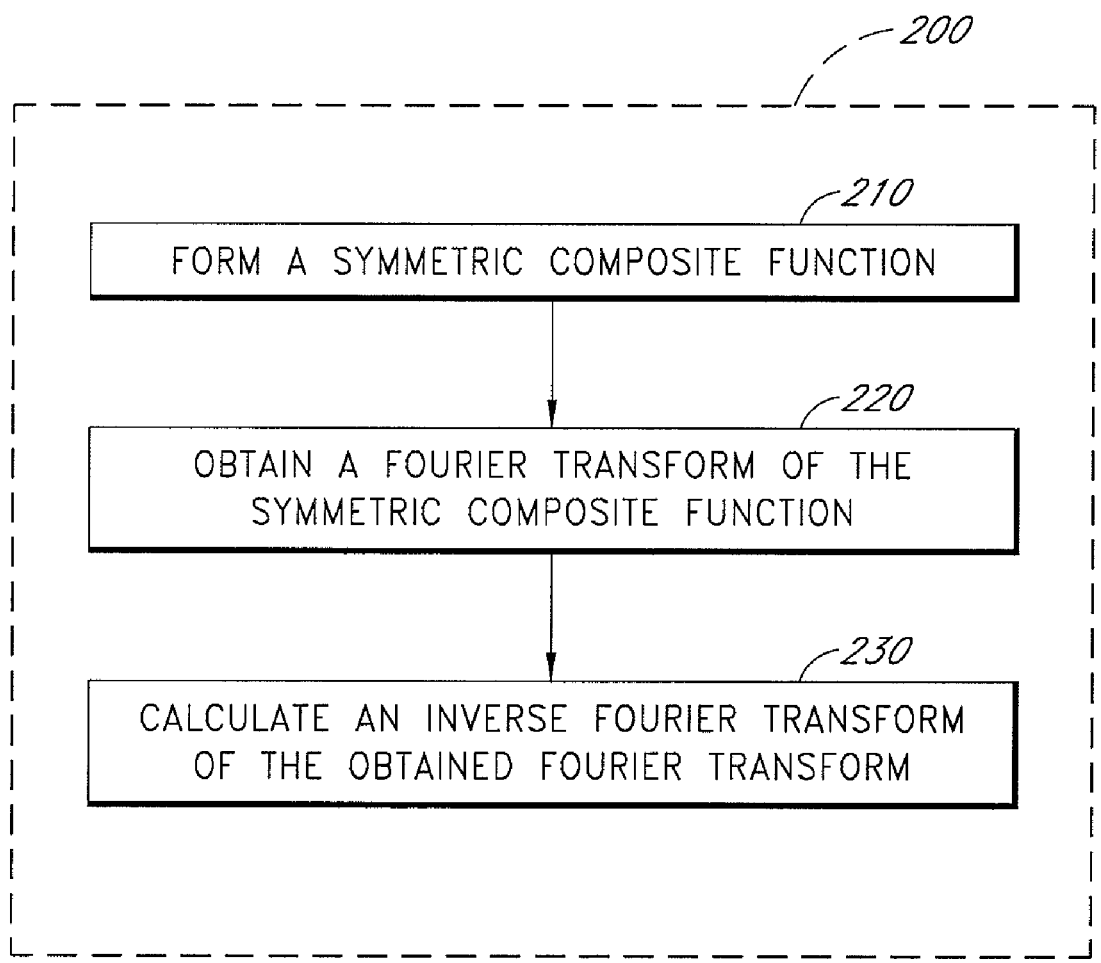
FIG. 20 is a flow diagram of a method in accordance with embodiments of the present invention for measuring physical functions.

Embodiments described herein can also be used to measure other physical functions. FIG. 20 is a flowchart of a method 200 in accordance with embodiments of the present invention. In an operational block 210, a symmetric composite function is formed. In an operational block 220, a Fourier transform of the symmetric composite function is obtained. In an operational block 230, an inverse Fourier transform of the obtained Fourier transform is calculated. The calculated inverse Fourier transform provides information regarding the physical function.

In certain embodiments, the symmetric composite function is an odd function (i.e., is symmetric about the origin). In other embodiments, the symmetric composite function is even (i.e., symmetric about the y-axis). In certain embodiments, obtaining the Fourier transform of the composite function comprises obtaining a Fourier transform magnitude of the composite function and using the Fourier transform magnitude to calculate the Fourier transform of the composite function.

For example, instead of forming a symmetric composite function in the spatial domain as described above in relation to the nonlinearity profile of poled silica, other embodiments form a symmetric intensity profile in the time domain by the use of time reversal. In such embodiments, the symmetric (even) composite function can have utility where phase information is needed but unavailable (e.g., ultra-short pulse diagnosis using auto-correlators). An example of time reversal is described by D. A. B. Miller in *Time Reversal of Optical Pulses by Four-Wave Mixing*, Optics Letters Vol. 5, 1980, pages 300-302, which is incorporated in its entirety by reference herein.

Figure 21:
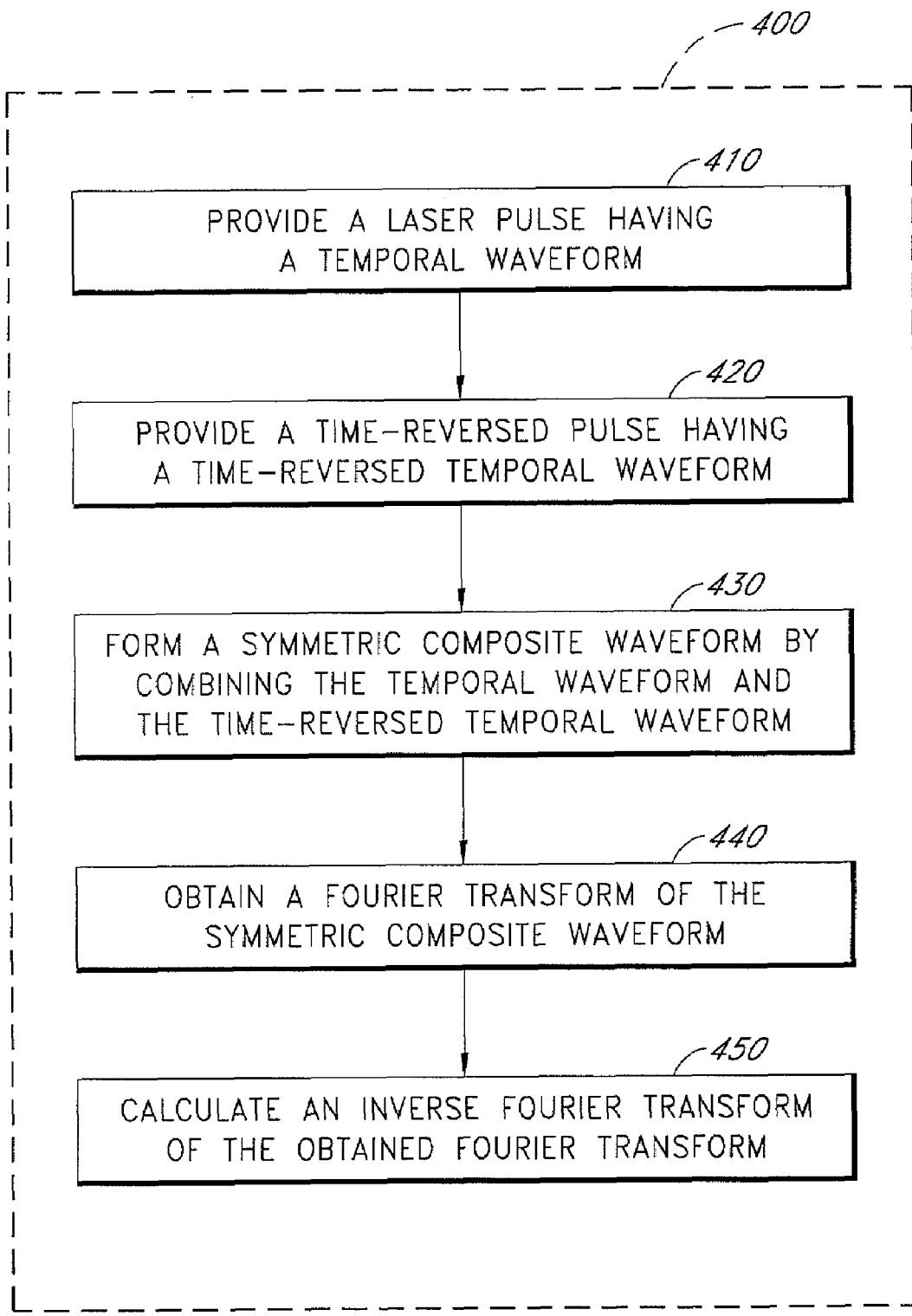
FIG. 21 is a flow diagram of a method of determining the temporal waveform of a laser pulse in accordance with embodiments of the present invention.
Figure 22:
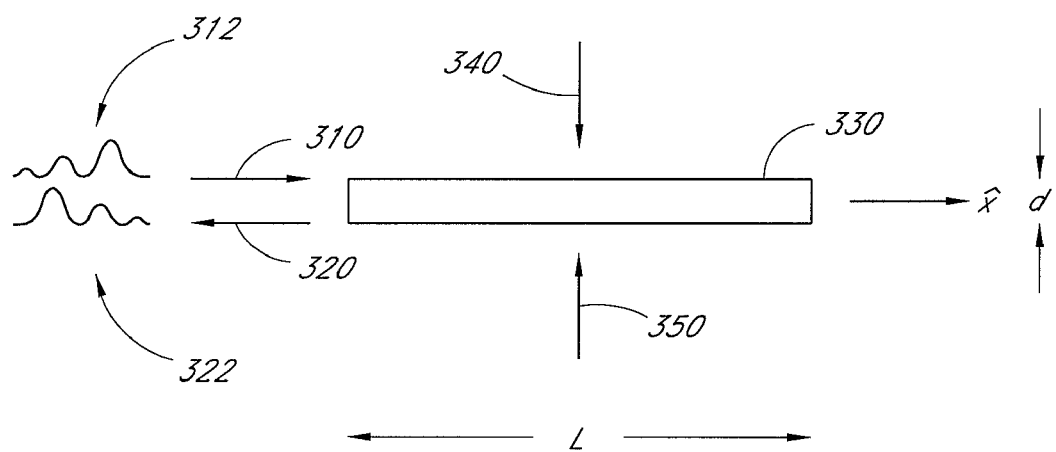
FIG. 22 schematically illustrates four-wave mixing (FWM) with pulsed pumps for providing the time-reversed pulse in accordance with embodiments of the present invention.

FIG. 21 is a flow diagram of a method 400 of determining the temporal waveform 312 of a laser pulse 310 in accordance with embodiments of the present invention. FIG. 22 schematically illustrates one configuration for utilizing four-wave mixing (FWM) to provide the time-reversed pulse 320 in accordance with embodiments of the present invention. Other configurations are also compatible with the method of FIG. 21. Referring to the elements illustrated in FIG. 22, in an operational block 410, a laser pulse 310 is provided. The laser pulse 310 has a temporal waveform 312. In an operational block 420, a time-reversed pulse 320 is provided. The time-reversed pulse 320 has a time-reversed temporal waveform 322 which corresponds to the temporal waveform 312 after being time-reversed. In an operational block 430, the temporal waveform 312 of the laser pulse 310 and the time-reversed temporal waveform 322 of the time-reversed pulse 320 form a symmetric composite waveform. In an operational block 440, a Fourier transform of the symmetric composite waveform is obtained. In certain embodiments, obtaining the Fourier transform of the symmetric composite function comprises measuring a Fourier transform magnitude of the symmetric composite function, and using the measured Fourier transform magnitude to calculate the Fourier transform of the symmetric composite function. In an operational block 450, an inverse Fourier transform of the obtained Fourier transform is calculated. The calculated inverse Fourier transform provides information regarding the temporal waveform 312 of the laser pulse 310.

FWM has been a subject of interest in applications such as aberration compensation, spatial information processing, frequency filtering, pulse envelope shaping, and dispersion compensation. As illustrated in FIG. 22, a nonlinear medium 330 of length L is pumped by two pulsed pump waves 340, 350. An input laser pulse 310 (with temporal waveform 312 given by $E_p(x,t)$) launched into the nonlinear medium 330 generates a phase conjugate pulse 320 (with time-reversed temporal waveform 322 given by $E_c(x,t)$), which is the time-reversed version of the temporal waveform 312 of the input pulse 310. In the embodiment described below, the input pulse 310, two pump waves 340, 350, and the nonlinear medium are at the same place for the duration of the input pulse 310. In addition, the input pulse 310, and the two pump waves 340, 350 overlap in the frequency domain.

Illustratively, the temporal waveform 312 of the input pulse 310 can be written in the following form:

$$E_p(x, t) = \frac{1}{2} u_p(t) e^{j(\omega_p t - kx)} + \text{complex conjugate.} \quad (33)$$

where $u_p(t)$ is the modulation of the carrier $e^{j(\omega_p t - kx)}$. The Fourier transform of $u_p(t)$ has the following form:

$$\overline{U}_p(\omega) = \int u_p(t) e^{-j\omega t} dt. \quad (34)$$

The temporal waveform of the resultant conjugate pulse 320 has the following form:

$$E_c(x, t) = \frac{1}{2} u_c(t) e^{j(\omega_c t + kx)} + \text{complex conjugate} \quad (35)$$

where "c" stands for "conjugate." Note that the k-vector of the conjugate pulse $E_c(x,t)$ has the reverse sign as expected. The Fourier transform of the envelope function $u_c(t)$ is defined the same way:

$$\overline{U}_c(\omega) = \int u_c(t) e^{-j\omega t} dt. \quad (36)$$

The relationship between the carrier frequencies $\omega_c$, $\omega_p$, as defined above, and the center frequencies $\omega_{pump,1}$ and $\omega_{pump,2}$ of the two pumps 340, 350 is:

$$\omega_{pump,1} + \omega_{pump,2} - \omega_p = \omega_c \qquad (37)$$

With these definitions, the envelope function $u_c(t)$ can be expressed as:

$$u_c(t) = \int h(\omega) \overline{U}_p^*(-\omega) e^{j\omega t} d\omega \qquad (38)$$

where $h(\omega)$ is the response function of the nonlinear material 330. For broadband conjugators (with respect to the spectrum of $u_p(t)$), $h(\omega)$ can be taken as a constant (K), giving $u_c(t)$ the following form:

$$u_c(t) = K \int \overline{U}_p^*(-\omega) e^{j\omega t} d\omega. \qquad (39)$$

The foregoing forms of the envelope function $u_c(t)$ were obtained using the teachings of R. A. Fischer et al. in *Transient Analysis of Kerr-Like Phase Conjugators Using Frequency-Domain Techniques*, Physical Review A, Vol. 23, 1981, pages 3071-3083, which is incorporated in its entirety by reference herein.

The above equations can be used to show that for continuous-wave (CW) pumping, FWM can not time-reverse pulsed fields. This property of FWM in CW pumping has been extensively studied for dispersion compensation in fiber links. Examples of such work include A. Yariv et al. in *Compensation for Channel Dispersion by Nonlinear Optical Phase Conjugation*, Optics Letters Vol. 4, 1979, pages 52-54, and S. Watanabe et al. in *Compensation of Chromatic Dispersion in a Single-Mode Fiber by Optical Phase Conjugation*, IEEE Photonics Technical Letters, Vol. 5, 1993, pages 92-95, both of which are incorporated in their entirety by reference herein.

However, pulsed pumping can be used to achieve time reversal of amplitude pulses. Following the derivation of D. A. B. Miller (cited above), $u_c(t)$ can be expressed as:

$$u_c(t) = K' u_p^*(-t + \tau_0) \qquad (40)$$

where K' and $\tau_0$ are constants. The $-t$ term in Equation 40 indicates the time reversal operation. Note that Equation 33 and Equation 37 are still valid for this case. The assumptions made in the derivation of Equation 40 are that:

(1) the nonlinear medium 330 has a length L equal to or longer than the spatial length of the input pulse 310 (i.e., large L assumption) so that the input pulse 310 is completely within the nonlinear medium 330 at some time during the interaction;

(2) the pump pulses 340, 350 are perpendicular to the nonlinear medium as shown in FIG. 22;

(3) pump pulses 340, 350 are short compared with the input pulse 310 (i.e., the spectra of both pump pulses 340, 350 are broad enough so that all of the frequency components of the input pulse 310 see a substantially uniform pump spectral power density for both pumps);

(4) as a consequence of (3), the thickness of the nonlinear medium 330 is preferably equal to or slightly greater than the spatial length of the pump pulses 340, 350); and (5) the timing of the pulses is such that when pulse 310 spatially fills the nonlinear medium 330 (i.e. the input pulse 310 is fully within the medium), the pump pulses 340 and 350 are timed to be overlapping in space with the input pulse 310 across the nonlinear medium filled by the input pulse.

Some of the details of these assumptions can be found in D. A. B. Miller's work (cited above). As described below, the apparatus schematically illustrated by FIG. 22 can serve as a phase conjugate mirror which generates the time-reversed waveform corresponding to an input waveform.

In other embodiments, the time-reversed pulse 320 can be provided using holographic techniques in accordance with embodiments of the present invention. Femtosecond spectral holography can be considered as a temporal analog of the classical spatial domain holography. In classical holography, a spatial information carrying beam (signal) and a uniform reference beam interfere in a recording medium, thereby recording a hologram comprising a set of fringes. Illumination of the hologram with a uniform test beam reconstructs either a real or conjugate image of the signal beam, depending on the geometry.

Figure 23A:
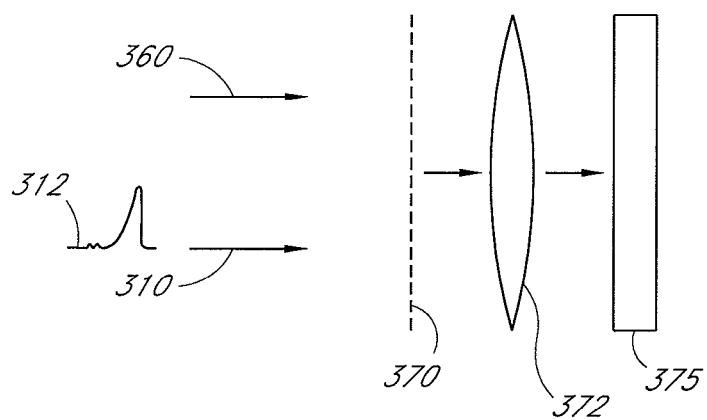
FIGS. 23A and 23B schematically illustrate femtosecond spectral holography for providing the time-reversed pulse in accordance with embodiments of the present invention.
Figure 23B:
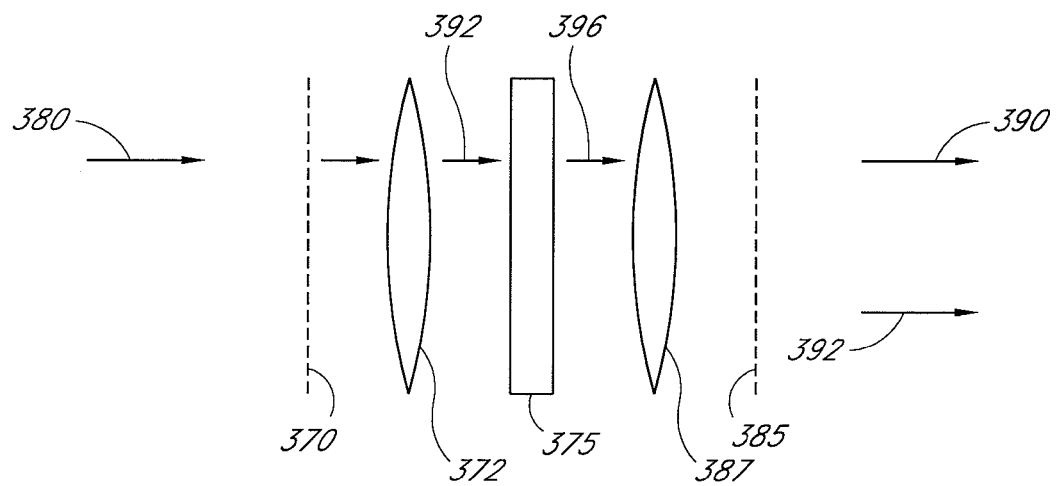

Femtosecond spectral holography for the time reversal process comprises a recording phase and a read-out phase, as schematically illustrated respectively by FIGS. 23A and 23B. In the recording phase (FIG. 23A), the reference pulse 360 is short with a relatively flat and broad spectrum, and the input pulse 310 has a temporal waveform 312 that has a shape indicative of information carried by the input pulse 310. During the recording of the hologram, a grating 370 is used to disperse both the reference pulse 360 and the input pulse 310 into their spectral components, which then propagate through a collimating lens system 372. The interference pattern formed by the complex amplitudes of each spectral component is then recorded in the holographic recording plate 375.

In the read-out phase (FIG. 23B), a short test pulse 380 is dispersed by the grating 370 and then recollimated by the lens 372. The illumination of the holographic plate 375 with this recollimated dispersed test beam 392 produces the beam 396. Using the lens 387 for recollimation and the second grating 385, a time-reversed replica 390 of the original input pulse 310 is produced. Also as a by-product, the transmitted test beam 392 appears at the output. The details of this technique are described more fully by A. M. Weiner et al. in *Femtosecond Spectral Holography*, IEEE Journal of Quantum Electronics, Vol. 28, 1992, pages 2251-2261, and A. M. Weiner et al. in *Femtosecond Pulse Shaping for Synthesis, Processing and Time-to-Space Conversion of Ultrafast Optical Waveforms*, IEEE Journal of Selected Topics in Quantum Electronics, Vol. 4, 1998, pages 317-331, both of which are incorporated in their entireties by reference herein.

The envelope of the output pulse 390 can be expressed as:

$$u_{out}(t) \approx u_t(t) * u_r(-t) * u_s(t) e^{j\vec{K}_1 \vec{r}} + u_t(t) * u_r(t) * u_s(-t) e^{j\vec{K}_2 \vec{r}} \qquad (41)$$

where $u_{out}(t)$, $u_t(t)$, $u_r(t)$, and $u_s(t)$ are the complex envelope functions of the electric fields of the output pulse 390, test pulse 380, reference pulse 360, and input pulse 310, respectively. The sign '*' denotes the convolution function, and $\vec{K}_1 = \vec{k}_t - \vec{k}_r + \vec{k}_s$ and $\vec{K}_2 = \vec{k}_t + \vec{k}_r - \vec{k}_s$.

When the test pulse 380 and the reference pulse 360 are considerably shorter than the input pulse 310, the complex envelope functions $u_s(t)$, $u_t(t)$, and $u_r(t)$ will act as delta functions with respect to $u_s(t)$, modifying the envelope of the output pulse 390 to be:

$$u_{out}(t) \approx u_s(t) e^{j\vec{K}_1 \vec{r}} + u_s(-t) e^{j\vec{K}_2 \vec{r}}. \qquad (42)$$

Therefore, as a result of the illumination of the holographic plate with the test pulse 380, the output pulse 390 serves as the time-reversed signal pulse 320 in the $\vec{K}_2$ direction. As described below, the apparatus schematically illustrated by FIGS. 23A and 23B can serve as a phase conjugate mirror which generates the time-reversed waveform corresponding to an input waveform.

Note that embodiments of both the pulse-pumped FWM and the spectral holography techniques use shorter pulses than the input pulse 310 to time-reverse the input pulse 310. For pulse-pumped FWM, shorter pump pulses 340, 350 are used, and for holography, shorter test pulses 380 and reference pulses 360 are used.

Figure 24:
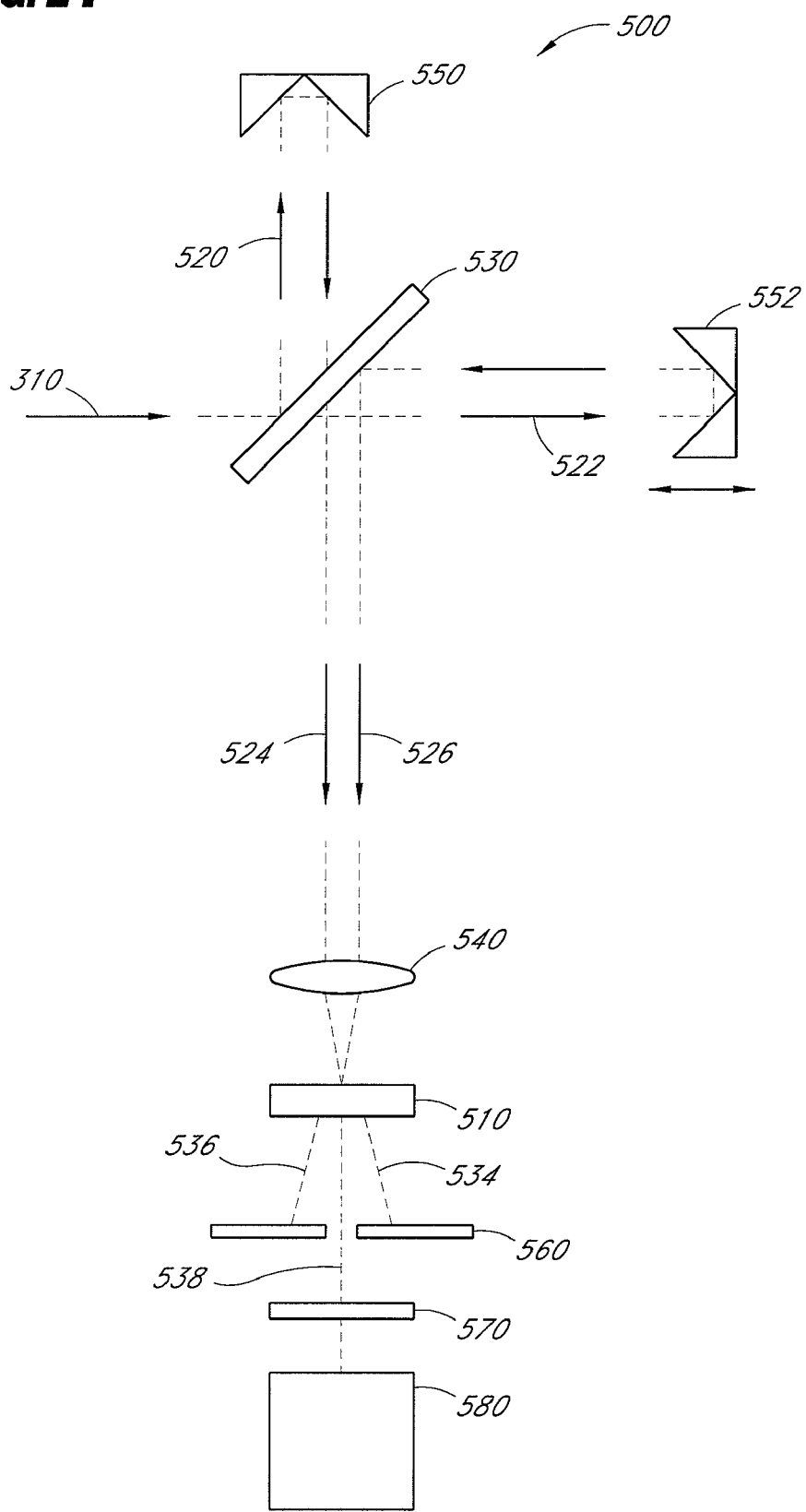
FIG. 24 schematically illustrates one embodiment of a classical intensity correlator utilizing a Michelson interferometer.

FIG. 24 schematically illustrates one embodiment of a classical intensity correlator utilizing a Michelson interferometer 500 in combination with a second-harmonic generating (SHG) crystal 510 to estimate the temporal waveform of a laser pulse. The input pulse 310 is split into a first pulse 520 and a second pulse 522 by the beamsplitter 530. The first pulse 520 is reflected by a fixed mirror 550 back through the beamsplitter 530, thereby transmitting a third pulse 524. The second pulse 522 is reflected by a movable mirror 552 back through the beamsplitter 530, thereby transmitting a fourth pulse 526 towards the focusing lens 540. The movable mirror 552 adds a variable delay $\tau$ to the fourth pulse 526 with respect to the third pulse 524. The focusing lens 540 focuses the third pulse 524 and the fourth pulse 526 onto the SHG crystal 510. The SHG crystal 510 generates a second-harmonic (SH) field 538 which is a cross-correlation product of the third pulse 524 and the fourth pulse 526. Other SH fields 534, 536 generated by the SHG crystal 510 do not carry information regarding the third and fourth pulses 524, 526 simultaneously, and these other SH fields are blocked by the pinhole 560 placed after the SHG crystal 510. After passing through a filter 570 which blocks light at the fundamental wavelength and which passes the SH light, the cross-correlation product 538 is detected by a photomultiplier tube 580.

The third pulse 524 emerging from one arm of the Michelson interferometer 500 has a waveform given by:

$$E_1(t) = u_1(t) e^{j\omega t} \quad (43)$$

where $u_1(t)$ is the complex envelope function of the input pulse 310. The fourth pulse 526 emerging from the other arm of the Michelson interferometer 500 has a waveform given by:

$$E_2(t) = u_2(t) e^{j\omega t} = u_1(t-\tau) e^{j\omega(t-\tau)} \quad (44)$$

where $\tau$ is the relative time delay between the third pulse 524 and the fourth pulse 526 imposed by the delay $\tau$ between the two arms. Because of the focusing lens 540, the third pulse 524 and the fourth pulse 526 have different k-vectors at the surface of the SHG crystal 510. Consequently, the SH field 538 generated by the SHG crystal 510 that is not blocked by the pinhole 560 includes only terms due to the interaction of the third pulse 524 and the fourth pulse 526, and has a waveform given by:

$$E_{2\omega}(t) = u_{2\omega}(t) e^{j2\omega t} = \eta u_1(t) u_2(t) e^{j2\omega t} = \eta u_1(t) u_1(t-\tau) e^{-j\omega \tau} e^{j2\omega t} \quad (45)$$

where $\eta$ is a conversion efficiency factor corresponding to the SHG crystal and the system geometry. The signal detected by the photomultiplier 580 (i.e., the autocorrelation function) is given by:

$$A_{PMT}(\tau) = \int E_{2\omega}(t) E_{2\omega}^*(t) dt = \int |\eta|^2 |u_1(t)|^2 |u_1(t-\tau)|^2 dt = |\eta|^2 \int I(t) I(t-\tau) dt \quad (46)$$

where $I(t) = |u_1(t)|^2$ is the input signal intensity. In general, $\eta$ is a function of frequency and the functions $u_1(t)$ and $u_2(t)$ can be expanded as plane waves with Fourier transform amplitudes (i.e., $u_i(t) = \int U_i(e^{j\omega t} d\omega)$. However, it is assumed here that $\eta$ is constant over the frequency range of the combined pulses, which is equivalent to assuming that $\chi^{(2)}$ is independent of frequency. This assumption holds when the effective crystal length is shorter than the coherence length of the harmonic generation over the pulse bandwidth.

By taking the Fourier transform of both sides of Equation 46 (the signal detected by the photomultiplier 580 for a single pulse) provides the Fourier transform of the autocorrelation function and is given by:

$$\overline{A}_{PMT\_single}(f) = |\eta|^2 |\overline{I}(f)|^2 \quad (47)$$

where $\overline{A}_{PMT\_single}(f)$ and $\overline{I}(f)$ are the Fourier transforms of $A_{PMT}(\tau)$ and $I(\tau)$, respectively. Thus, the signal from the Michelson interferometer 500 of FIG. 24 provides the magnitude of the Fourier transform of the input pulse intensity I(t).

However, the magnitude of the Fourier transform is not sufficient information to retrieve uniquely the input pulse intensity I(t). To do so would also require the knowledge of the phase of the Fourier transform, which this classical autocorrelation method does not provide. This difficulty in uniquely determining the input pulse intensity I(t) is analogous to that of retrieving the second-order susceptibility spatial profile of a nonlinear material, as described above. In practice, a number of methods can be used to avoid this difficulty. For example, a certain shape for the pulse intensity (e.g., a Gaussian) can be assumed, but there is no way to independently verify that the assumed shape is the true temporal waveform. This method therefore provides only an estimate of the pulse shape.

By using a time-reversal technique compatible with embodiments of the present invention (e.g., pulse-pumped FWM or femtosecond spectral holography), a time-reversed pulse with a time-reversed temporal waveform I(−t) of the temporal waveform I(t) of an arbitrary pulse can be produced. A symmetric composite waveform can then be formed by delaying the time-reversed pulse with respect to the original pulse and combining the temporal waveform with the time-reversed temporal waveform, for example with a beamsplitter.

Figure 25:
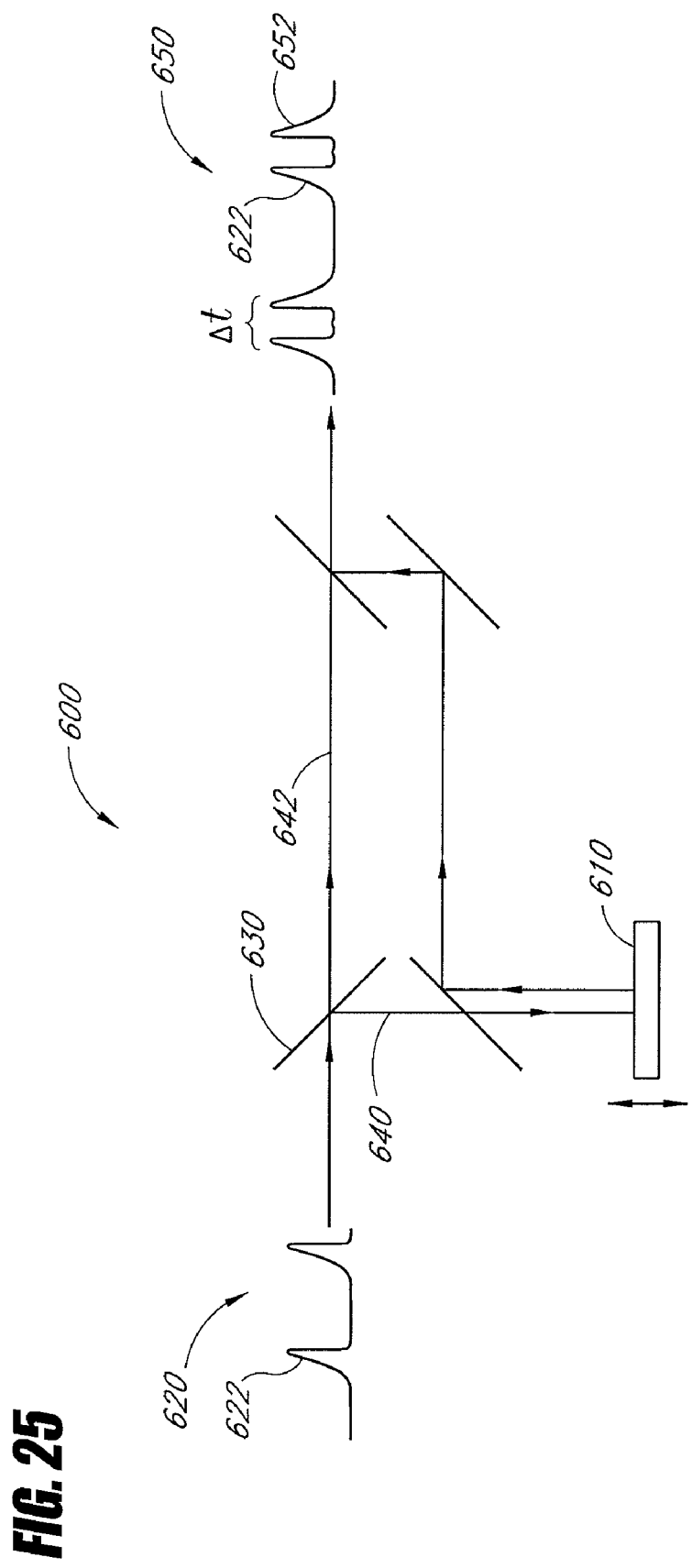
FIG. 25 schematically illustrates a general configuration for converting a periodically repeated sequence of pulses into a periodically repeated sequence of symmetric pulses using a movable phase conjugative mirror.

FIG. 25 schematically illustrates a general configuration 600 for converting a periodically repeated sequence of pulses into a periodically repeated sequence of symmetric pulses using a movable phase conjugative mirror 610. The input pulse sequence 620 comprises a series of original pulses 622. The original pulses 622 can be symmetric or asymmetric. Each of these original pulses 622 is split by the beamsplitter 630 into two portions 640, 642, with one portion 640 being reflected by a phase conjugate mirror 610. In certain embodiments, the phase conjugate mirror 610 comprises an apparatus as schematically illustrated by FIG. 22 in which the input pulse 310 is used to generate the output pulse 320. In certain other embodiments, the phase conjugate mirror 610 comprises an apparatus as schematically illustrated by FIGS. 23A and 23B in which the input pulse 310 is used to generate the output pulse 390. The portions 640, 642 are combined to form a symmetric composite waveform 650 comprising the temporal waveforms of the original pulses 622 and of the corresponding phase conjugate (time-reversed) pulses 652. The amount of delay $\Delta t$ between an original pulse 622 and the corresponding time-reversed pulse 652 in the symmetric pulse sequence 650 is adjustable by moving the phase conjugative mirror 610.

The symmetric composite waveform 650 has the following form:

$$I_{symmetric}(t) = I\left(-t - \frac{\Delta t}{2}\right) + I\left(t - \frac{\Delta t}{2}\right) \tag{48}$$

where $\Delta t$ is the variable time delay between the time-reversed pulse 652 and the original pulse 622. The Fourier transform of Equation 48 is given by:

$$\tilde{I}_{symmetric}(f) = \tilde{I}(-f)e^{jf\frac{\Delta t}{2}} + \tilde{I}(f)e^{-jf\frac{\Delta t}{2}}. \tag{49}$$

Since I(t) is real, $|\tilde{I}(f)|=|\tilde{I}(-f)|$ and $\phi(f)=-\phi(-f)$, where $\tilde{I}(f)$ has been defined as: $\tilde{I}(f)=|\tilde{I}(f)|e^{j\phi(f)}$. Using these identities, together with Equations 47 and 49, the Fourier transform of the autocorrelation function corresponding to the symmetric composite waveform 650 has the following form:

$$\tilde{A}_{PMT\_double}(f) = 2|\eta|^2 |\tilde{I}(f)|^2 |1 + \cos(2\phi(f) - f\Delta t)|. \tag{50}$$

In embodiments in which $\overline{A}_{PMT\_double}$ is real and greater than zero for all frequencies ω (i.e., there are no zero crossings of $\overline{A}_{PMT\_double}$ from the cosine term), then the inverse Fourier transform of Equation 50 provides the intensity of the symmetric pulse sequence 650 without any ambiguity. Once the intensity of the symmetric pulse sequence 650 is calculated in this way, the intensity of the original pulse can be found by separating the pulse 650 in the middle.

Figure 26:
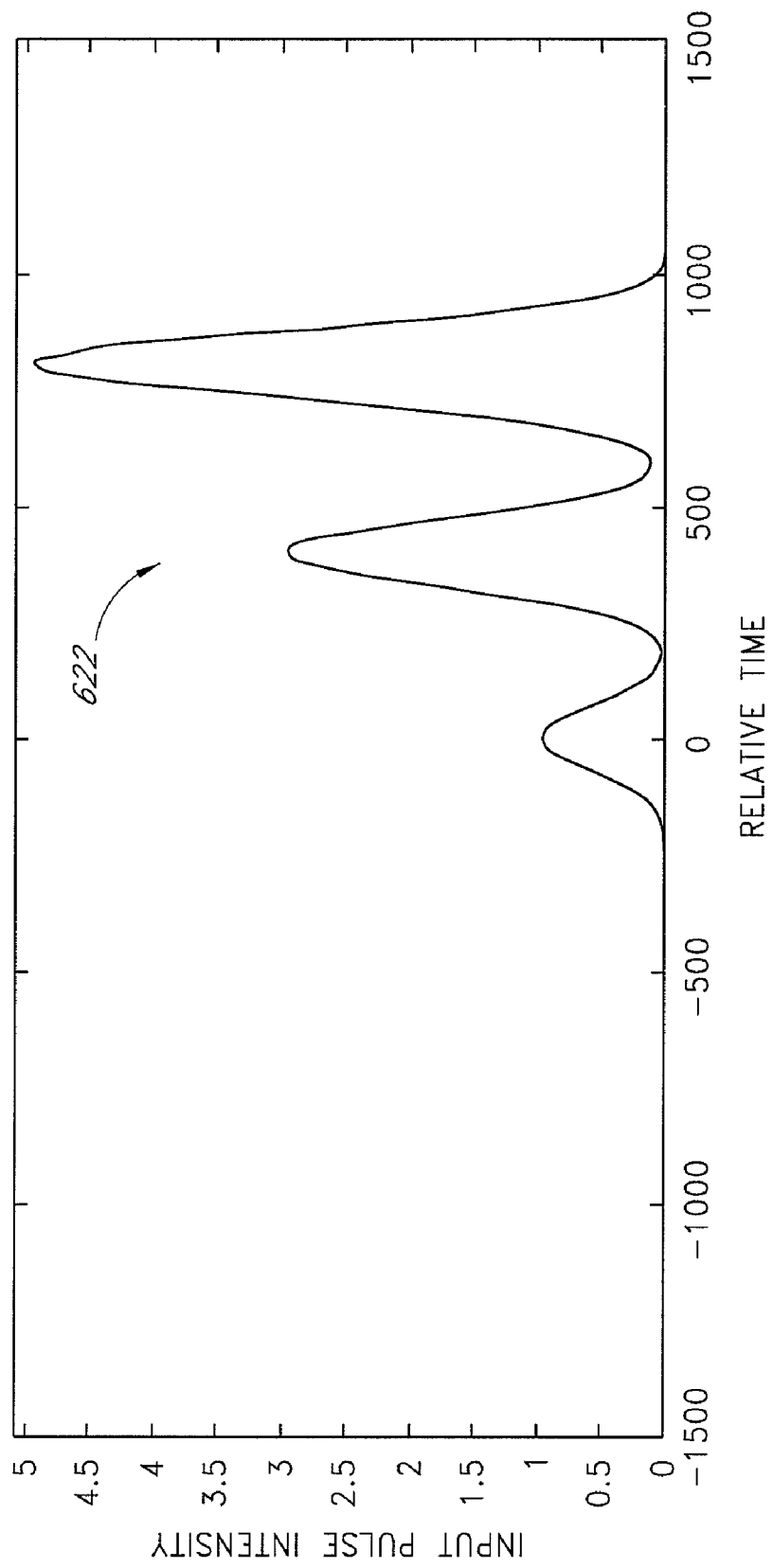
FIG. 26 illustrates an exemplary temporal waveform (in units of $W/m^2$) of an asymmetric input pulse compatible with embodiments of the present invention.
Figure 27:
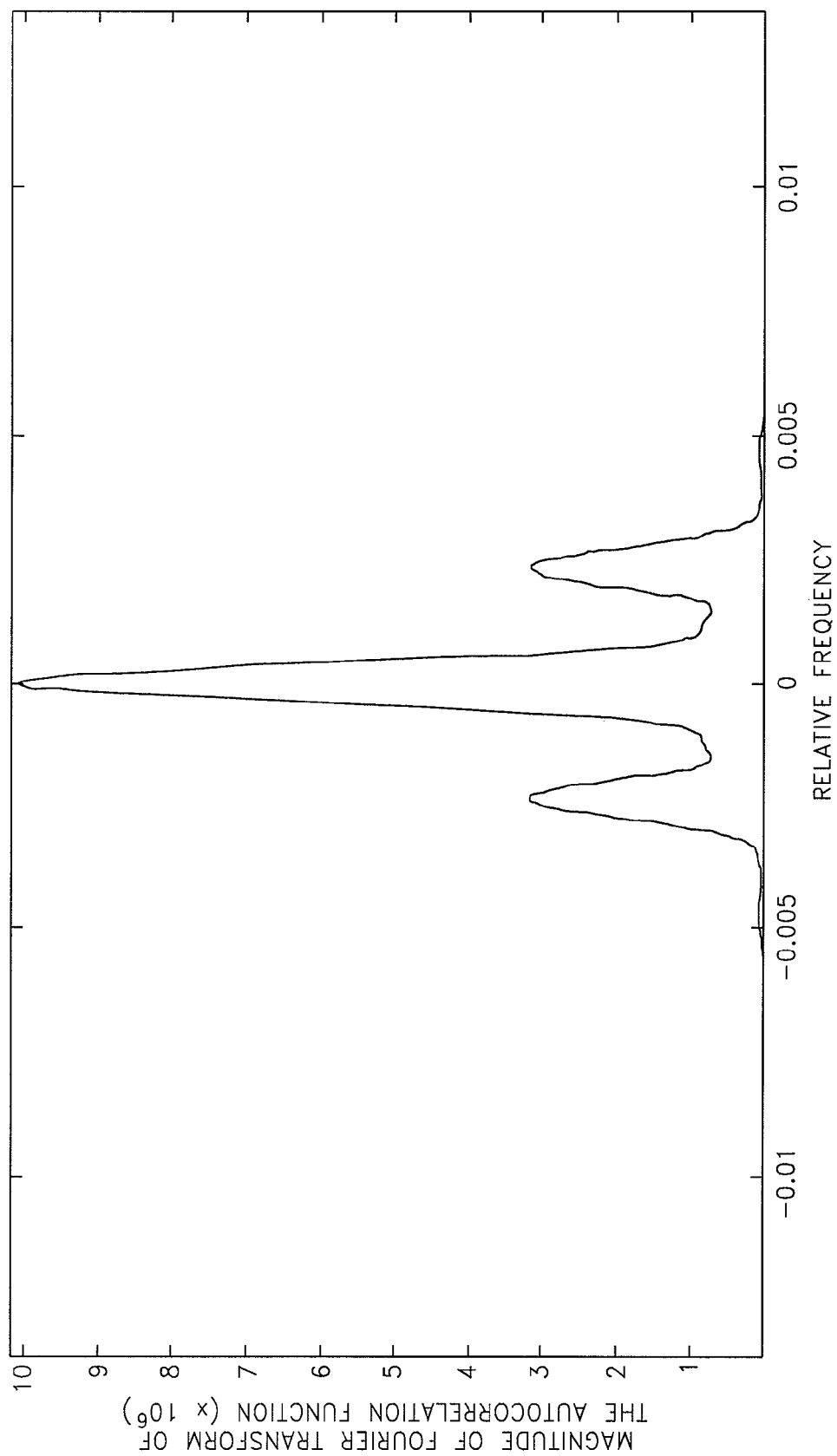
FIG. 27 illustrates the magnitude of the Fourier transform (unitless) of the autocorrelation function corresponding to the temporal waveform of FIG. 26.

FIG. 26 illustrates an exemplary temporal waveform of an input pulse 622 compatible with embodiments of the present invention. The autocorrelation technique commonly used to estimate the temporal profile of an optical pulse is applied to this input pulse as follows. By using the configuration schematically illustrated in FIG. 24, the autocorrelation function (Equation 46) corresponding to the temporal waveform is measured. The magnitude of the Fourier transform of the signal $A_{PMT\_single}(\tau)$ recorded by the photomultiplier tube 580 is schematically illustrated in FIG. 27. The frequency $f$ shown in FIG. 27 is $1/\tau$, and is not to be confused with the optical frequency.

Figure 28:
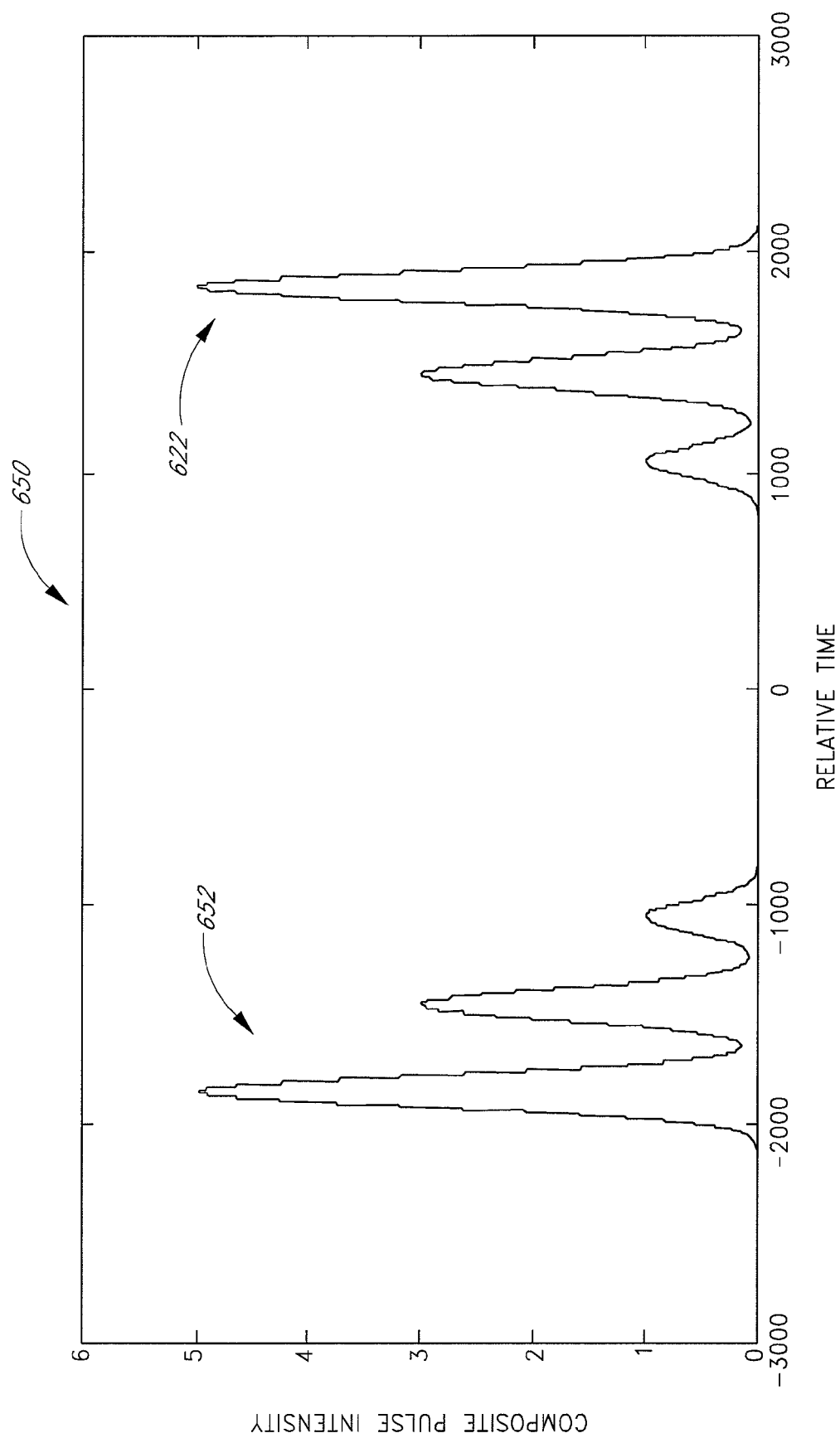
FIG. 28 illustrates the symmetric composite waveform (in units of W/m²) corresponding to the temporal waveform of FIG. 26.

In the following, an embodiment is illustrated analytically by showing the result of numerical simulations using the input pulse of FIG. 26. First, the time-reversal of the input pulse is obtained using one of the phase conjugate mirror schemes described above. FIG. 28 illustrates the symmetric composite waveform 650 defined by Equation 48, which is obtained by combining the input pulse and the time-reversed pulse. The symmetric composite waveform 650 comprises the temporal waveform of the original pulse 622 of FIG. 25 plus the time-reversed temporal waveform of the corresponding time-reversed pulse 652, separated by some time delay.

Figure 29:
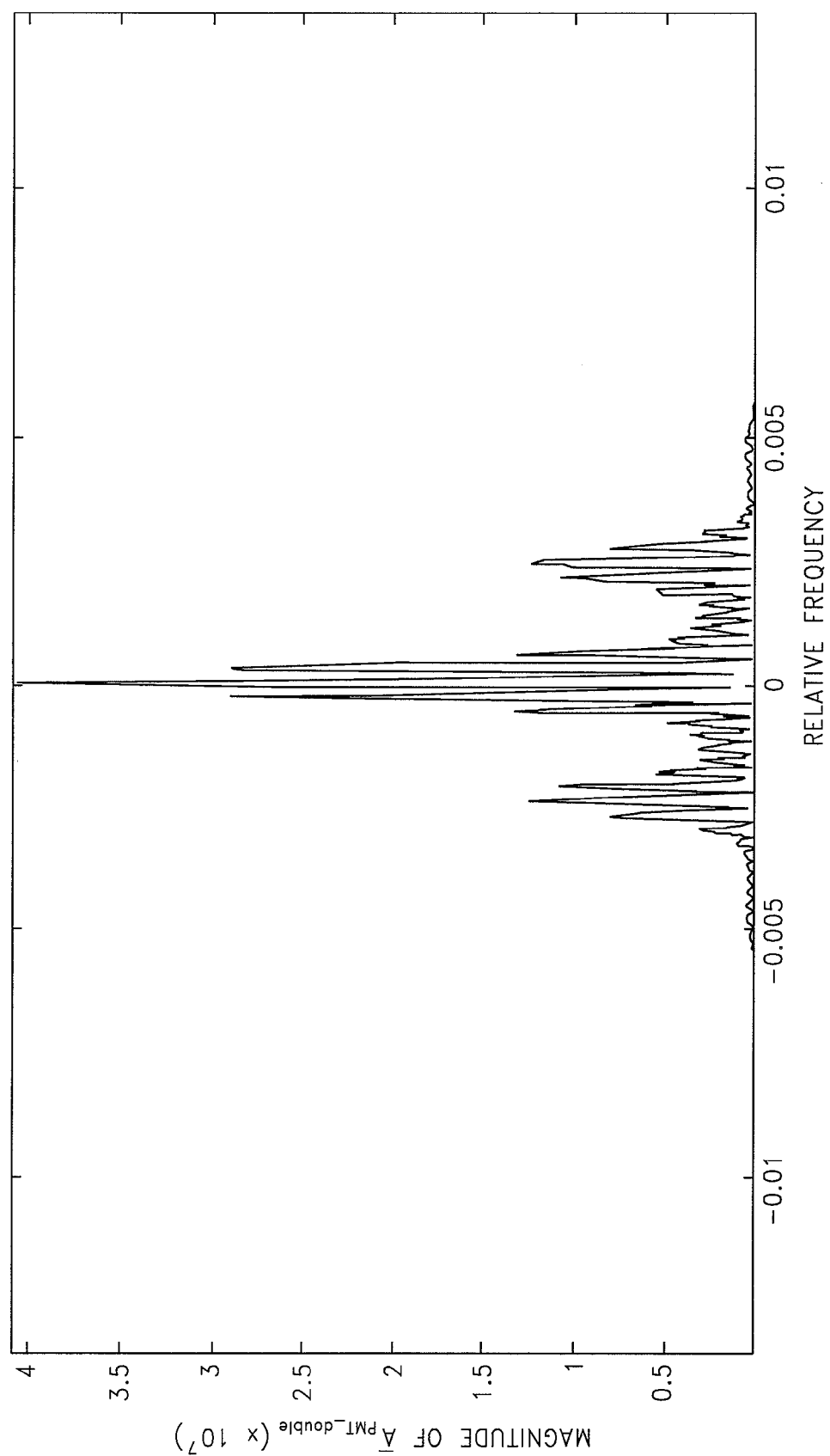
FIG. 29 illustrates the magnitude of the Fourier transform (unitless) of the autocorrelation function of the symmetric composite waveform of FIG. 28.

In the second step, the autocorrelator of FIG. 24 is used to generate the autocorrelation function corresponding to the symmetric composite waveform 650. FIG. 29 illustrates the magnitude of $\overline{A}_{PMT\_double}(f)$ (expressed by Equation 50), which is the Fourier transform of the measured $A_{PMT\_double}(\tau)$. The envelope of the Fourier transform magnitude of the measured $A_{PMT\_double}(\tau)$ is a scaled version of the Fourier transform magnitude (as shown in FIG. 27) of the signal $A_{PMT\_single}(\tau)$ measured by the photomultiplier tube 580. Therefore, $|\tilde{I}(f)|^2$ or $|\tilde{I}(f)|$ can be recovered from only the envelope of the Fourier transform magnitude of the measured $A_{PMT\_double}(\tau)$ (i.e., from only the measurement of the autocorrelation function of the symmetric composite waveform 650). This result implies that the measurement of the autocorrelation function for the single pulse as schematically illustrated in FIG. 26 is redundant. However, since it does not add complexity to the measurement, certain embodiments also comprise obtaining $|\tilde{I}(f)|^2$ data from a separate source for error checking purposes.

In the third step, the function $g(f)=1+\cos(2\phi(f)-f\Delta t)$ is determined by dividing both sides of Equation 50 by $|\tilde{I}(f)|^2$. From the knowledge of $g(f)-1$, the function $$\left|\cos\left(\varphi(f) - f\frac{\Delta t}{2}\right)\right|$$

can be determined. Using Equation 49, the Fourier transform of the symmetric temporal waveform can be expressed as:

$$\tilde{I}_{symmetric}(f) = 2|\tilde{I}(f)|\cos\left(\varphi(f) - f\frac{\Delta t}{2}\right). \tag{51}$$

Therefore, since $|\tilde{I}(f)|$ is known from FIG. 25 or from the envelope of FIG. 29, the only information needed to determine $I_{symmetric}(t)$ directly by taking the inverse Fourier transform of Equation 51 is the knowledge of $$\cos\left(\varphi(f) - f\frac{\Delta t}{2}\right).$$

To determine the function $$\cos\left(\varphi(f) - f\frac{\Delta t}{2}\right)$$

from the function $$\left|\cos\left(\varphi(f) - f\frac{\Delta t}{2}\right)\right|,$$

two possible cases can be analyzed. In the first case, if there are no zero crossings of the term $$\left|\cos\left(\varphi(f) - f\frac{\Delta t}{2}\right)\right|,$$

then there is no ambiguity due to the absolute value sign since intensity has to be non-negative ($-I_{symmetric}(t)$ is not a possible solution). In the second case, if there are some zero crossings of the term $$\left|\cos\left(\varphi(f) - f\frac{\Delta t}{2}\right)\right|,$$

the sign ambiguities of the cosine term between the zero crossings can be removed by using a property of Fourier transforms. For a real and symmetric function such as $I_{symmetric}(t)$, the Fourier transform $I_{symmetric}(f)$ is equivalent to the Hartley transform $I_{symmetric}^{Ha}(f)$. Therefore, the magnitude of the Hartley transform of $I_{symmetric}(t)$ (i.e., $$|I_{symmetric}^{Ha}(f)| = |I_{symmetric}(f)| = 2|\tilde{I}(f)|\left|\cos\left(\varphi(f) - f\frac{\Delta t}{2}\right)\right|$$

can be determined from the knowledge of $$\left|\cos\left(\varphi(f) - f\frac{\Delta t}{2}\right)\right| \text{ and } |\tilde{I}(f)|.$$

For a real and compact support function (i.e., one that equals zero outside a finite region), such as $I_{symmetric}(t)$, the intensity of the Hartley transform is enough to uniquely recover the original function. See, e.g., N. Nakajima in *Reconstruction of a real function from its Hartley-transform intensity*, Journal of the Optical Society of America A, Vol. 5, 1988, pages 858-863, and R. P. Millane in *Analytic Properties of the Hartley Transform and their Implications*, Proceedings of the IEEE, Vol. 82, 1994, pages 413-428, both of which are incorporated in their entirety by reference herein.

Figure 30A:
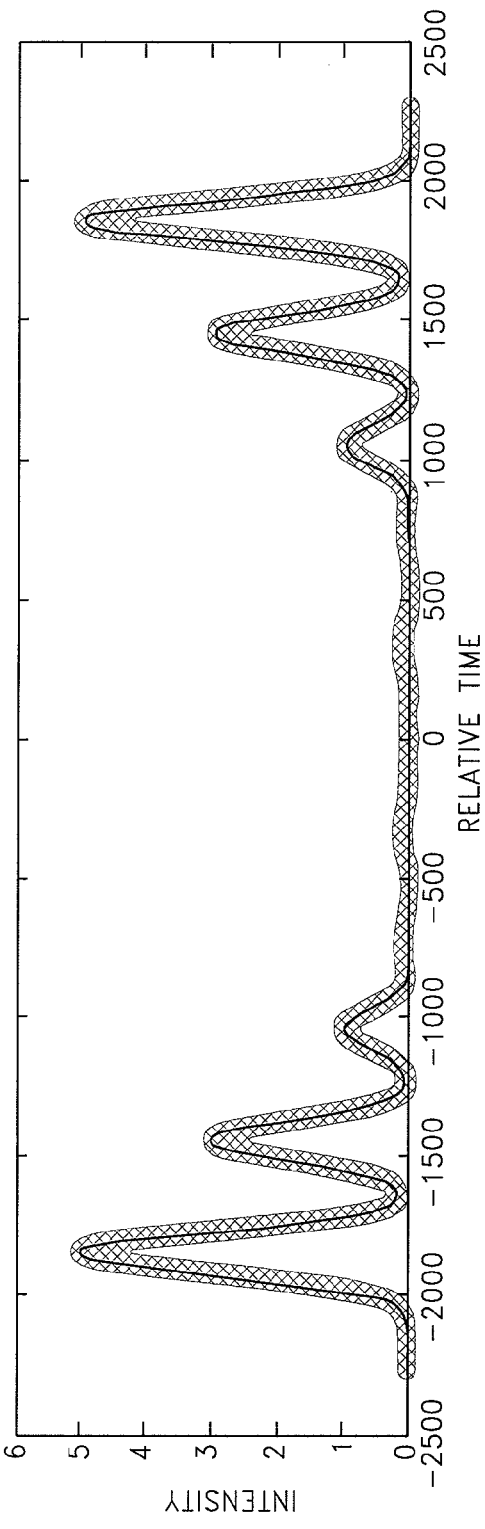
FIG. 30A illustrates the recovered symmetric temporal waveform (in units of W/m²).
Figure 30B:
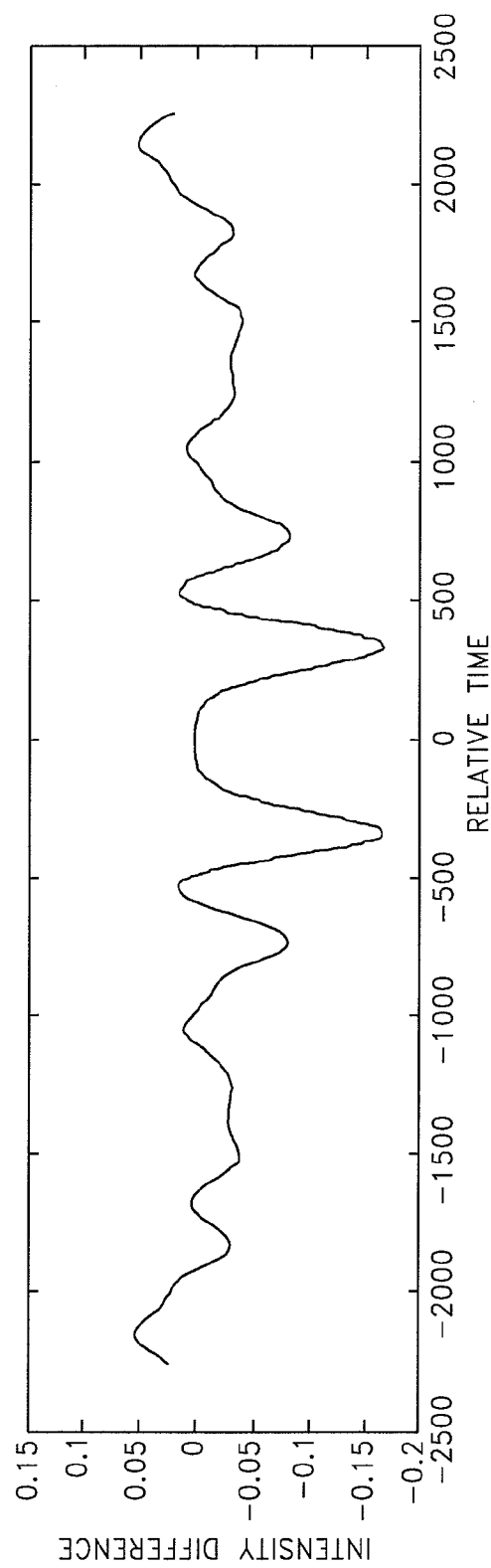
FIG. 30B illustrates the difference (in units of W/m²) between the recovered symmetric temporal waveform and the temporal waveform of the original pulse.

FIG. 30A illustrates the recovered symmetric temporal waveform and FIG. 30B illustrates the difference between the recovered symmetric temporal waveform and the temporal waveform of the original pulse (as shown in FIG. 28). As illustrated by FIG. 30B, the two waveforms are in excellent agreement (within approximately 0.15) with one another. The difference shown in FIG. 30B is in fact just a numerical calculation artifact, which can be improved with increased accuracy. Thus, the configuration schematically illustrated in FIG. 24 is capable of recovering ultra-short temporal waveforms unambiguously when used with a time-reversal scheme, such as that illustrated by FIG. 25.

Figure 31:
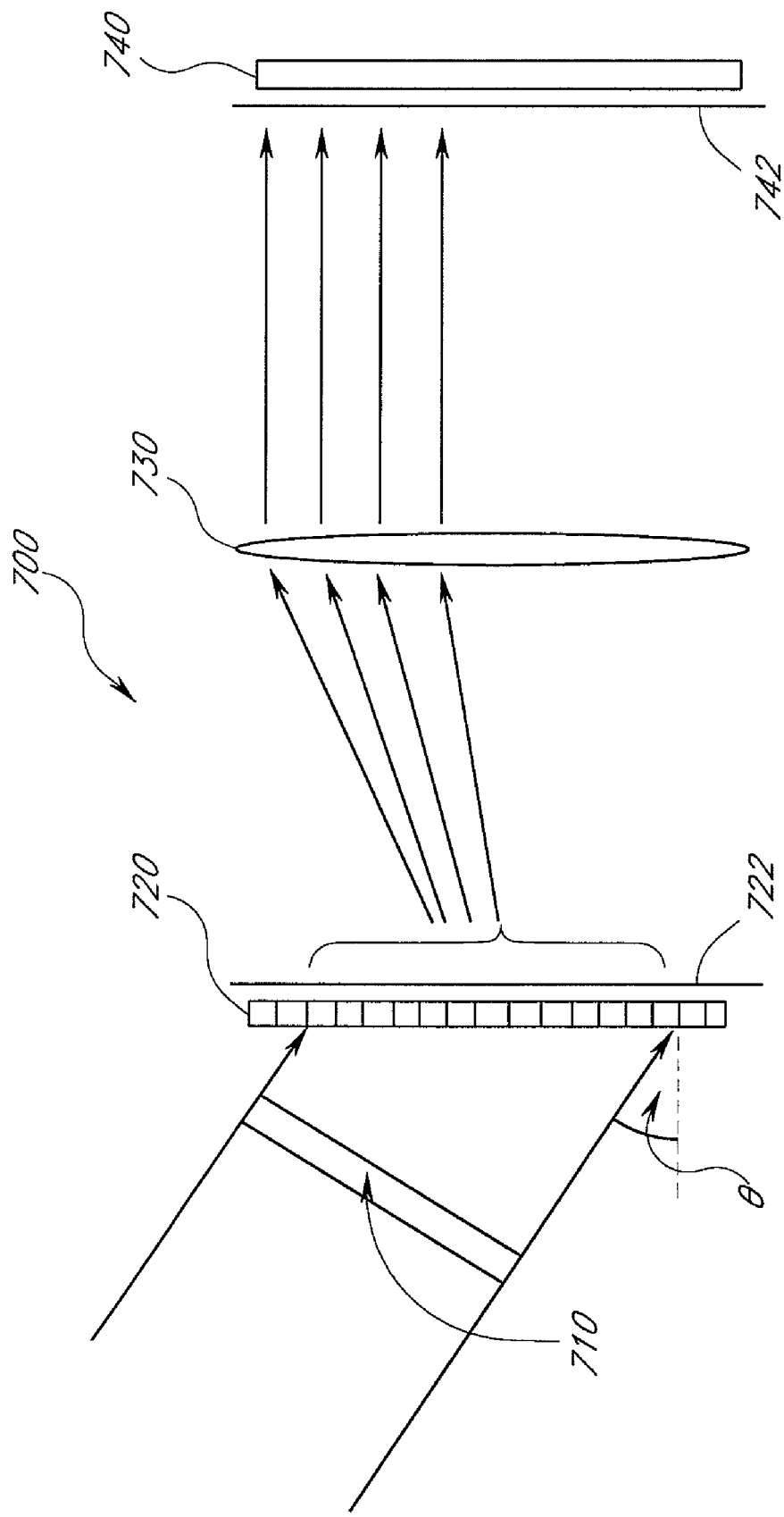
FIG. 31 schematically illustrates a system for another embodiment for determining the temporal waveform of a laser pulse.

FIG. 31 schematically illustrates a system 700 for another embodiment for determining the temporal waveform of a laser pulse. The input pulse 710 impinges onto a grating 720 which disperses the input pulse 710 into its spectral components. A lens 730 recollimates the spectral components and images them onto different elements of a CCD imaging device 740.

An arbitrary input pulse 710 has the following form:

$$u_s(t) = \tilde{u}_s(t)e^{j\omega_c t} \quad (52)$$

where $\tilde{u}_s(t)$ is the complex envelope function and $\omega_c$ is the carrier frequency. Equation 52 can be rewritten as:

$$u_s(t) = \int \tilde{U}_s(\omega - \omega_c)e^{j\omega t}d\omega \quad (53)$$

where $\tilde{U}_s(\omega)$ denotes the Fourier transform of $\tilde{u}_s(t)$. The input pulse 710 is decomposed by the grating 720 into several monochromatic plane waves with amplitudes $\tilde{U}_s(\omega - \omega_c)$. By finding the response of the system 700 to each individual harmonic component (i.e. $\tilde{U}_s(\omega - \omega_c)e^{j\omega t}$), the overall response of the system 700 can be determined using the integral given in Equation 53.

The field of a single harmonic $\tilde{U}_s(\omega - \omega_c)e^{j\omega t}$ at the plane 722 immediately after being dispersed by the grating 720 can be written in the following form:

$$\tilde{U}_{1s}(x; \omega, t) = \tilde{U}_s(\omega - \omega_c)e^{j\omega t}w(x)e^{-jx\left(\frac{\omega-\omega_c}{c}\sin\theta\right)} \quad (54)$$

where w(x) is the pupil function of the optical field on the grating 720, c is the speed of light, x is the coordinate along the plane 722, and θ is the incident angle of the input pulse 710 to the grating 720. This form of the single harmonic field is described by P. C. Sun et al. in *Femtosecond Pulse Imaging: Ultrafast Optical Oscilloscope*, Journal of the Optical Society of America, Vol. 14, 1997, pages 1159-1170, which is incorporated in its entirety by reference herein.

The last exponential term of Equation 54 accounts for the diffraction experienced by the spectral components of the input pulse 710 due to the grating 720, assuming only first-order diffraction. The grating 720 is arranged such that the first diffraction order for the spectral component at $\omega = \omega_c$ propagates along the direction of the optical axis of the system 700. The lens 730 transforms the image at the plane 722 into an image at plane 742. The fields at the two planes 722, 742 are related by a spatial Fourier transform. By taking the spatial Fourier transform of Equation 30, the field at the plane 742 can be written as:

$$\tilde{U}_{2s}(f_{x'}; \omega, t) = \tilde{U}_s(\omega - \omega_c)e^{j\omega t}W\left(f_{x'} + \frac{\omega-\omega_c}{2\pi c}\sin\theta\right) \quad (55)$$

where $W(f_{x'})$ is the spatial Fourier transform of w(x). x' is the coordinate along the plane 742, and $f_{x'}$ is the spatial frequency which can be written as:

$$f_{x'} = \frac{\omega x'}{2\pi c F} \quad (56)$$

where F is the focal length of the lens.

The total response of the system 700 is the spectral decomposition of the field $u_s(t)$ of the input pulse 710 and can be found by integrating Equation 55 over the frequency range, i.e.,:

$$u_{2s}(x';t) = \int \tilde{U}_{2s}(x';\omega,t)d\omega \quad (57)$$

By using the paraxial approximation and by assuming a large illumination window w(x), the total response given by Equation 57 can be simplified to the following form:

$$u_{2s}(x'; t) \approx \tilde{U}_s\left(-\frac{x'\omega_c}{F\sin\theta}\right)w\left(\left[1 - \frac{x'}{F\sin\theta}\right]\frac{ct}{\sin\theta}\right)e^{j\omega_c\left(\left[1 - \frac{x'}{F\sin\theta}\right]t\right)}. \quad (58)$$

By generating a phase conjugate pulse as schematically illustrated in FIG. 25, the total output waveform can be expressed as: $u_{total}(t) = u_s(t) + u_{PC}(t - \Delta t)$, where PC denotes "phase conjugate." The function $u_{PC}(t)$ is dependent on the type of phase conjugate mirror used to generate the phase conjugate pulses. For phase conjugate pulses formed using pulse-pumped FWM, the total field $u_{total}(t)$ can be expressed, using Equation 41, in the following form:

$$u_{total}(t) = (\tilde{u}_s(t) + \tilde{u}_s^*(-t - \Delta t))e^{j\omega_c t} \quad (59)$$

where Δt is the time delay between the original pulse and its corresponding phase conjugate pulse. Feeding this total field into the system 700 illustrated in FIG. 31, the resultant image field at the plane 742 of the CCD imaging device 740, using Equation 58, can be expressed as:

$$u_{total,2}(x';t) \approx \tilde{U}_s\left(-\frac{x'\omega_c}{F\sin\theta}\right)w\left(\left[1-\frac{x'}{F\sin\theta}\right]\frac{ct}{\sin\theta}\right)e^{j\omega_c\left(\left[1-\frac{x'}{F\sin\theta}\right]t\right)} + \tilde{U}_s^*\left(-\frac{x'\omega_c}{F\sin\theta}\right)w\left(\left[1-\frac{x'}{F\sin\theta}\right]\frac{ct}{\sin\theta}\right)e^{j\omega_c\left(\left[1-\frac{x'}{F\sin\theta}\right]t\right)}e^{j\Delta t\left(-\frac{x'\omega_c}{F\sin\theta}\right)} \quad (60)$$

The CCD imaging device 740 at the plane 742 is responsive to intensity, which can be written as:

$$I(x') = \int |u_{total,2}(x';t)|^2 dt. \quad (61)$$

Defining $\tilde{U}_s(\omega) = |\tilde{U}_s(\omega)|e^{j\Phi(\omega)}$ and $A=-F\sin\theta$, Equation 61 can be rewritten as:

$$I_{double}(x') = 2\left(\int \left|w\left(\left[1+\frac{x'}{A}\right]\frac{ct}{\sin\theta}\right)\right|^2 dt\right) \left|\tilde{U}_s\left(\frac{x'\omega_c}{A}\right)\right|^2 \left[1+\cos\left(2\Phi\left(\frac{x'\omega_c}{A}\right)-\Delta t\frac{x'\omega_c}{A}\right)\right]. \quad (62)$$

Furthermore, Equation 62 can be rewritten as:

$$I_{double}(x') = 2G(x')\left|\tilde{U}_s\left(\frac{x'\omega_c}{A}\right)\right|^2\left[1+\cos\left(2\Phi\left(\frac{x'\omega_c}{A}\right)-\Delta t\frac{x'\omega_c}{A}\right)\right] \quad (63)$$

with $G(x') = \int \left|w\left(\left[1+\frac{x'}{A}\right]\frac{ct}{\sin\theta}\right)\right|^2 dt.$ Equation 63 is very similar to Equation 50, which was obtained for embodiments utilizing the intensity correlator of FIG. 24. Furthermore, the intensity profile on the CCD imaging device 740 for a single pulse $u_s(t)$ can be expressed as:

$$I_{single}(x') = G(x')\left|\tilde{U}_s\left(\frac{x'\omega_c}{A}\right)\right|^2. \quad (64)$$

Equation 64 is also very similar to Equation 47, which was derived above in relation to the intensity correlator embodiment as shown in FIG. 24.

Figure 33:
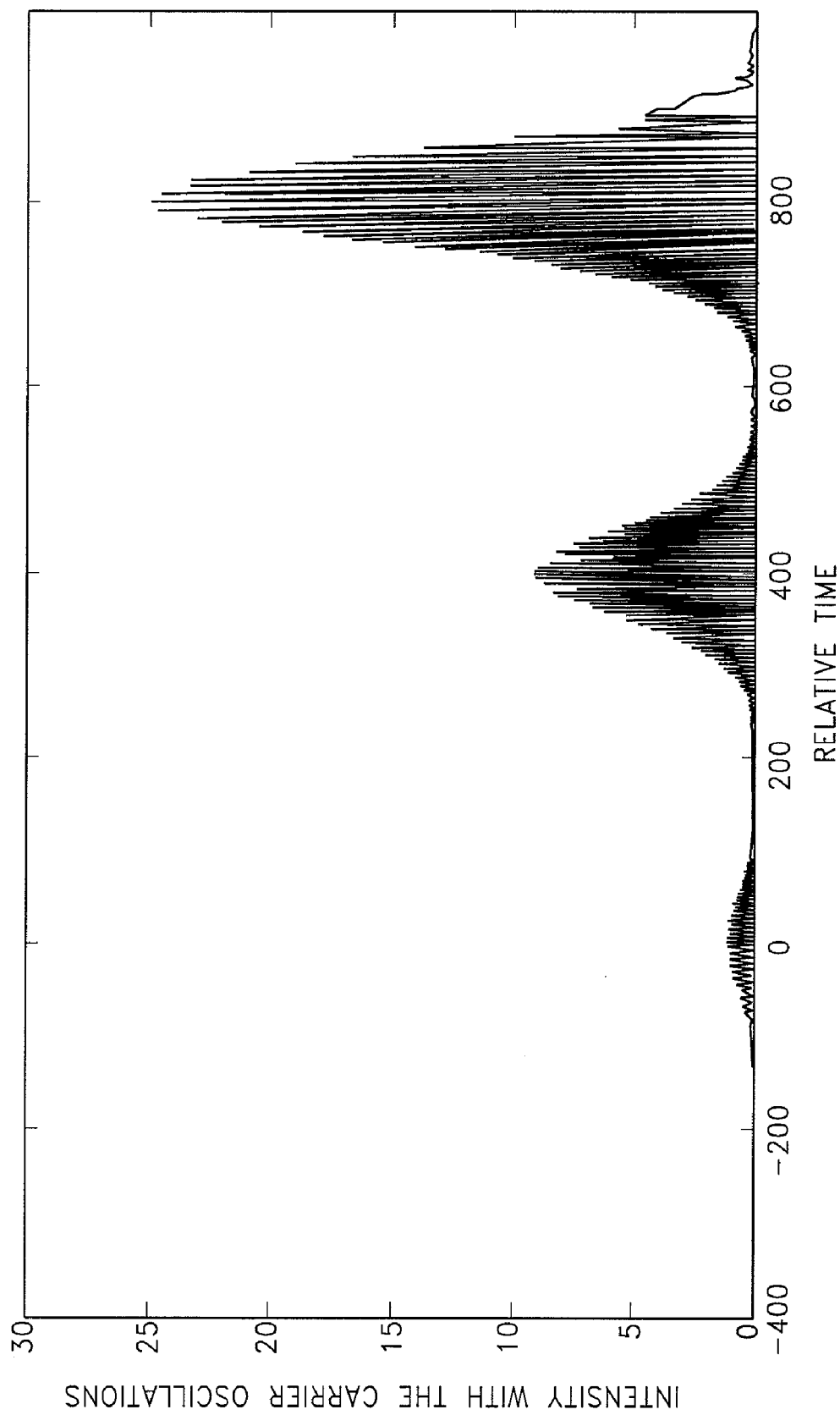
FIG. 33 illustrates the intensity profile (in units of W/m²) for the asymmetric complex envelope function of FIG. 32A with the carrier frequency oscillations.
Figure 34:
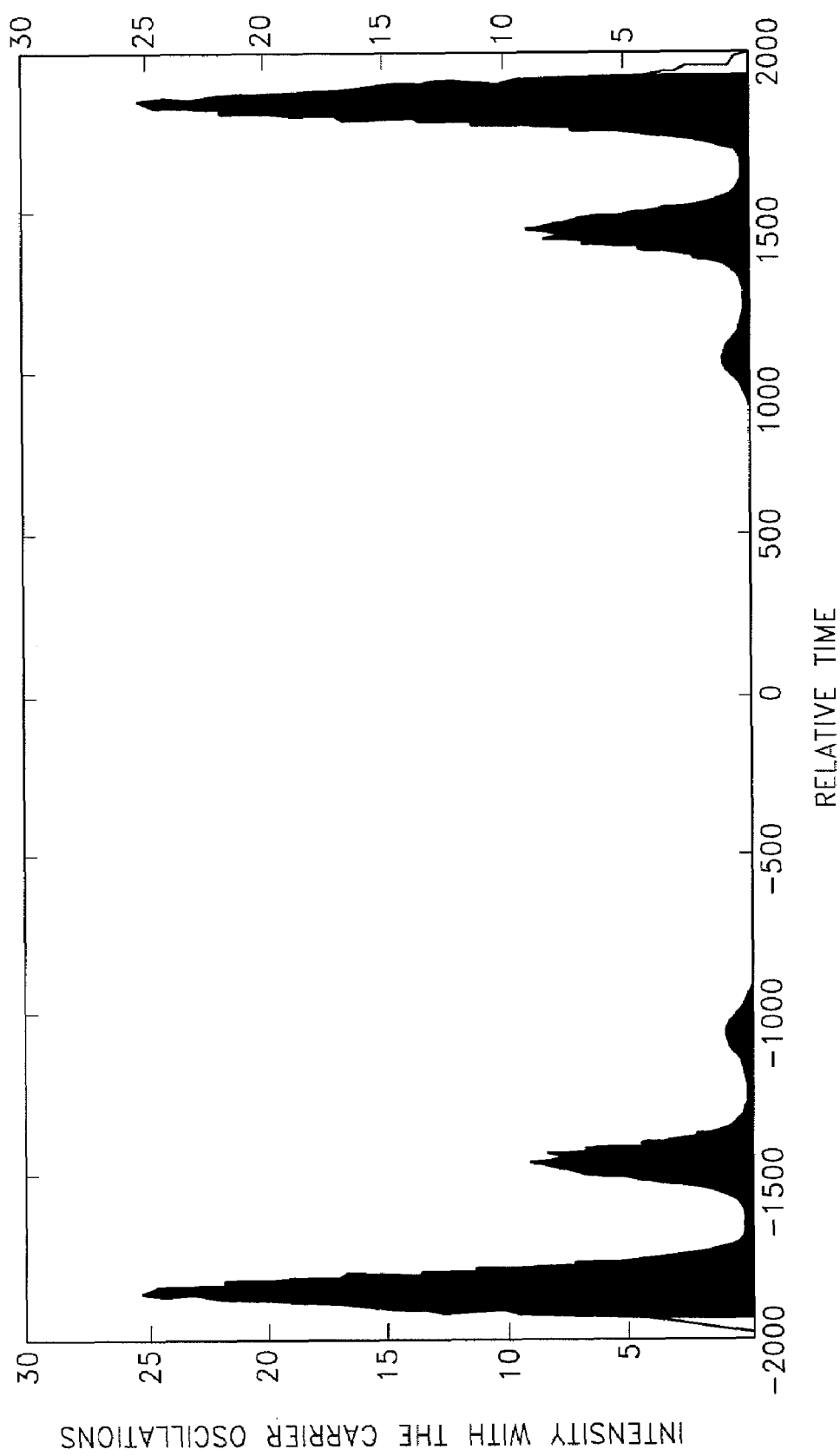
FIG. 34 illustrates the symmetric temporal waveform (in units of W/m²) with the carrier frequency corresponding to the asymmetric complex envelope function of FIG. 33.

To recover the complex envelope function $\tilde{u}_s(t)$, as defined in Equation 52, the same algorithm described above for recovering I(t) can be applied. This process is illustrated in the FIGS. 32 through 37 using computer-generated simulations. FIGS. 32A and 32B illustrate the magnitude (intensity) and phase of an arbitrary asymmetric complex envelope function $\tilde{u}_s(t)$ to be characterized, respectively. (FIG. 32A is the same input pulse as shown in FIG. 26). FIG. 33 illustrates the intensity profile for this complex field, including the carrier frequency oscillations. Note that FIG. 26 described above did not include the carrier frequency oscillations and was just the envelope of the intensity. In a first step, the general configuration 600 of FIG. 25 is used to generate the symmetric temporal waveform whose complex envelope function is defined by Equation 59. FIG. 34 illustrates the symmetric temporal waveform, including the carrier frequency, generated by this first step. The symmetric temporal waveform comprises the temporal waveform of the original pulse plus the time-delayed temporal waveform of the time-reversed pulse.

Figure 35A:
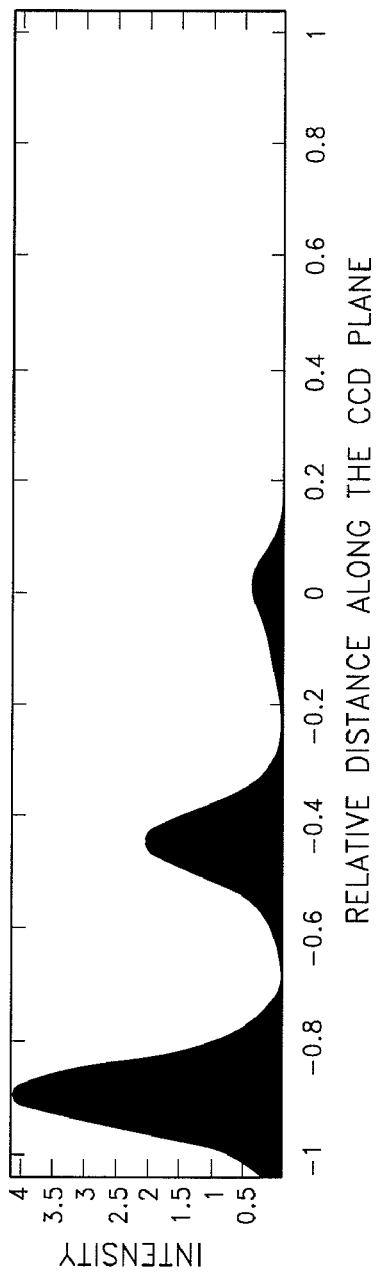
FIGS. 35A and 35B illustrate the detected intensity (in units of W/m²) on the CCD imaging device for the symmetric pulse of FIG. 34, and the single pulse of FIG. 33, respectively.
Figure 35B:
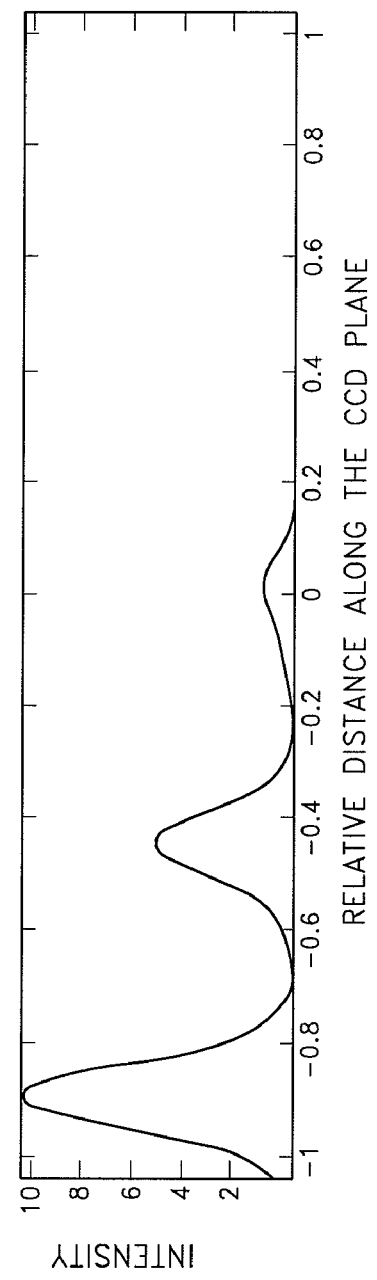

In a second step, the system of FIG. 31 is used to measure the Fourier transform magnitude of the symmetric pulse with the CCD imaging device. FIG. 35A illustrates the detected intensity I(x') on the CCD imaging device at the plane 742 for the symmetric pulse of FIG. 34. The intensity I(x') was calculated using Equation 63. For comparison, FIG. 35B shows the detected intensity I(x') on the CCD imaging device at the plane 742 using the original pulse of FIG. 33, which is a prior art measurement technique. The intensity I(x') was calculated using Equation 64.

Figure 36A:
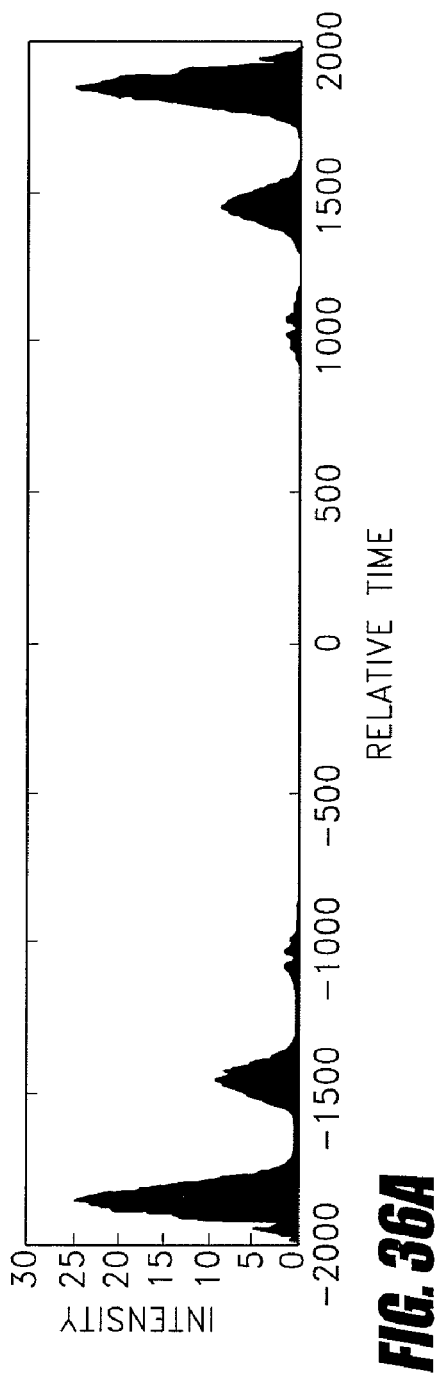
FIGS. 36A and 36B illustrate the recovered symmetric temporal waveform and the original temporal waveform (in units of W/m²), respectively, including the carrier frequencies.
Figure 36B:
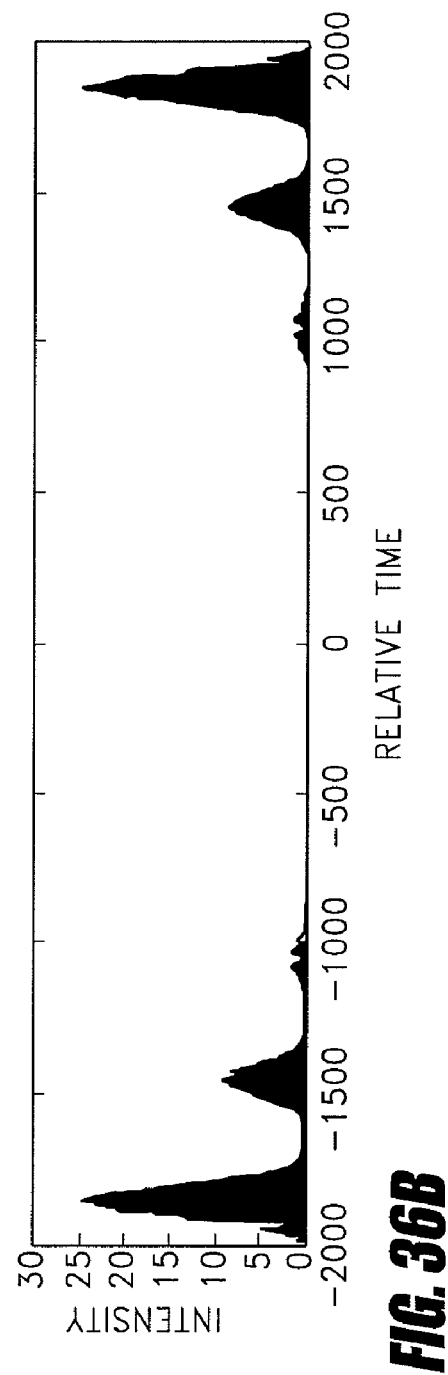
Figure 37:
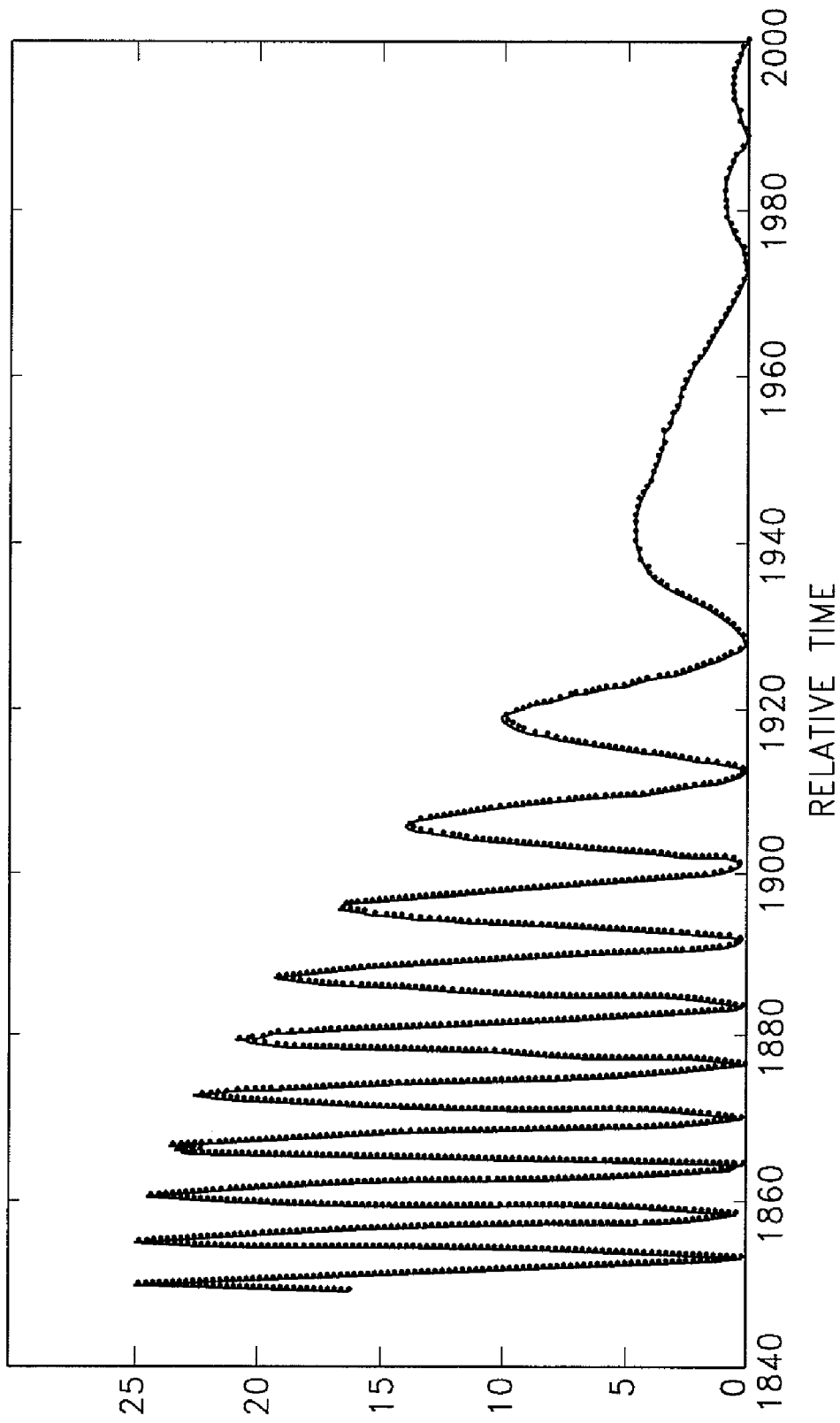
FIG. 37 illustrates the waveforms of FIGS. 36A and 36B (in units of W/m²) overlaid with one another in an expanded time frame for comparison purposes.

In a third step, and as discussed above in relation to determining I(t) using the intensity correlation configuration of FIG. 24, the CCD image (FIG. 35A) is used to calculate numerically both amplitude and the phase of the Fourier transform of the complex envelope function $\tilde{u}_s(t)$. The complex envelope function $\tilde{u}_s(t)$ can be calculated using inverse Fourier transform once both the amplitude and the phase functions of the Fourier transform are recovered. FIGS. 36A and 36B illustrate the recovered symmetric temporal waveform and the original temporal waveform, respectively, including the carrier frequencies. FIG. 37 illustrates these waveforms overlaid with one another in an expanded time frame for comparison purposes. This comparison establishes that the prediction of the pulse shape made available by this invention is excellent. The discrepancy between the two curves of FIG. 37 is in fact a numerical artifact that can be removed by increasing the computation accuracy.

Therefore, using the same process as described above in relation to Equation 50, the system 700 of FIG. 31 can be used to recover the complex envelope function $\tilde{u}_s(t)$ of any given input pulse using only the Fourier transform amplitude of the symmetrized composite waveform. In addition, both the envelope of the intensity profile I(t) and the underlying optical oscillations are recoverable, as illustrated by FIG. 37. Recovering both the envelope and the underlying oscillations is an improvement with respect to the prior art intensity correlation embodiment described above, which only recovers the envelope of I(t).

As described above, the waveform of an ultra-short optical pulse is determined in certain embodiments by using time-reversal techniques to yield a time-reversed replica of the pulse and to obtain a symmetric optical pulse. The Fourier transform magnitude of the symmetric optical pulse is used to uniquely recover the original time-domain optical pulse waveform. Such time-reversal techniques utilize shorter optical pulses with respect to the input optical pulse waveform being measured. For example, to determine the temporal pulse waveform of a femtosecond-scale optical pulse, sub-femtosecond-scale pulses are used to form the symmetric optical pulse waveform by time reversal.

Figure 38:
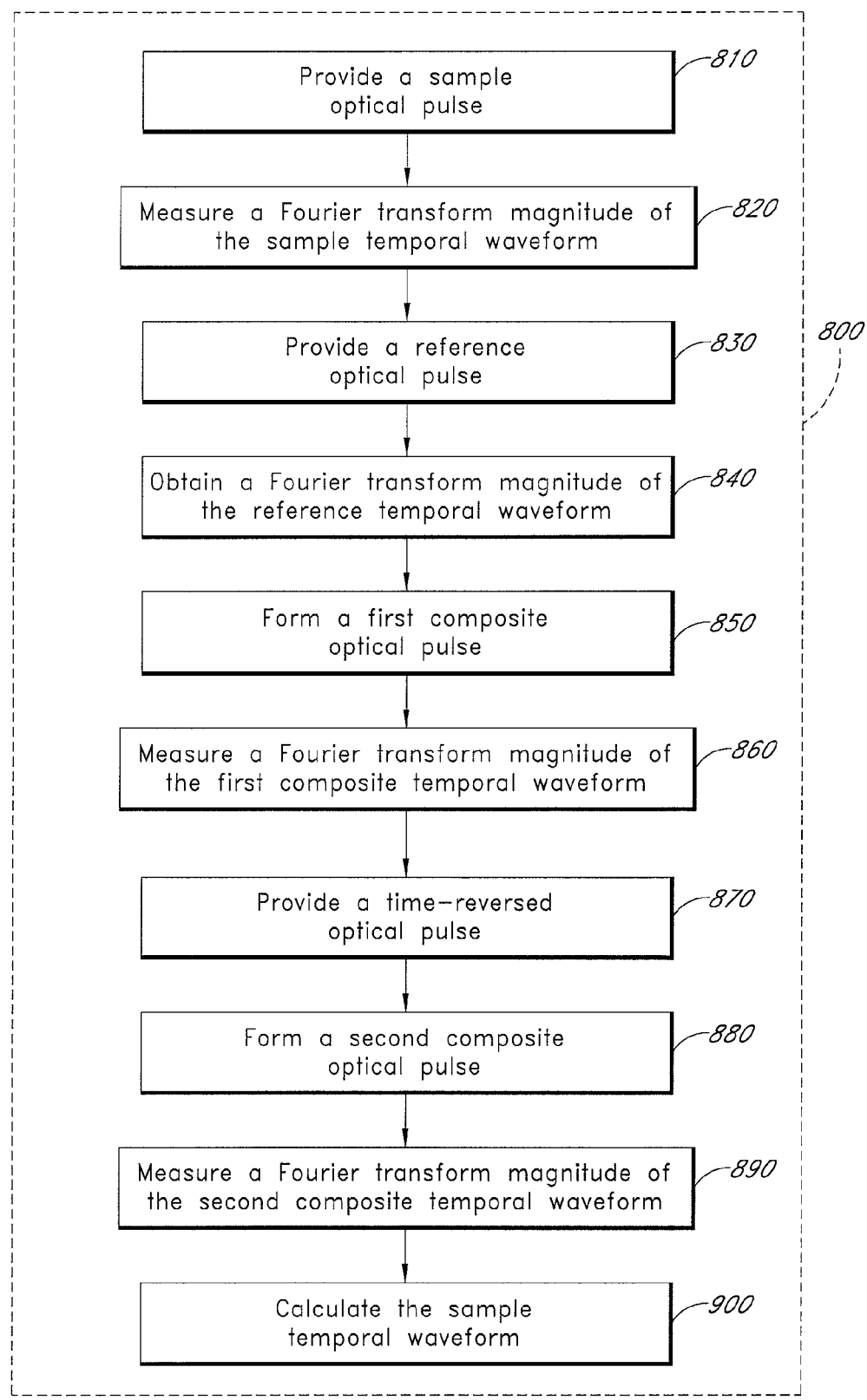
FIG. 38 is a flow diagram of a method of measuring a sample temporal waveform of a sample optical pulse in accordance with embodiments of the present invention.

This experimental limitation of using pulses shorter than the input pulse waveform can present a challenge which can hinder the application of the method in certain circumstances. However, in certain embodiments, a method determines the temporal waveform of an optical pulse using the Fourier transform magnitudes of four pulse waveforms and avoiding the limitation of short pulses. FIG. 38 is a flow diagram of a method 800 in accordance with embodiments of the present invention. In an operational block 810, a sample optical pulse having a sample temporal waveform is provided. In an operational block 820, a Fourier transform magnitude of the sample temporal waveform is measured. In an operational block 830, a reference optical pulse having a reference temporal waveform is provided. In an operational block 840, a Fourier transform magnitude of the reference temporal waveform is obtained. In an operational block 850, a first composite optical pulse having a first composite temporal waveform is formed. The first composite optical pulse comprises the sample optical pulse followed by the reference optical pulse. In an operational block 860, a Fourier transform magnitude of the first composite temporal waveform is measured. In an operational block 870, a time-reversed optical pulse having a time-reversed temporal waveform is provided. The time-reversed temporal waveform corresponds to the reference temporal waveform after being time-reversed. In an operational block 880, a second composite optical pulse having a second composite temporal waveform is formed. The second composite optical pulse comprises the sample optical pulse followed by the time-reversed optical pulse. In an operational block 890, a Fourier transform magnitude of the second composite temporal waveform is measured. In an operational block 900, the sample temporal waveform is calculated using the Fourier transform magnitude of the sample temporal waveform, the Fourier transform magnitude of the reference temporal waveform, the Fourier transform magnitude of the first composite temporal waveform, and the Fourier transform magnitude of the second composite temporal waveform.

The sample optical pulse of certain embodiments can have an ultra-short temporal waveform (e.g., on the order of femtoseconds or sub-femtoseconds). The reference optical pulse of certain embodiments can have a temporal waveform which is significantly more broad than the temporal waveform of the sample optical pulse. For example, for a femtosecond sample temporal waveform, the width of the reference temporal waveform can be on the order of nanoseconds. By allowing the use of reference optical pulses with broader temporal waveforms, embodiments of the present invention allow for easier time-reversal processes, since the optical pulses used to time-reverse the reference optical pulse can be correspondingly broader. In certain such embodiments, the sample optical pulse itself can be used to time-reverse the reference optical pulse.

In certain embodiments, the first composite optical pulse includes a time delay between the sample optical pulse and the reference optical pulse. In certain such embodiments, the time delay can be adjusted to make the measurement of the Fourier transform magnitude easier. The time delay used can be dependent upon the particular technique used to measure the Fourier transform magnitude. Similarly, in certain embodiments, the second composite optical pulse includes a time delay between the sample optical pulse and the time-reversed optical pulse, and the time delay can be adjusted to ease the measurement of the Fourier transform magnitude depending on the particular measurement technique used.

In certain embodiments, the Fourier transform magnitudes of the sample temporal waveform, the reference temporal waveform, the first composite temporal waveform, and the second composite temporal waveform are measured using an auto-correlator as described above, or using other holographic techniques. In certain embodiments, obtaining the Fourier transform magnitude of the reference temporal waveform comprises measuring the Fourier transform magnitude. In other embodiments, the Fourier transform magnitude of the reference temporal waveform is previously measured and stored in memory, and obtaining the Fourier transform magnitude comprises reading the Fourier transform magnitude from memory.

Using the four Fourier transform magnitudes in the same manner as described above for measuring the sample non-linearity profile, the sample temporal waveform can be measured. Note that the reference temporal waveform can also be calculated by embodiments of the present invention concurrently with the calculation of the sample temporal waveform. However, because the reference optical pulse is temporally broad, its temporal waveform is of less interest than that of the sample optical pulse. In embodiments in which the same reference optical pulse is used to measure the temporal waveforms of a series of sample optical pulses, the calculated series of reference temporal waveforms can be compared to one another, thereby providing a check of the validity of the measurements across the series of calculations.

In the embodiment described above, the quantities of interest (the intensity profiles of the two arbitrary ultra-short pulse waveforms) are by definition real and positive. In other more general embodiments, two totally arbitrary and different ultra-short pulse waveforms can be used together to determine the pulse profiles $I_A(t)$, $I_B(t)$ of both pulses. In such embodiments, the Fourier transform amplitudes of two composite pulse waveforms are measured. These two composite pulse waveforms can be expressed as:

$$I_{C1}(t)=I_A(t)+I_B(t-\tau_1); \text{ and} \quad (65)$$

$$I_{C2}(t)=I_A(t)+I_B(-t+\tau_2) \quad (66)$$

where $\tau_1$ and $\tau_2$ are time delays between the pulses. As described above, a classical auto-correlator can be used to generate the Fourier transform amplitudes of the pulse waveforms. Time reversal techniques are utilized in such embodiments due to the $I_B(-t+\tau_2)$ term. As described above, by using a broader reference pulse waveform, the time reversal is simpler to achieve to determine the pulse shape of an ultra-short sample pulse waveform.

Figure 39:
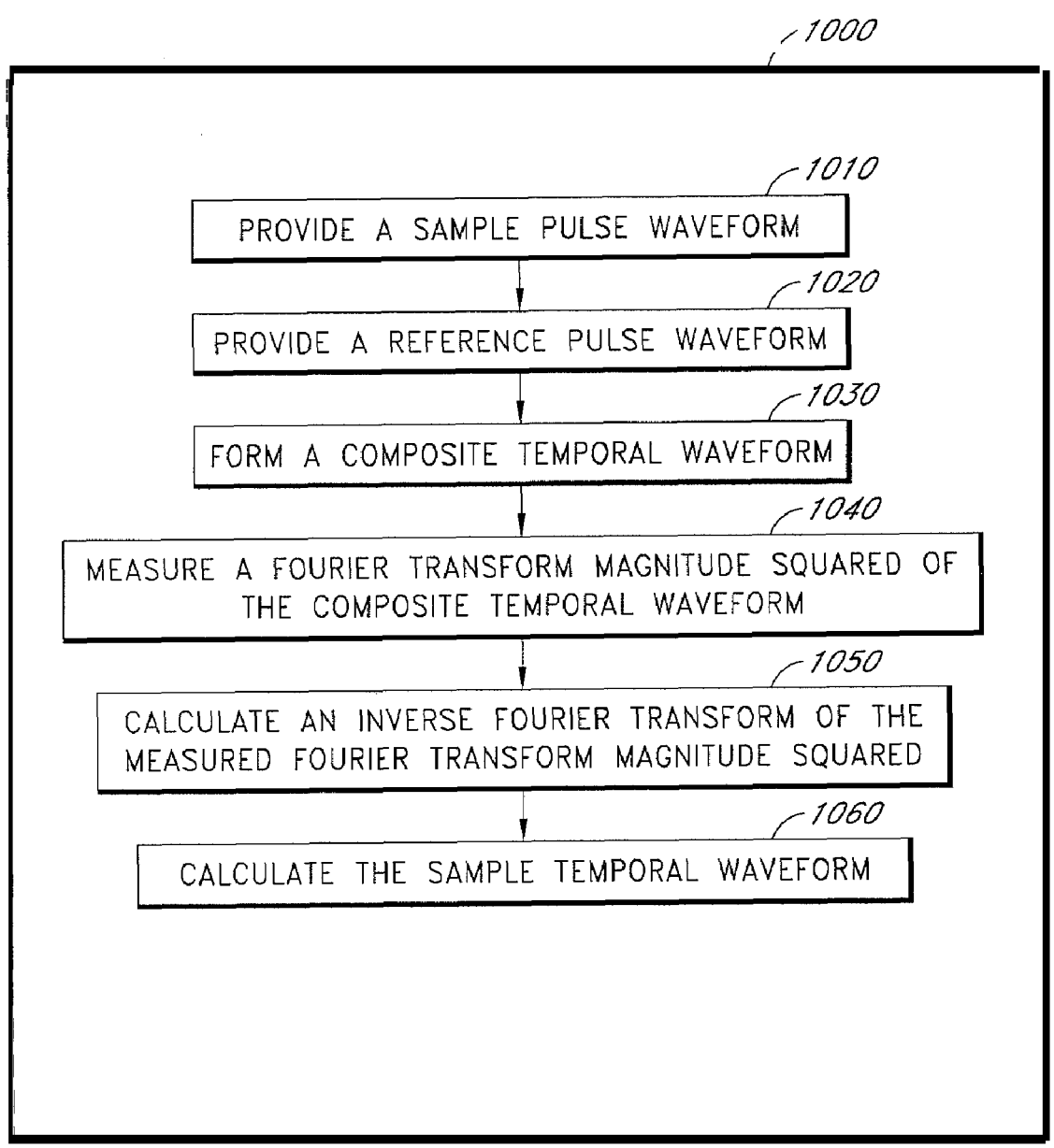
FIG. 39 is a flow diagram of another method of measuring a sample temporal waveform of a sample optical pulse in accordance with embodiments of the present invention.

In certain embodiments, the temporal shape of ultra-short pulse waveforms can be determined without using time reversal techniques, thereby providing an improved method. FIG. 39 is a flow diagram of a method 1000 in accordance with certain embodiments of the present invention. In an operational block 1010, a sample pulse waveform having a sample temporal waveform is provided. In an operational block 1020, a reference pulse waveform is provided. In an operational block 1030, a composite temporal waveform is formed. The composite temporal waveform comprises the sample pulse waveform and the reference pulse waveform with a relative delay between the sample pulse waveform and the reference pulse waveform. In an operational block 1040, a Fourier transform magnitude squared of the composite temporal waveform is measured. In an operational block 1050, an inverse Fourier transform of the measured Fourier transform magnitude squared is calculated. In an operational block 1060, the sample temporal waveform is calculated using the calculated inverse Fourier transform.

In certain embodiments, the reference waveform $I_{Ref}(t)$ is symmetric and unchirped (i.e., $I_{Ref}(t)=I_{Ref}(-t)$). In certain embodiments, the composite temporal waveform $I_C(t)$ can be expressed as:

$$I_C(t)=I(t)+I_{ref}(t-\tau) \quad (67)$$

where I(t) is the sample temporal waveform, and τ is a time delay between the sample and reference pulse waveforms.

Similarly to the measurement of optical nonlinearities described above, the following relation can be derived:

$$|I_C(f)|^2=|I(f)|^2+|I_{Ref}(f)|^2+2|I_{Ref}(f)||I(f)|\cos(\phi-\phi_{Ref}+\phi_0) \quad (68)$$

where $I(f)=|I(f)|e^{j\phi}$ is the Fourier transform of the sample pulse waveform, $I_{Ref}(f)=|I_{Ref}(f)|e^{j\phi_{Ref}}$ is the Fourier transform of the reference pulse waveform, and $I_C(f)$ is the Fourier transform of the composite waveform with ($\phi_0=2\pi f\tau$).

In certain such embodiments in which the square of the Fourier transform magnitude of the composite temporal waveform is measured in the operational block 1040, the Fourier transform magnitude squared of the composite waveform is expressed as Equation 68. The operational block 1050 then comprises calculating an inverse Fourier transform of the measured Fourier transform magnitude squared. For a selected time delay $\tau>(T_{Ref}+T)$, where T is the temporal width of the sample pulse waveform and $T_{Ref}$ is the temporal width of the reference pulse waveform, the inverse Fourier transforms of $[|I(f)|^2+|I_{Ref}(f)|^2]$ and $[2|I(f)||I_{Ref}(f)|\cos(\phi-\phi_{Ref}+\phi_0)]$ do not overlap in time. This observation implies that from the inverse Fourier transform of $|I_C(f)|^2$, one can recover the inverse Fourier transforms of both $[|I(f)|^2+|I_{Ref}(f)|^2]$ and $[2|I(f)||I_{Ref}(f)|\cos(\phi-\phi_{Ref}+\phi_0)]$ distinctly.

In certain embodiments, using only the t>0 portion of the inverse Fourier transform of $[2|I(f)||I_{Ref}(f)|\cos(\phi-\phi_{Ref}+\phi_0)]$, one can get the convolution of the sample pulse waveform I(t) with the reference pulse waveform $I_{Ref}(-t)$, i.e., $Conv(t)=I(t)*I_{Ref}(-t)=\int I(\beta)I_{Ref}(-t+\beta)d\beta$. Taking the phase of the Fourier transform of Conv(t) yields $\phi-\phi_{Ref}$, and taking the magnitude of the Fourier transform of Conv(t) yields $|I_{Ref}(f)||I(f)|$. Since the quantities $[|I(f)|^2+|I_{Ref}(f)|^2]$ and $|I_{Ref}(f)||I(f)|$ are known, the functions $|I(f)|$ and $|I_{Ref}(f)|$ can be determined simultaneously.

Since $I_{Ref}(t)$ is a real, even, and non-negative function, its Fourier transform is also real and even, meaning that $\phi_{Ref}$ equals either 0 or $\pi$. Using a Hartley transform-based algorithm as described above, $\phi_{Ref}$ can be fully determined using only the information of $|I_{Ref}(f)|$. Note that for a real and even function, the Hartley transform is the same as the Fourier transform.

Once $\phi_{Ref}$ is fully determined, the phase of the Fourier transform of Conv(t) can be used to determine the phase $\phi$ of the Fourier transform of I(t), the sample pulse waveform. Thus, the quantity $I(f)=|I(f)|e^{j\phi}$ is recovered, and by taking the inverse Fourier transform, the sample pulse waveform I(t) can be determined.

Usually for unchirped symmetrical optical pulses (e.g., $I_{Ref}(t)$), the intensity profile is gaussian-like, and the corresponding Fourier transforms are also gaussian-like. This result implies that $\phi_{Ref}$ equals zero. Therefore, in practical cases in which the reference pulse waveform is gaussian-like, there is no need to determine $\phi_{Ref}$ using Hartley transform based algorithms.

The method described above can be used to determine the temporal shape of an ultra-short sample pulse waveform using a symmetric unchirped reference pulse waveform using only one measurement (e.g., an auto-correlator measurement). The recovery of the sample pulse waveform using the method described above is robust, even in the presence of noise added to the measured Fourier transform magnitudes.

In addition, once a pulsed laser system has been characterized using this method (i.e., the temporal pulse waveform has been determined), the laser can then be used to characterize other pulsed laser sources, even though neither laser has symmetric output pulses. For example, after an initial measurement to characterize a non-symmetric sample pulse waveform using an unchirped symmetric pulse, one can continue to characterize different pulse waveforms using the non-symmetric pulse waveform that has been previously characterized as the reference pulse waveform for the subsequent measurements.

This invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. A method of measuring a temporal waveform of a pulse, the method comprising:
   obtaining a Fourier transform magnitude of the temporal waveform of the pulse;
   obtaining a Fourier transform magnitude of a reference temporal waveform of a reference pulse;
   obtaining a Fourier transform magnitude of a first composite temporal waveform of a first composite pulse comprising the pulse followed by the reference pulse;
   obtaining a Fourier transform magnitude of a second composite temporal waveform of a second composite pulse comprising the pulse followed by a time-reversed pulse having a time-reversed temporal waveform corresponding to the reference temporal waveform after being time-reversed;
   calculating the temporal waveform using the Fourier transform magnitude of the temporal waveform, the Fourier transform magnitude of the reference temporal waveform, the Fouler transform magnitude of the first composite temporal waveform, and the Fourier transform magnitude of the second composite temporal waveform; and
   using the calculated temporal waveform to provide information regarding the temporal waveform of the pulse.

2. The method of claim 1, wherein the pulse and the reference pulse are optical pulses and obtaining the Fourier transform magnitude of the time-reversed pulse comprises providing the time-reversed pulse using four-wave mixing.

3. The method of claim 1, wherein the pulse and the reference pulse are optical pulses and obtaining the Fourier transform magnitude of the time-reversed pulse comprises providing the time-reversed pulse using spectral holography.

4. The method of claim 1, wherein the reference pulse is broader than the pulse.

5. The method of claim 4, wherein obtaining the Fourier transform magnitude of the time-reversed pulse comprises providing the time-reversed pulse using the pulse to time-reverse the reference pulse.

6. The method of claim 4, wherein the pulse has a temporal width on the order of femtoseconds and the reference pulse has a temporal width on the order of nanoseconds.

7. The method of claim 1, wherein the first composite pulse includes a time delay between the pulse and the reference pulse.

8. The method of claim 1, wherein the second composite pulse includes a time delay between the pulse and the time-reversed pulse.

9. The method of claim 1, further comprising calculating the reference temporal waveform using the Fourier transform magnitudes of the temporal waveform, the reference temporal waveform, the first composite temporal waveform, and the second composite temporal waveform.

10. A method of measuring temporal waveforms of a plurality of pulses, the method comprising:
  (a) measuring a first temporal waveform of a first pulse using the method of claim 1;
  (b) measuring a second temporal waveform of a second pulse using the method of claim 1, wherein the same reference pulse is used to measure the first and second temporal profiles; and
  comparing the calculated reference temporal waveforms from (a) and (b) to provide an indication of the consistency of the measurements of the first and second temporal profiles.

11. A method of measuring a temporal waveform of a pulse, the method comprising:
  forming a composite pulse comprising the pulse having the temporal waveform followed by a reference pulse having a reference temporal waveform with a relative delay between the temporal waveform and the reference temporal waveform;
  measuring a Fourier transform magnitude squared of the composite pulse;
  calculating an inverse Fourier transform of the measured Fourier transform magnitude squared;
  calculating the temporal waveform using the calculated inverse Fourier transform; and
  using the calculated temporal waveform to provide information regarding the temporal waveform of the pulse.

12. The method of claim 11, wherein the reference pulse is broader than the pulse.

13. The method of claim 12, wherein the pulse has a temporal width on the order of femtoseconds and the reference pulse has a temporal width on the order of nanoseconds.

14. A method of determining the temporal waveform of an electromagnetic pulse, the method comprising:
  forming a symmetric composite waveform by combining a temporal waveform of an electromagnetic pulse and a time-reversed temporal waveform of a time-reversed pulse, the time-reversed temporal waveform corresponding to the temporal waveform of the electromagnetic pulse after being time-reversed;
  calculating an inverse Fourier transform of a Fourier transform of the symmetric composite waveform, the calculated inverse Fourier transform providing information regarding the temporal waveform of the electromagnetic pulse; and
  displaying the information regarding the temporal waveform of the electromagnetic pulse.

15. The method of claim 14, wherein the time-reversed pulse is provided using four-wave mixing.

16. The method of claim 14, wherein the time-reversed pulse is provided using spectral holography.

17. A method of measuring a temporal waveform of a pulse, the method comprising:
  forming a symmetric composite function by combining the temporal waveform of the pulse with a reference function;
  obtaining a measured Fourier transform of the symmetric composite function; and
  calculating an inverse Fourier transform of the measured Fourier transform of the symmetric composite function, wherein the calculated inverse Fourier transform provides information regarding the temporal waveform; and
  displaying the information.

18. The method of claim 17, wherein the temporal waveform is symmetric.

19. The method of claim 17, wherein the temporal waveform is non-symmetric.

* * * * *